United States Patent [19]

Goldstein et al.

[11] 3,966,764

[45] June 29, 1976

[54] LIGAND DETERMINATION OF SPIN LABELED COMPOUNDS BY RECEPTOR DISPLACEMENT-AMPHETAMINE ANALOGS

[75] Inventors: Avram Goldstein, Stanford; Richard K. Leute, Sunnyvale; Edwin F. Ullman, Atherton, all of Calif.

[73] Assignee: Syva Company, Palo Alto, Calif.

[22] Filed: June 24, 1974

[21] Appl. No.: 482,200

Related U.S. Application Data

[62] Division of Ser. No. 270,108, July 10, 1972, Pat. No. 3,853,914.

[52] U.S. Cl.................... 260/326.85; 260/239.3 R; 260/241; 260/285; 260/293.76; 260/295 R; 260/302 R; 260/307 R; 260/309.6; 260/326.62; 23/230 R; 424/2; 424/9; 424/330

[51] Int. Cl.²....................................... C07D 207/14

[58] Field of Search............. 260/239, 293.78, 326.2

[56] References Cited
UNITED STATES PATENTS 3,818,008  6/1974  Eberle............................. 260/326.85
3,821,204  6/1974  Enders............................ 260/326.85

*Primary Examiner*—Dale R. Ore
*Attorney, Agent, or Firm*—Townsend and Townsend

[57] ABSTRACT

Compounds are provided for use in assays of organic compounds, where organic compounds of biological interest are determined at extremely low concentrations by combining in a medium, the composition to be determined, hereinafter referred to as ligand, a high molecular weight material of at least 10,000 molecular weight, which has a site spatially characteristic of the ligand, hereinafter referred to as receptor, and an analog of the ligand having a free radical functionality, hereinafter referred to as "ligand analog". The ligand analog and ligand in the medium compete for the receptor site, the amount of ligand analog bound to the receptor, being dependent on the amount of ligand present in the medium. By following the change in electron spin resonance spectrum of the ligand analog and comparing it to the change in spectrum which would be obtained in the absence of any ligand, the amount of ligand can be determined.

6 Claims, No Drawings

LIGAND DETERMINATION OF SPIN LABELED COMPOUNDS BY RECEPTOR DISPLACEMENT AMPHETAMINE ANALOGS

This is a division of application Ser. No. 270,180 filed July 10, 1972 now U.S. Pat. No. 3,853,914.

BACKGROUND OF THE INVENTION

1. Field of the Invention

There is a continuing need for accurate and efficient methods for the rapid analysis of small quantities of organic compounds. Such need is related to widely different areas requiring the determination of minute quantities of organic materials. The need to assay diverse substances, from pollutants in water, soil or air which may be present in extremely small quantities to drugs or naturally occurring physiologically active materials, in body fluids, such as blood, urea and saliva, exemplifies the vast array of siutations in which determinations of minute quantities of material are required.

More specifically, both as a medical and police function, the abuse of narcotics and drugs requires an easy method for rapid detection of the use of such drugs, either immediately after ingestion or injection or frequently, after a relatively extended period. The assay should be effective either for the drug, its metabolite, or both, individually or together, and should be specific for the drug being assayed, and not be interfered with by other materials which may be present in the body fluid.

Where the body is malfunctioning, it may be important to assay for particular compounds or metabolites, so as to diagnose the particular malfunction. Also, in case of poisonings, an easy and rapid method for determining the toxin, could be extremely important in providing the antidote.

A wide variety of methods exist for analyzing for a broad spectrum of different organic compounds. Many of these methods are dependent upon different types of detection instruments, such as fluorometers, ultraviolet spectrophotometers, gravimetric analyses, titrimetric analyses, etc. Other methods depend on thin layer chromatography, which is frequently slow, is subject to interference, and may not be reproducible. Because of the significant differences in the procedures, accuracies, and the presence of interfering materials, many diagnostic tests cannot be routinely carried out because of expense and lack of equipment.

2. Description of the Prior Art

The use of free radical probes with naturally occurring materials is found in U.S. Pat. Nos. 3,489,522 and 3,453,288. Labeling of various high molecular weight proteins is described in U.S. Pat. No. 3,481,952. See also Hubbell, et al, Proc. Nat Acad. Sci. U.S., 61, 12 (1968). Organic free radicals have been joined with antibodies and studied. L. Stryer and O. Hayes Griffith, Proc. Nat. Acad. Sci. U.S. 54, 1785 (1965); and J. C. Hsia and L. H. Piette, Arch. Biochem. and Biophys., 132, 466 (1969). In the latter reference, dinitrophenyl antibodies were labeled with 2,4-dinitrophenyl spin labels and the changes in the electron spin resonance (ESR) spectrum were observed as a result of the interaction between the labels and antibodies.

Steroids have been spin labeled by either preparing the oxazole of the 3-keto steroid and oxidizing the nitrogen to the nitroxide or using a carboxyalkyl at the 17 position to form the amide of a tetramethyl(amino)-piperidino-oxyl group. See McConnell, et al., Quart. Rev. of Biophys., 3 91–136 (1970); and Hamilton, et al., Structural Chemistry and Molecular History, W. H. Freeman & Co., San Francisco, California (1968), the chapter on spin labels. See also Hubbell, Proc. Nat. Acad. Sci. U.S. 63, 16 (1963).

See also copending application Ser. No. 794,008, filed January 27, 1969, now abandoned, which discloses the use of nitroxide free radical compounds in determining the changes in pH.

REFERENCES TO RELATED APPLICATIONS

This application is a continuation in part of U.S. application Ser. Nos. 105,535, filed Jan. 11, 1971, now abandoned, and 141,516, filed May 10, 1971, issued as U.S. Pat. No. 3,690,834.

SUMMARY OF THE INVENTION

Spin labeled compounds (ligand analogs) are provided for use in immunoassays. Biologically active compounds or structural analogs are modified and coupled with a stable free radical compound, so as to provide a ligand analog which: (1) is recognized by a receptor molecule, ordinarily an antibody, and (2) can compete with a biologically active molecule (ligand) for the receptor site in a manner which permits the biologically active molecule to be assayed.

Particularly, biologically active compounds are functionalized or available functional groups employed to link with a stable free radical compound, usually a cyclic nitroxide. The manner of functionalizing and linking to the stable free radical compound provides a product which binds to the receptor specifically and has a binding constant which alllows for effective competition with a ligand. Changes in spectrum between ligand analog bound to receptor and unbound ligand analog rotating free in solution permit a quantitative determination of the amount of ligand present, since the ratio of bound to unbound ligand analog is affected by the amount of ligand present in the solution.

DESCRIPTION OF THE SPECIFIC EMBODIMENTS

The compounds of this invention referred to as ligand analogs have three essential parts: (1) a group of atoms forming a moiety recognizable by a receptor and when joined to the other parts, the total has a binding constant to a receptor, which allows for competition between the subject compound and a compound to be assayed (modified ligand moiety); (2) a stable free radical group having an electron spin resonance spectrum which is capable of being detected at low concentrations and which changes in a detectable manner, when bound to a receptor, as contrasted to being unbound and free to rotate in solution (free radical moiety); and (3) a linking group, joining the modified ligand moiety to the free radical moiety, which cooperates with the other parts of the molecule in allowing or enhancing the capability of the moieties joined by the linking group to fulfill their function.

The first part will substantially resemble at least a part of the ligand to be assayed. Usually, the ligand to be assayed will be modified to only a minor degree, for example, by replacement of a proton with a divalent chain, having the other valence bonded to the free radical moiety. Hoever, major changes may be employed, as in the case of a polypeptide where only a portion of the polypeptide may be used for the ligand analog.

The linking group may be simply a single or multiple bond between the modified ligand moiety and the free radical moiety, but will normally be of at least one carbon or heteroatom.

The free radical moiety is conveniently a stable free radical, usually a nitroxide group and usually an $\alpha,\alpha,\alpha',\alpha'$-tetrasubstituted cyclic nitroxide group.

Ligand

Any ligand may be employed which is of biological interest and for which an appropriate receptor may be found having satisfactory specificity for the ligand. The recent literature contains an increasing number of reports of receptors for an increasingly wide variety of biologically active materials. Compounds for which receptors can be provided range from simple phenylalkylamines, e.g., amphetamine, to polymers, e.g., polypeptides and polysaccharides.

The ligands will include such compounds which are narcotics, hypnotics, sedatives, analgesics, antipyretics, anaesthetics, psychotogenic drugs, muscle relaxants, nervous system stimulants, anticholinesterase agents, parasympathomimetic agents, sympathomimetic agents, $\alpha$-andrenergic blocking agents, antiandrenergic agents, ganglionic stimulating and blocking agents, neuromuscular blocking agents, histamines, antihistamines, 5-hydroxytryptamine and antagonists; cardiovascular drugs, antiarrhythmic drugs, antihypertensive agents, vasodilator drugs, diuretics, pesticides (fungicides, antihelminthics, insecticides, ectoparasiticides, etc.) antimalarial drugs, antibiotics antimetabolites, hormones, vitamins, sugars, thyroid and antithyroid drugs, corticosteroids, insulin and oral hypoglemic drugs, and their metabolites.

Included among such drugs and agents are alkaloids, seroids, polypeptides, prostaglandins, catecholamines, xanthines, arylalkylamines, heterocyclics, e.g., thiazines, piperazines, indoles, and thiazoles; amino acids, etc.

Broadly, the ligands will be organic compounds, of from about 100 to 70,000 molecular weight, usually of from about 125 to 40,000 molecular weight, and more usually of from about 125 to 20,000 molecular weight.

A substantial portion of the ligands will be monomers, or low order polymers, usually drugs, hormones and the like, which will have molecular weights in the range of about 100 to 2,000, usually 125 to 1,000. Another significant portion of the ligands will be polymers (compounds with recurring units) which will have molecular weights in the range of from about 750 to 70,000, frequently from 1,000 to 40,000, and usually from 2,000 to 30,000. For polymers of varying molecular weight, weight average molecular weight is intended.

The ligands will normally be composed of carbon, hydrogen, nitrogen, oxygen, sulfur, phosphorous, halogen, and metals, primarily as their cations, such as the alkali and alkaline earth metals and the metals of Groups IB, IIB, VIIB, and VIIIB, particularly the third row of the periodic chart. Most usually, the ligands will be composed primarily of carbon, hydrogen, nitrogen, oxygen, and sulfur.

Structurally, the ligands may be monomers or polymers, acyclic, mono or polycyclic, having carbocyclic or heterocyclic rings. The ligands will have a wide variety of functionalities, such as halo, oxocarbonyl, nonoxocarobnyl, amino, oxy (hydroxy, aryloxy, alyloxy and cycloalyloxy ["alyl" intends a monovalent aliphatic radical], thiooxy, dithio, hydrazo, and combinations thereof.

The most important body of ligands for the purposes of the invention are the haptens. "Substances which on injection do not give rise to antibodies, but which are able to react with antibodies specifically to produce either precipitation or to inhibit precipitation have been termed haptens. This definition has been used to include not only the simple chemical substances which are determinants of specificity when conjugated to protein, and which inhibit precipitation, but also substances obtained from natural sources such as the pneumococcal type specific polysacchrides and dextran which are not antigenic in the rabbit on primary injection." Kabat, et al., Experimental Immunochemistry, Charles C. Thomas, Springfield, Illinois (1967). In the following discussion the term hapten will be confined to non-antigenic groups artificially introduced into proteins which affect specificity and will apply to these groups regardless of whether the group is attached to the protein.

Another group of ligands are those which have naturally occurring receptors. The receptors may be proteins, nucleic acids, such as ribonucleic acid (RNA) or deoxyribonucleic acid (DNA), or membranes associated with cells. Illustrative ligands which have naturally occurring receptors are thyroxine, many steroids, such as the estrogens, cortisone, corticosterone, and estradiol; polypeptides such as insulin and angiotensin II, as well as other naturally occurring biologically active compounds. See Murphy, et al., J. Clin. Endocr., 24, 187 (1964); Murphy, ibid, 27, 973 (1967); ibid, 28, 343 (1968); BBA, 176, 626 (1969); McEwen, et al., Nature, 226, 263 (1970); and Morgan et al, Diabetes, (1966); Page et al., J. Clin. Endocr. 28, 200, (1969).

The ligands may also be categorized by the chemical families which have become accepted in the literature. In some cases, included in the family for the purpose of this invention, will be those physiomimetic substances which are similar in structure to a part of the naturally occurring structure and either mimic or inhibit the physiological properties of the natural substance. Also, groups of synthetic substances will be included, such as the barbiturates and amphetamines. In addition, any of these compounds may be modified for linking to the free radical moiety. These modified compounds are referred to as ligand counterfeits.

A general category of ligands of particular interest are drugs and chemically altered compounds, as well as the metabolites of such compounds. The interest in assaying for drugs varies widely, from detrmining whether individuals have been taking a specific illicit drug, or have such drug in their possession to determining what drug has been administered or the concentration of the drug in a specific biological fluid.

The drugs are normally of from eight carbon atoms to thirty-five carbon atoms, usually of from nine to twenty-six carbon atoms and from one to ten heteroatoms, usually oxygen, nitrogen or sulfur.

One class of drugs have the following basic functionality:

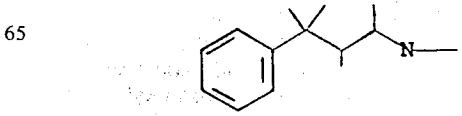

where the lines intended a bond to a carbon atom, and wherein any of the carbon atoms and the nitrogen atom may be bonded to hydrogen, carbon or a heterofunctionality. Drugs which have this basic structure include the opiates such as morphine and heroin, meperidine, and methadone.

Another class of drugs are the epinephrine like drugs which have the following basic functionality:

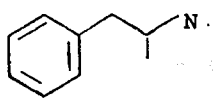

where the lines intend a bond to a carbon atom and wherein any of the carbon atoms and the nitrogen atom may be bonded to hydrogen, carbon or a heterofunctionality. Drugs which have this basic structure include amphetamine, narceine, epinephrine, ephedrine and L-dopa.

The ligand analogs of drugs will usually have molecular weights in the range of 275 to 1,000, more usually in the range of 300 to 700.

Drug ligand analogs
Opiates

The opiates are morphine alkaloids. All of these molecules have the following functionality and minimum structure:

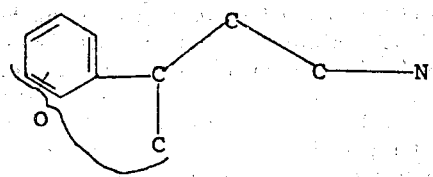

wherein the free valences are satisfied by a wide variety of groups, primarily carbon and hydrogen.

The free radical analog of these compounds will for the most part have the following minimum skeletal structure:

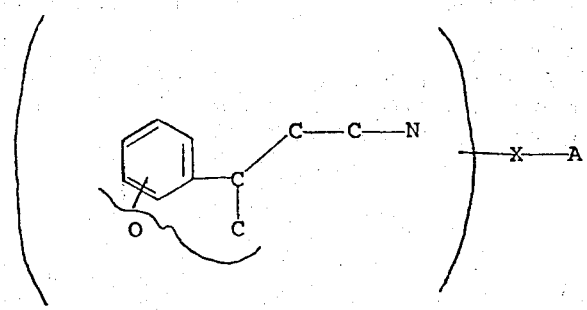

wherein X is a bond or a functionality such as imino, azo, oxy, thio, sulfonyl, oxocarbonyl, nnonoxocarbonyl, or combinations thereof. Oxygen will be in the ortho, meta or β position. A will usually be a heterocyclic compound of from 5 to 6 annular members, one of which annular member is a nitrogen of a nitroxide functionality, the other heteroannular member may be oxygen, sulfur or nitrogen. The nitrogen and sulfur may or may not be bonded to an oxygen atom. The ring will have from 0 to 1 site of ethylenic unsaturation. The various free radical groups will be dicussed subsequently.

The molecular weight of the compounds having the free radical substitutent will be at least about 350 and normally not exceeding 700, more usually in the range from about 400 to 600.

The free radical labeled morphine and its closely related analogs will have the following formula:

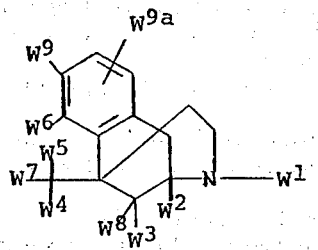

wherein:
any one of the W groups can be $-X^*-A^*$ or an H of any of the W groups may be replaced by $-X^*-A^*$. $X^*-A^*$ will be defined subsequently (there is only one $-X^*-A^*$ per molecule);

$W^1$ is hydrogen or hydrocarbon of from one to eight carbon atoms, particularly alkyl of from one to three carbon atoms, and aralkyl, e.g., methyl and β-phenethyl;

$W^2$ is hydrogen;

$W^3$ is hydrogen;

$W^4$ is hydrogen or taken together with $W^3$ a divalent radical of from 3 to 6 carbon atoms and 0 to 2 oxygen atoms, forming a six membered carbocyclic ring with the carbon chain to which they are attached, e.g., propylene-1,3, 1-hydroxyprop-2-enylene-1,3, 1-hydroxypropylene-1,3, 1-acetoxypropylene-1,3, 1-acetoxyprop-2-enylene-1,3, 1-oxopropylene-1,3, 1-oxoprop-2-enylene-1,3;

$W^5$ is hydrogen or hydroxyl;

$W^6$ is hydrogen, hydroxyl or taken together with $W^5$ oxy (-O-);

$W^7$ is hydrogen or methyl;

$W^8$ is hydrogen or hydroxyl;

$W^9$ is hydrogen, hydroxy, acyloxy of from 1 to 3 carbon atoms, e.g., acetoxy, (acyloxy intends only carboxy), hydrocarbyloxy of from 1 to 3 carbon atoms, e.g., methoxy, ethoxy, 2-(N-morpholio)ethoxy, and glucuronyl; and $W^{9a}$ is hydrogen.

It is understood, that in all the formulas, except when a minimum or skeletal structure is indicated, unsatisfied valences are satisfied by hydrogen.

(Hydrocarbyl is an organic radical compound solely of hydrogen and carbon and may be saturated or unsaturated, aliphatic, alicyclic, aromatic or combinations thereof).

Preferred compounds have $W^1$, or $W^9$ as $-X^*-A^*$ or have $W^3$ and $W^4$ taken together to provide $A^*-X^*-CHCH_2CH_2-$ or $A^*-X^*-CH-CH-CH-$ The close morphine analogs will have the following formula:

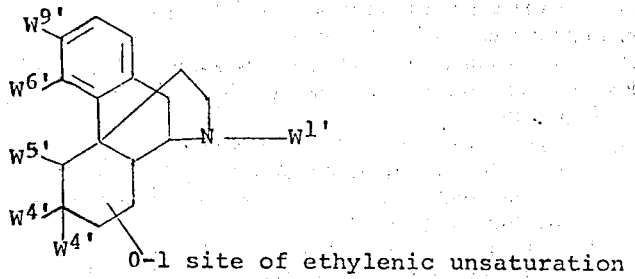

0-1 site of ethylenic unsaturation wherein:

any one of the W groups is —X*-A* or an H of any of the W groups can be replaced by —X*-A*. X*-A* will be defined subsequently (there is only one —X*-A* per molecule);

$W^{1'}$ is alkyl of from 1 to 3 carbon atoms, e.g., methyl;

$W^{4'}$ is hydrogen, hydroxy, or acetoxy (where two hydroxyls are on the same carbon atom, oxo is intended);

$W^{5'}$ is hydrogen or hydroxyl;

$W^{6'}$ is hyrogen, hydroxyl or taken together with $W^{5'}$ oxy (-O-); and $W^{9'}$ is hydoxy or alkoxy of from 1 to 3 carbon atoms.

Those compounds having the basic morphine structure will have the following formula:

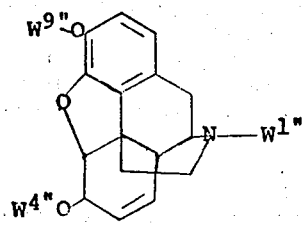

wherein:

one of $W^{1''}$ and $W^{9''}$ is —X*-A*; when other than —X*-A*

$W^{1''}$ is methyl; and $W^{9''}$ is hydrogen, methyl, or glucuronyl;

$W^{4''}$ is hydrogen or acetyl, usually hydrogen;

—X* is

wherein Z is hydrocarbylene of from 1 to 7 carbon atoms, preferably aliphatic, having from 0 to 1 site of ethylenic unsaturation; and A* is of the formula:

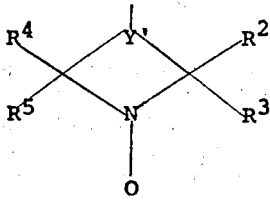

wherein $R^{2-5}$ is alkyl of from 1 to 3 carbon atoms and Y' is a trivalent radical of from 1 to 3 carbon atoms, usually of from 2 to 3 annular carbon atoms, and 0 to 1 heteroatoms.

Illustrative narcotics which can be linked to a free radical compound include morphine, heroin, hydromorphone, oxymorphone, metopon, codeine, hydrocodone, dihydrocodeine, dihydrohydroxycodeinone, pholcodine, dextromethorphan, phenazocine, dionin and their metabolites.

Illustrative compounds which may be bonded to a free radical compound iclude $O^3$-carboxymethylmorphine, N-(2'-carboxypropyl) $O^3$-methylnormoprhine, $O^3$-methyl, $O^7$-morphinyl succinate, 2-aza-2-(2''-phenylethyl)-5,9-dimethyl-6,7-(5'-carboxymethoxybenzo)bicyclo[3,3,1$^{1,5}$] oct-6-ene, $O^3$-ethyl, $O^7$-(3'-aza-5-chloropentyl)morphine, $O^7$-acetyl, $O^3$-carboxymethyl-morphine, 7,8-dihydro-14-hydroxymorphinone, O-carboxymethyl oxime, N-desmethyl N-carboxymethylmorphine, N-desmethylN-3-carboxypropylmorphine, $O^3$-(2'-aminoethyl) morphine and N-desmethyl N-(2-carboxyethyl) morphine.

It is to be understood that the various groups are chosen so as to relate to known compounds of physiological interest. The primary difference between the known compounds and the subject compounds is the linking group and the presence of the free radical moiety.

Methadone

Another group of compounds having narcotic acitivity is methadone and its analogs, which for the most part have the following formula:

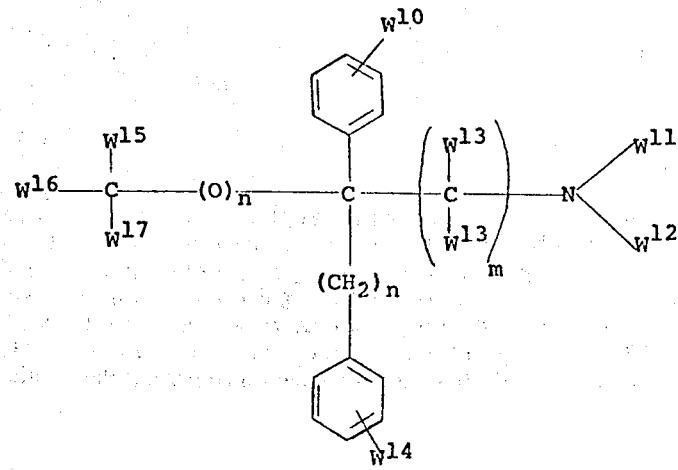

wherein:

any one of the W groups can be —X*-A* or an H of any of the W groups may be replaced by —X*-A*. X*-A* will be defined subsequently (there is only one —X*-A* per molecule);

$n$ is 0 or 1, usually being the same in both instances;
$m$ is 2 or 3;
$W^{10}$ is hydrogen;
$W^{11}$ and $W^{12}$ are hydrogen, alkyl of from 1 to 3 carbon atoms, e.g., methyl, or may be taken together to form a six-membered ring with the nitrogen atom to which they are attached, e.g., pentylene-1,5 and 3-oxapentylene-1,5;
$W^{13}$ is hydrogen or methyl, only one $W^{13}$ being methyl;
$W^{14}$ is hydrogen;
$W^{15}$ is hydrogen or hydroxyl;
$W^{16}$ is hydrogen, acyloxy of 1 to 3 carbon atoms, e.g., propionoxy, or hydroxy (when $W^{15}$ and $W^{16}$ are both hydroxy, the oxo group is intended), with the proviso that $W^{15}$ and $W^{16}$ are the same when $n$ equals 1; and
$W^{17}$ is hydrogen or alkyl of 1 to 3 carbon atoms, e.g., ethyl.

Illustrative compounds which can be marked with a free radical are methadone, dextromoramide, dipipanone, phenadoxone, propoxyphene (Darvon) and acetylmethadone.

Preferred compounds are when $W^{11}$ or $W^{17}$ is —X*-A*.

A narrower class of methadone and its analogs are of the formula:

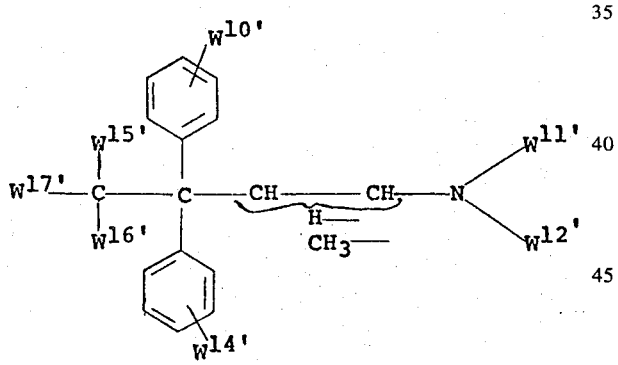

wherein:

any one of the W groups can be —X*-A* or an H of any of the W groups can be replaced by —X*-A*. X*-A* will be defined subsequently (there is only one —X*-A* per molecule);

$W^{10'}$ and $W^{14'}$ are hydrogen;
$W^{11'}$ and $W^{12'}$ are methyl or are taken together with the nitrogen atom to which they are attached to form a morpholino or piperidine ring;
$W^{15'}$ and $W^{16'}$ are hydrogen, hydroxy, acetoxy, at least one being hydroxy or acetoxy; and
$W^{17'}$ is alkyl of from 1 to 3 carbon atoms.

The methadone derivatives will for the most part have the following formula:

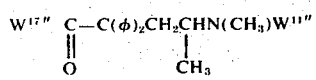

wherein one of $W^{11''}$ or $W^{17''}$ is -X*-A*; when other than X*-A*
$W^{11''}$ is methyl; and
$W^{17''}$ is propyl;
$\phi$ is phenyl;
X* is -ZCONH, wherein Z is hydrocarbylene of from 1 to 7 carbon atoms, preferably aliphatic, having from 0 to 1 site of ethylenic unsaturation; and
A* is of the formula:

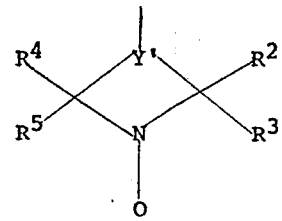

wherein $R^{2-5}$ and $Y'$ have been defined previously.

The metabolites of methadone and close analogs will for the most part have the following formula:

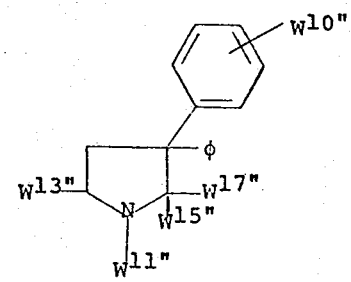

wherein:

any one of the W groups can be —X*-A* or an H of any of the W groups can be replaced by —X*-A*. X*-A* will be defined subsequently (there is only one —X*-A* per molecule);

$\phi$ is phenyl;
$W^{10''}$ is hydrogen;
$W^{11''}$ is hydrogen, methyl, or a free valence joined with $W^{15''}$ ;
$W^{13''}$ is hydrogen or methyl;
$W^{15''}$ is hydrogen, hydroxy, or taken together with $W^{11''}$ forms a double bond between the nitrogen atom and the carbon atom to which $W^{11''}$ and $W^{15''}$ are respectively attached; and
$W^{17''}$ is alkyl of from one to three carbon atoms, usually two carbon atoms.

Illustrative compounds which may be linked to a free radical compound include phenylbenzyl(1-dimethylamino-2-propyl)-methyl succinate, phenylbenzyl(1-dimethylamino-2-propyl)methyl oxalate, diphenyl(2-dimethylamino-1-propyl)methyl maleate, O-carboxymethyl 4,4-diphenyl-7-dimethylamino-2-heptanone-oxime, 4,4-diphenyl-7-dimethylamino-3-octyl succinate, N-(2,2-diphenyl-3-methyl-4-morpholinobutyryl)glycine, 3-ethyl-4,4-diphenyl-6-dimethylamino-hept-2-enoic acid, 6-keto-7,7-diphenyl-9- diphenyl-9-(dimethylamino)decanoic acid, N-carboxymethyl 2-ethyl-3,3-diphenyl-5-methylpyrrolidine.
Meperidine The third group of compounds which have narcotic acitivity and are meperidine or meperidine analogs, have for the most part, the following formula:

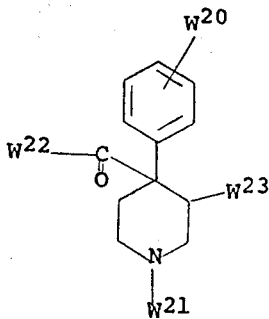

wherein:

any one of the W groups can be —X*-A* or an H of any of the W groups may be replaced by —X*-A*. X*-A* will be defined subsequently (there is only one —X*-A* per molecule);

$W^{20}$ is hydrogen;

$W^{21}$ is hydrogen, alkyl of from 1 to 3 carbon atoms, e.g., methyl, aminophenylalkyl, e.g., β-(p-aminophenyl)ethyl, or phenylaminoalkyl, e.g., phenylaminopropyl, (alkyl of from 2 to 3 carbon atoms);

$W^{22}$ is alkoxy of from 1 to 3 carbon atoms, e.g., ethoxy; and $W^{23}$ is hydrogen or methyl.

Illustrative compounds are meperidine, alphaprodine, alvodine and anileridine.

Preferred compounds are those where $W^{21}$ or $W^{22}$ is -X*-A* or a hydrogen of $W^{21}$ is replaced with -X*-A*.

Indole Alkaloids

A second group of ligands of interest are based on tryptamine and come within the class of indole alkaloids, more specifically ergot alkaloids. These compounds will have the following minimal structure:

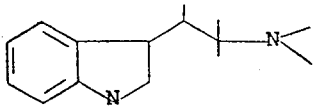

wherein the free valences are satisfied by a variety of groups, primarily carbon and hydrogen, although other substituents may be present such as carboxyl groups, hydroxyl groups, keto groups, etc. The most common member of this class which finds use is lysergic acid, primarily as its diethylamide. Other members of the indole alkaloid family which can also be assayed for are the strychnine group and the indolopyridocoline group, which finds yohimbine and reserpine as members.

The free radical substituted indole alkaloids will have the following formula:

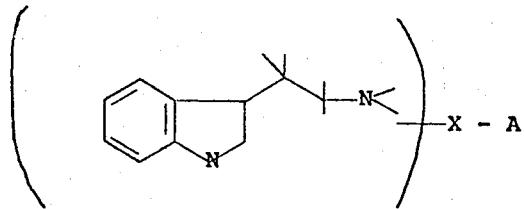

wherein X and A have been defined previously.

Other groups of alkaloids include the steroid alkaloids, the iminazolyl alkaloids, the quinazoline alkaloids, the isoquinoline alkaloids, the quinoline alkaloids, quinine being the most common, and the diterpene alkaloids.

For the most part, the alkaloids bonded to a free radical functionality will be of from about 300 to 1,500 molecular weight, more usually of from about 400 to 1,000 molecular weight. They are normally solely composed of carbon, hydrogen, oxygen, nitrogen and sulfur, sulfur being present in the free radical group; the oxygen is present as oxy and oxo and the nitrogen present as amino or amido. Of course, with the nitroxide radical, a nitrogen and oxygen will be present together as that functionality.

Catecholamines

The first group in this category are catecholamines of the formula:

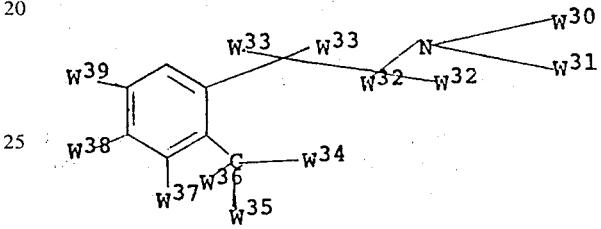

wherein:

any one of the W groups can be —X*-A* or an H of any of the W groups may be replaced by —X*-A*. X*-A* will be defined subsequently (there is only one —X*-A* per molecule);

$W^{30}$ is hydrogen or alkyl of from 1 to 3 carbon atoms, e.g., methyl;

$W^{31}$ is hydrogen, or alkyl of from 1 to 3 carbon atoms, e.g., methyl;

$W^{32}$ and $W^{33}$ are hydrogen;

$W^{34}$ is hydrogen, hydroxy, dimethoxycarboxyphenacyl, and dimethoxy-α-phthalidyl;

$W^{35}$ and $W^{36}$ are hydrogen, one of which may be taken with $W^{31}$ to form a bond, and when $W^{31}$ and $W^{35}$ are taken together, each of $W^{32}$ and $W^{33}$, and $W^{30}$ and $W^{36}$, may be taken together to form a double bond;

$W^{37}$ is hydrogen or alkoxy of from 1 to 3 carbon atoms; e.g., methoxy;

$W^{38}$ and $W^{39}$ are hydroxy or alkoxy of from 1 to 3 carbon atoms, e.g., methoxy.

Illustrative compounds include cotainine, narceine, noscapine and papaverine.

Preferred compounds are where $W^{30}$, $W^{38}$ or $W^{39}$ are —X*-A* or have a hydrogen replaced with -X*-A*.

Another group of catecholamines or analogs are epinephrine, amphetamines and related compounds. These compounds have the formula:

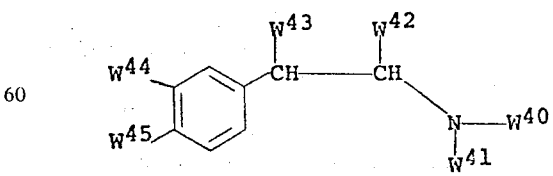

wherein:

any one of the W groups can be —X*-A* or an H of any of the W groups may be replaced by -X*-A*. X*-A* will be defined subsequently (there is only one —X*-A* per molecule);

$W^{40}$ and $W^{41}$ are hydrogen or alkyl of from 1 to 3 carbon atoms, e.g., methyl and isopropyl, preferably one is hydrogen;

$W^{42}$ is hydrogen, alkyl of from 1 to 3 carbon atoms, e.g., methyl and ethyl, or carboxy;

$W^{43}$ is hydrogen or hydroxyl; and $W^{44}$ and $W^{45}$ are hydrogen, hydroxyl or alkoxyl of from 1 to 3 carbon atoms.

Illustrative compounds which can be spin labeled are ephedrine, epinephrine, L-dopa, cohefrine, benzidrine (amphetamine), paredrine, methamphetamine and norephedrine.

Illustrative compounds which can be linked to a free radical compound include 3-(3',4'-dihydroxyphenyl)-3-hydroxypropionic acid, N-(β-(β,3,4-trihydroxyphen)ethyl) N-methyl glycine, N-(1-phenyl-2-propyl) N-methyl glycine, N-(1-phenyl-2-propyl)oxalamic acid, O-(1-phenyl-2-methylamino-1-propyl)glycolic acid, p-(2-methylaminopropyl-1)phenoxyacetic acid, N-(1'-phenyl-2'-propyl) glycine, 4-methylamino-4-phenylvaleric acid, para-(2-aminopropyl-1)phenoxyacetic acid, 4-methylamino-5-phenylvaleric acid, and 3-amino-4-phenylbutyric acid.

Where $W^{44}$ and $W^{45}$ are hydrogen, preferred compounds will have the following formula:

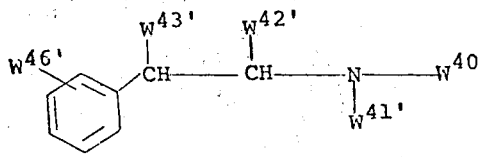

wherein:

any one of the W groups can be $-X^*-A^*$ or an H of any of the W groups may be replaced by $-X^*-A^*$. $X^*-A^*$ will be defined subsequently (there is only one $-X^*-A^*$ per molecule);

$W^{40'}$ and $W^{41'}$ are hydrogen or alkyl of from 1 to 3 carbon atoms, preferably one is hydrogen;

$W^{42'}$ is hydrogen or methyl;

$W^{43'}$ is hydrogen or hydroxyl; and $W^{46'}$ is hydrogen.

Where $W^{44}$ and $W^{45}$ are oxy, the preferred compounds have the following formula:

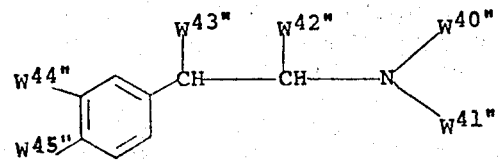

wherein:

any one of the W groups can be $-X^*-A^*$ or an H of any of the W groups may be replaced by $-X^*-A^*$. $X^*-A^*$ will be defined subsequently (there is only one $-X^*-A^*$ per molecule);

$W^{40''}$, $W^{41''}$, and $W^{42''}$ are hydrogen or methyl;

$W^{43''}$ is hydrogen or hydroxyl; and $W^{44''}$ and $W^{45''}$ are hydroxyl or methoxyl.

Closely related compounds to the amphetamines are those where a saturated five or six membered ring is substituted for the phenyl ring. These compounds will have the following formula:

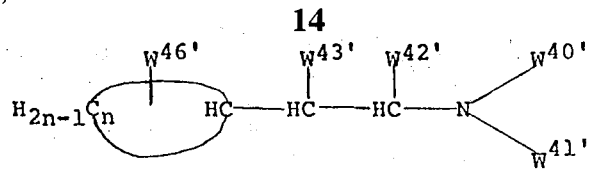

wherein:

any one of the W groups is $-X^*-A^*$ or an H of any of the W groups may be replaced by $-X^*-A^*$. $X^*-A^*$ will be defined subsequently (there is only one $-X^*-A^*$ per molecule);

$W^{40'}-^{43'}$ have been defined above;

$W^{46'}$ is hydrogen; and n is an integer of from four to five.

Of particular interest are those spin labeled amphetamines of the following formula:

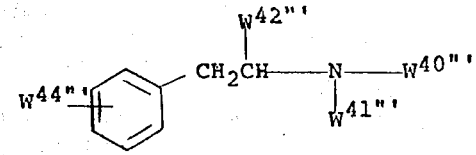

wherein one of $W^{40'''}$, $W^{42'''}$, and $W^{44'''}$ is $-X^*-A^*$; when other than $-X^*-A^*$;

$W^{40'''}$ is hydrogen;

$W^{42'''}$ is methyl; and $W^{44'''}$ is hydrogen;

$W^{41'''}$ is hydrogen or methyl;

$X^*$ is $-Z-CONH-$, wherein Z is hydrocarbylene of from 1 to 7 carbon atoms, usually aliphatic, having from 0 to 1 site of ethylenic unsaturation, with the proviso that when $W^{44'''}$ is $-X^*-A^*$, $-X^*$ is $-O-Z-CONH-$; and $A^*$ is of the formula:

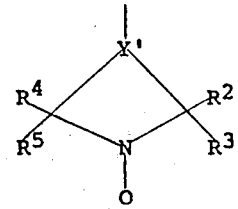

wherein $R^{2-5}$ and $Y'$ have been defined previously.

Barbiturates

A wide class of synthetic drugs which finds extensive and frequent abuse are the barbiturates. These compounds are synthetically readily accessible and their use only difficulty policed. The compounds which find use will come within the following formula:

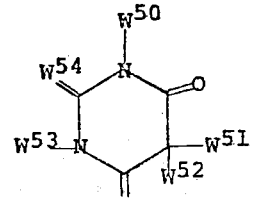

wherein:

any one of the W groups can be $-X^*-A^*$ or an H of any of the W groups may be replaced by $-X^*-A^*$. $X^*-A^*$ will be defined subsequently (there is only one $-X^*-A^*$ per molecule);

$W^{50}$ is hydrogen, alkyl of from 1 to 3 carbon atoms, e.g., methyl or alkali metal, e.g., sodium;

$W^{51}$ and $W^{52}$ are hydrogen, alkyl, alkenyl, cycloalkyl, cycloalkenyl, or aryl hydrocarbon of from 1 to 8, more usually 1 to 6 carbon atoms, e.g., ethyl, n-butyl, α-methylbutyl, isoamyl, allyl, $\Delta^1$-cyclohexenyl, and phenyl;

$W^{53}$ is hydrogen, or alkali metal, e.g., sodium;

$W^{54}$ is oxygen or sulfur.

Illustrative compounds which may be spin labeled are veronal, medinal, luminal, prominal, soneryl, nembutal, amytal, dial, phenadorn, seconal, evipan, phenobarbital and pentothal.

Preferred compounds would have $W^{50}$ or $W^{51}$ or a hydrogen of $W^{50}$ or $W^{51}$ as —X*-A*. Also preferred is when one of $W^{51}$ and $W^{52}$ is hydrocarbyl of from 2 to 8 carbon atoms.

Illustrative compounds which may be linked to a free radical compound include 5,5-diethyl-1-carboxymethylbarbituric acid, 5-ethyl-5-n-butyl-1-succinoylbarbituric acid, 5-ethyl-5-phenyl-1-(N'-(2'''-chloroethyl)-2''-aminoethyl)barbituric acid, 5-(2'-carboxy-$\Delta^{1'2'}$-cyclohexenyl)-1,5-dimethylbarbituric acid, N-carboxymethyl phenobarbital, 5-(γ-crotonic acid)-5-(2'-pentyl)barbituric acid, 5-(p-aminophenyl)-5-ethylbarbituric acid, 5-(5'-pentanoic acid)-5-(2'-pentyl)barbituric acid, and 1-methyl-5-ethyl-5-(p-carboxyphenyl)barbituric acid.

Of particular interest are those spin labeled barbiturates of the formula:

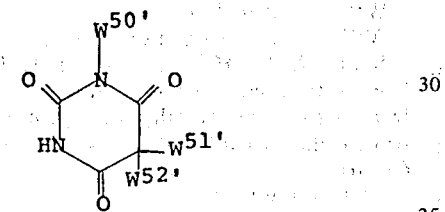

wherein one of $W^{50'}$ and $W^{51'}$ is -X*-A*; when other than -X*-A*:

$W^{50'}$ is hydrogen, methyl or alkali metal, e.g., sodio; and $W^{51'}$ is hydrocarbon of from 1 to 8 carbon atoms, having from 0 to 1 site of ethylenic unsaturation;

$W^{52'}$ is hydrocarbon of from 2 to 8 carbon atoms, having from 0 to 1 site of ethylenic unsaturation;

X* is -Z-CONH, wherein Z is hydrocarbylene of from 1 to 7 carbon atoms, usually aliphatic, having from 0 to 1 site of ethylenic unsaturation; and A* is of the formula:

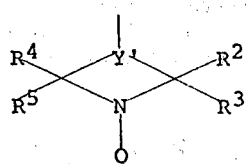

wherein $R^{2-5}$ and Y' have been defined previously.

Glutethimide

Another compound of interest is glutethimide, wherein the free radical analog will have the following formula:

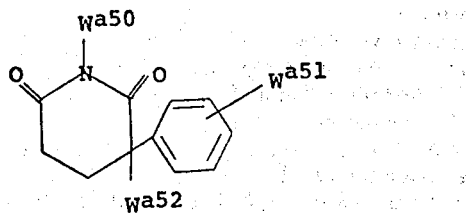

wherein:

any one of the W groups can be —X*-A* or an H of any of the W groups may be replaced by —X*-A*.

X*-A* will be defined subsequently (there is only one —X*-A* per molecule);

$W^{a50}$ and $W^{a51}$ are hydrogen; and $W^{a52}$ is lower alkyl of from 1 to 3 carbon atoms, e.g., ethyl.

Cocaine

A drug of significant importance in its amount of use is cocaine. The free radical labeled cocaine or cocaine metabolites or analogs, such as ecgonine, will for the most part have the following formula:

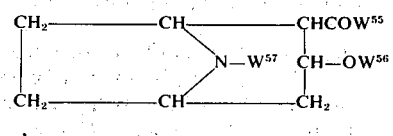

wherein:

any one of the W groups can be —X*-A* or an H of any of the W groups may be replaced by —X*-A . X*-A* will be defined subsequently (there is only one —X*-A* per molecule);

$W^{55}$ is hydroxy, methoxy and amino;

$W^{56}$ is hydrogen or benzoyl; and $W^{57}$ is hydrogen or alkyl of from 1 to 3 carbon atoms, e.g., methyl.

Of particular interest are those ecgonine derivatives (including cocaine derivatives) of the formula:

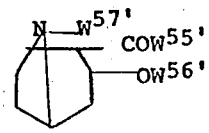

wherein one of $W^{56'}$ and $W^{57'}$ is -X*-A*; when other than X*-A*:

$W^{56'}$ is hydrogen or benzoyl; and $W^{57'}$ is methyl;

$W^{55'}$ is hydroxy or methoxy;

X* is

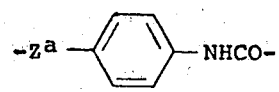

wherein $Z^a$ is methylene or carbonyl, or

—Z—CONH— wherein Z is hydrocarbylene of from 1 to 7 carbon atoms, usually aliphatic, having from 0 to 1 site of ethylenic unsaturation; and A* is of the formula:

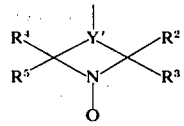

wherein $R^{2-5}$ and Y' have been defined previously.

Diphenyl Hydantoin

Another compound of interest is the antiepileptic drug diphenyl hydantoin. This compound and its analogs will have the following formula:

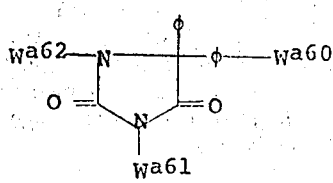

wherein:

any one of the W groups can be —X*-A* or an H of any of the W groups may be replaced by —X*-A* will be defined subsequently (there is only one —X*-A* per molecule);

φ is phenyl;

$W^{a60}$, $W^{a61}$ and $W^{a62}$ are hydrogen.

Marijuana

Because of its ready availability and widespread use, tetrahydrocannabinol (the active ingredient of marijuana) and its cogeners, cannabidiol and cannabinol and their metabolites are compounds of great interest, where a simple assay method would be of importance. The compounds which find use as analogs have the following formula:

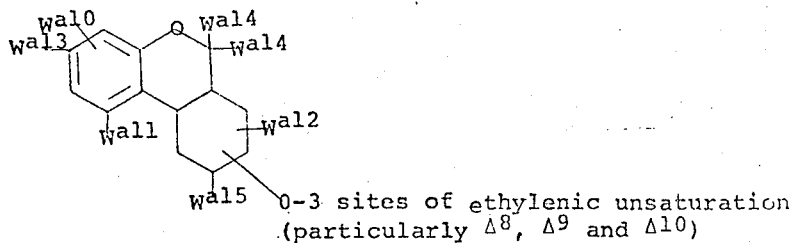

0-3 sites of ethylenic unsaturation (particularly $\Delta^8$, $\Delta^9$ and $\Delta^{10}$)

wherein:

any one of the W groups can be —X*-A* or an H of any of the W groups can be replaced by -X*-A*. X*-A* will be defined subsequently (there is only one -X*-A* per molecule);

$W^{a10}$ is hydrogen or carboxyl;

$W^{a11}$ is hydroxyl or methoxyl;

$W^{a12}$ is hydrogen;

$W^{a13}$ is pentyl or hydroxypentyl;

$W^{a14}$ is hydrogen, methyl, or the two $W^{a14}$'s may be taken together to form a carbocyclic ring of from 4 to 6 annular members; and $W^{a15}$ is methyl, hydroxymethyl or carboxyl.

Tranquilizers

A number of compounds have tranquilizer effects and because of their misuse or abuse do provide opportunities where the determination could be of use.

The first tranquilizer of interest is Meprobamate, also known as Miltown or Equanil. This compound and related analogs have the following formula:

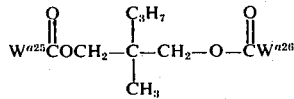

wherein:

any one of the W groups can be —X*-A* or an H of any of the W groups may be replaced by —X*-A*. X*-A* will be defined subsequently (there is only one —X*-A* per molecule);

$W^{a25}$ and $W^{a26}$ are amino.

The next group of tranquilizers are benzdiazocycloheptanes and are known as Librium, Valium, Diazepam, or Oxazepam. These compounds and their related analogs will have the following formula:

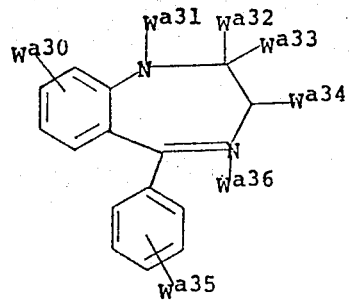

wherein:

any one of the W groups can be -X*-A* or an H of any of the W groups may be replaced by —X*-A*. X*-A* will be defined subsequently (there is only one —X*-A* per molecule);

$W^{a30}$ and $W^{a35}$ are hydrogen;

$W^{a31}$ is hydrogen, lower alkyl of from 1 to 3 carbon atoms, e.g., methyl, or may be taken together with $W^{a32}$ to form a double bond between the carbon and the nitrogen;

$W^{a33}$ is amino or lower alkylamino of from 1 to 3 carbon atoms, e.g., methylamino, or may be taken together with $W^{a32}$ to form a carbonyl;

$W^{a34}$ is hydrogen or hydroxyl; and $W^{a36}$ is oxy or an unshared pair of electrons.

The next group of compounds are the phenothiazines of which chlorpromazine is a member. These compounds will for the most part have the following formula:

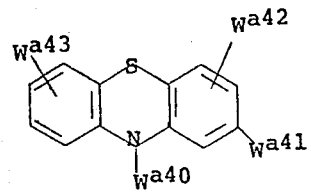

wherein:

$W^{a40}$ is hydrogen, alkyl of from 1 to 6 carbon atoms, dialkylaminoalkyl of from 4 to 8 carbon atoms, e.g., 3-(dimethylamino)propyl; N-hydroxyalkyl (alkyl of from 2 to 3 carbon atoms), N'-piperazinoalkyl (alkyl of from 2 to 3 carbon atoms), e.g., N-hydroxyethyl N'-piperazinopropyl; N-alkyl (alkyl of from 1 to 3 carbon atoms) N'-piperazinoalkyl (alkyl of from 2 to 3 carbon atoms), e.g., N-methyl N'-piperazinopropyl; and 2-(N-alkyl)-piperidinoalkyl, wherein the N-alkyl is of from 1 to 3 carbon atoms and the other alkyl is of from 2 to 3 carbon atoms, e.g., 2-(N-methyl)-piperidinoethyl, there being at least two carbon atoms between the heteroatoms;

$W^{a41}$ is hydrogen, chloro, trifluoromethyl, alkylmercapto of from 1 to 3 carbon atoms, e.g., methylmercapto and acyl of from 1 to 3 carbon atoms, e.g., acetyl; and $W^{a42}$ and $W^{a43}$ are hydrogen.

Amino Acids, Polypeptides and Proteins

The next group of compounds are the amino acids, polypeptides and proteins. For the most part, the amino acids range in carbon content from 2 to 14 carbon atoms, and include a variety of functional groups such as mercapto, dithio, hydroxyl, amino, guanidyl, pyrrolidinyl, indolyol, imidazolyl, methylthio, iodo, diphenylether, hydroxyphenyl, etc. These, of course, are primarily the amino acids related to humans, there being other amino acids found in plants and animals.

Polypeptides usually encompass from about 2 to 100 amino acid units (usually less than about 12,000 molecular weight). Larger polypeptides are arbitrarily called proteins. Proteins are usually composed of from 1 to 20 polypeptide chains, called subunits, which are associated by covalent or non-covalent bonds. Subunits are normally of from about 100 to 300 amino acid groups (~10,000 to 35,000 molecular weight).

Individual polypeptides and protein subunits will normally have from about 2 to 300, more usually from about 2 to 150 recurring amino acid groups. Usually, the polypeptides and protein subunits of interest will be not more than about 20,000 molecular weight and greater than about 750 molecular weight. Any of the amino acids may be used in preparing the polypeptide. Because of the wide variety of functional groups which are present in the amino acids and frequently present in the various naturally occurring polypeptides, the free radical compound can be bonded to any convenient functionality. Usually, the free radical compound can be bonded to a cysteine, lysine or arginine group, although serine, threonine, or any other amino acid with a convenient functionality, e.g., carboxy and hydroxy, may be used.

For the most part, the spin labeled polypeptides will have the following formula:

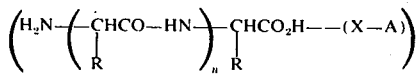

wherein X and A have been defined previously, and R is an amino acid residue, n being an integer of from 1 to 700, more usually of from 1 to 200, and most commonly of from 2 to 100.

Illustrative amino acids include glycine, alanine, serine, histidine, methionine, hydroxyproline, tryptophan, tyrosine, thyroxine, ornithine, phenylalanine, arginine, and lysine. Polypeptides of interest are ACTH, oxytocin, lutenizing hormone, insulin, Bence-Jones protein, chorionic gonadotropin, pituitary gonadotropin, growth hormone, renin, thyroxide bonding globulin, bradykinin, angiotensin, follicle stimulating hormone, etc.

In many instances, it will be desirable to digest a protein and assay for the small polypeptide fragments. The concentration of the fragment may then be related to the amount of the original protein.

Steroids

Another important group of compounds which find use in this invention are the steroids, which have a wide range of functionalities depending on their function in the body. In addition to the steroids, are the steroidmimetic substances, which while not having the basic polycyclic structure of the steroid, do provide some of the same physiological effects.

The steroids have been extensively studied and derivatives prepared which have been bonded to antigenic proteins for the preparation of antibodies to the steroids. Illustrative compounds include: 17β-estradiol-6-(O-carboxymethyl-oxime)-BSA (bovine serum albumin) (Exley, et al, Steroids 18, 593, (1971); testosterone-3-oxime derivative of BSA (Midgley, et al, Acta Endocr. 64, supplement 147, 320 (1970)); and progesterone-3-oxime derivative of BSA (Midgley, et al., ibid.)

For the most part, the steroids used have the following structure:

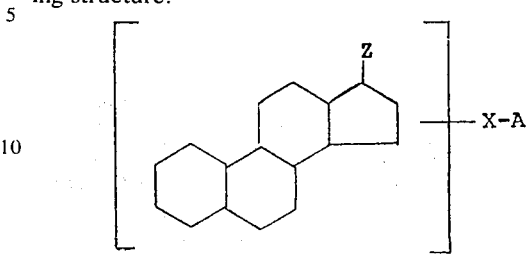

wherein X and A have been defined previously. Usually, the free radical compound will be bonded to the A, B, or C rings, at the 2,3,4,6, or 11 positions, or at the 16 or 17 position of the D ring or on the side chains at the 17 position. The rings may have various substituents, particularly methyl groups, hydroxyl groups, oxocarbonyl groups, ether groups, and amino groups. Any of these groups may be used to bond the free radical compound to the basic ring structure. For the most part, the steroids of interest will have at least one, usually 1 to 6, more usually 1 to 4 oxygen functionalities, e.g., alcohol, ether, esters, or keto. In addition, halo substituents may be present. The steroids will usually have from 18 to 27 carbon atoms.

The rings may have one or more sites of unsaturation, either ethylenic or aromatic and may be substituted at positions such as the 6,7 and 11 positions with oxygen substituents. In addition, there may be methyl groups at the 10 and 13 positions. The position marked with a Z, 17, may be and will be varied widely depending on the particular steroid. Z represents two monovalent groups or one divalent group and may be a carbonyl oxygen, an hydroxy group, an aliphatic group of from 1 to 8 carbon atoms, including an acetyl group, an hydroxyacetyl group, carboxy or carboxyalkyl of from 2 to 6 carbon atoms, an acetylenic group of from 2 to 6 carbon atoms or halo substituted alkyl or oxygenated alkyl groups, or a group having more than one functionality, usually from 1 to 3 functionalities.

For Z, there may be one H or a second group, particularly hydroxyl; alkyl, e.g., methyl; hydroxylalkyl, e.g., hydroxymethyl; halo, e.g., fluoro or chloro, oxyether; and the like.

These steroids find use as hormones, male and female (sex) hormones, which may be divided into oestrogens, gestogens, androgens, andrenocortical hormones (glucocorticoids), bile acids, cardiotonic glycosides and aglycones, as well as saponins and sapogenins.

Steroid mimetic substances, particularly sex hormones are illustrated by diethyl stilbestrol.

The sex hormones of interest may be divided into two groups; the male hormones (androgens) and the female hormones (oestrogens).

The androgens which find use will have the following formula:

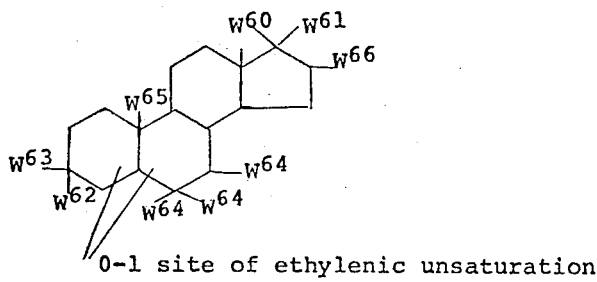

0-1 site of ethylenic unsaturation wherein:

any one of the W groups can be —X*-A* or an H of any of the W groups may be replaced by —X*-A*. X*-A* will be defined subsequently (there is only one —X*-A* per molcule);

$W^{60}$ is hydrogen, or hydroxyl;

$W^{61}$ is hydrogen, methyl or hydroxyl (when two groups bonded to the same carbon atom are hydroxyl, oxo is intended);

$W^{62}$ and $W^{63}$ are hydrogen or hydroxyl, at least one of $W^{60-63}$ is hydroxy (either as hydroxy or oxo);

$W^{64}$ is hydrogen, or two $W^{64}$'s may be taken together to form a double bond;

$W^{65}$ is methyl; and $W^{66}$ is hydrogen.

Illustrative compounds which may be bonded to a free radical compound include testosterone, androsterone, isoandrosterone, etiocholanolone, methyltestosterone and dehydroisoandrosterone.

Illustrative compounds which may be linked to a free radical compound include N-carboxymethoxy testosteroneimine, 17-monotestosteronyl carbonate, androsteronyl succinate, testosteronyl maleate, $O^3$-carboxymethyl $O^{17}$-methyl androst-5-ene-3$\beta$, 17$\beta$-diol, testosterone O-carboxymethyl oxime and androsteronyl carbonate.

The estrogens have an aromatic A ring and for the most part have the following formula:

wherein:

any one of the W groups can be —X*-A* or an H of any of the W groups may be replaced by —X*-A*. X*-A* will be defined subsequently (there is only one —X*-A* per molecule);

$W^{70}$ or $W^{71}$ is hydrogen, ethinyl or hydroxyl (when two hydroxyls are bonded to the same carbon atoms, oxo is intended);

$W^{72}$ is hydrogen or hydroxyl;

$W^{73}$ is hydroxyl or alkoxyl of from 1 to 3 carbon atoms;

$W^{74}$ is hydrogen or two $W^{74}$'s may be taken together to form a double bond; and $W^{75}$ is hydrogen.

Illustrative compounds which may be bonded to a free radical compound are equilenin, $\beta$-estradiol, estrone, estriol and 17-$\alpha$-ethinyl-estradiol.

Illustrative compounds which may be bonded to a free radical compound include 3-carboxymethyl estradiol, 2-chloromethylestrone, estrone glutarate, O-carboxymethyloxime of 6-ketoestradiol, equilenyl aspartate, estrone O-carboxymethyl oxime and equileninyl N-carboxymethyl thiocarbamate.

Another class of hormones are the gestogens which have the following formula:

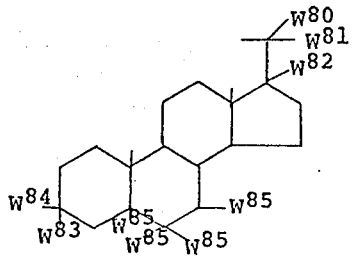

wherein:

any one of the W groups can be —X*-A* or an H of any of the W groups may be replaced by —X*-A*. X*-A* will be defined subsequently (there is only one —X*-A* per molecule);

$W^{80}$ and $W^{81}$ are hydrogen or hydroxyl, at least one being hydroxyl (where two hydroxyl groups are bonded to the same carbon atom, oxo is intended);

$W^{82}$ is hydrogen or hydroxyl;

$W^{83}$ and $W^{84}$ are hydrogen or hydroxyl, at least one being hydroxyl; and $W^{85}$ is hydrogen or two $W^{85}$'s may be taken together to form a double bond.

Illustrative compounds which may be bonded to a free radical compound include progesterone, pregnenolone, allopregnane-3a:20a-diol and allopreganan-3a-ol-20-one.

Illustrative compounds which may be linked to a free radical compound include 20-progesterone O-carboxymethyl oxime, pregn-4-en-20-on-3-ylidinylmethylenecarboxylic acid, O-carboxymethyl progesterone 3-oxime, pregnenolonyl tartrate, O-pregnenolonyl tartrate, O-pregnenolonyl lactic acid, allopreganane-3-carboxymethyl-20-ol.

The next important groups of steroids are the corticosteroids which include both the mineralcorticoids and the glucocorticoids. These compounds have the following formula:

0-1 site of ethylenic unsaturation wherein:

any one of the W groups can be —X*-A* or an H of any of the W groups may be replaced by —X*-A*. X*-A* will be defined subsequently (there is only one —X*-A* per molecule);

$W^{90}$ is hydrogen or hydroxyl;

$W^{91}$ and $W^{92}$ are hydrogen or hydroxyl, at least one of which is hydroxyl (when two hydroxyl groups are bonded to the same carbon atom, oxo is intended);

$W^{93}$ is hydrogen or hydroxyl;

$W^{94}$, $W^{95}$, $W^{96}$, and $W^{97}$ are hydrogen or hydroxyl, at least one of $W^{94}$ and $W^{95}$ is hydroxyl;

$W^{98}$ is methyl or formyl; and $W^{99}$ is hydrogen or two $W^{99}$'s may be taken together to form a double bond.

Illustrative compounds which may be bonded to a free radical compound are 17-hydroxydioxycorticosterone (Compound S), deoxycorticosterone, cortisone, corticosterone, 11-dihydrocortisone (Compound F), cortisol, prednisolone and aldosterone.

Illustrative compounds which may be linked to a free radical compound include $O^{21}$-carboxymethyl corticosterone, N-carboxymethyl 21-carbamate cortisol, 21-cortisone succinate, 21-deoxocorticosterone succinate, and $O^{17}$-methyl, $O^{21}$-carboxymethyl cortisone.

An additional steroid family is the sapogenins of which digitalis is an important member. The basic compound is gitoxigenin, which is also found as the glycoside. The compounds of interest have the following formula:

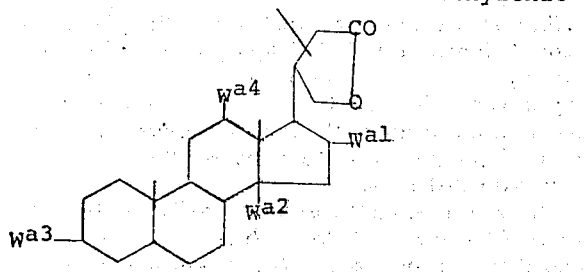

wherein:

any one of the W groups can be —X*-A* or an H of any of the W groups may be replaced by —X*-A*. X*-A* will be defined subsequently (there is only one —X*-A* per molecule);

$W^{a1}$, $W^{a2}$, $W^{a3}$ and $W^{a4}$ are hydrogen or hydroxyl, usually hydroxyl.

Vitamins

The next group of compounds are the vitamins. Chemically, the vitamins do not provide a simple chemical class, varying greatly in structure, but being classified as a group as to function. The vitamins include, vitamin A, which is a carotene, the B vitamin group which includes riboflavin, thiamine, niacin, pyridoxine, pantothenic acid, biotin, folic acid, and cyanocobalamine (Vitamin $B_{12}$); ascorbic acid (Vitamin C); the D vitamins which are steroidal derived; tocopherol (Vitamin E); and phytyl-1,4-naphthoquinone (Vitamin K).

Sugars

The next group of compounds are the sugars and saccharides. The saccharides are combinations of various sugars to form dimers, trimers and high molecular weight polymers, referred to as polysaccharides.

Prostaglandin

Another group of compounds of biological importance are the prostaglandins. These compounds when labeled have for the most part the following formula:

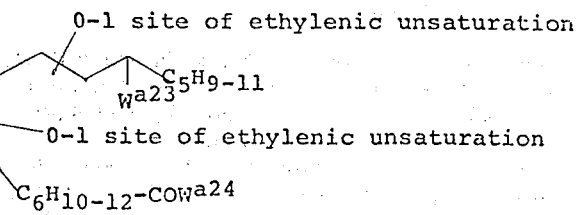

wherein:

any one of the W groups can be —X*-A* or an H of any of the W groups may be replaced by —X*-A*. X*-A* will be defined subsequently (there is only one —X*-A* per molecule);

$W^{a20}$ is hydrogen or hydroxyl;

$W^{a21}$ and $W^{a22}$ are hydrogen or hydroxyl, where two hydroxyl groups are bonded to the same carbon atom, oxo is intended;

$W^{a23}$ is hydrogen or hydroxyl; and $W^{a24}$ is hydroxyl, amino or an oxy group of from 1 to 6 carbon atoms, e.g., alkoxy.

Miscellaneous

Included in this group are the antibiotics such as penicillin, chloromycetin, actinomycetin and nucleic acids or derivatives, such as nucleosides and nucleotides.

Also of interest is serotonin which is 3-(2'-aminoethyl)-5-hydroxyindole. —X*-A* may be bonded at either of the amino nitrogen atoms or the hydroxyl group.

Of course, many of the compounds which are of interest undergo metabolic changes, when introduced into a vertebrate. The particular physiological fluid which is tested may have little, if any, of the original compound. Therefore, the original presence of the compound might only be detectable as a metabolite. In many instances, the metabolite may be the glucuronide, either oxy or oxo derivative of the original compound. In other instances, the original compound may have undergone oxidation, e.g., hydroxylation, reduction, acetylation, deamination, amination, methylation or extensive degradation. Where the metabolite still retains a substantial portion of the spatial and polar geometry of the original compound, it will be frequently possible to make the ligand analog based on either the original compound or metabolite. Where the metabolite is distinctively different than the original compound, the ligand analog will be based on the metabolite.

Besides metabolites of the various drugs, hormones and other compounds previously described, of significant interest are metabolites which relate to diseased states. Illustrative of such compounds are spermine, galactose, phenylpyruvic acid and porphyrin Type 1, which are believed to be diagnostic of certain tumors, galactosemia, phenylketonuria and congenital porphyra, respectively.

Two compounds of interest which are metabolites of epinephrine are vanillylmandelic acid and homovanillic acid. With these compounds, either the hydroxyl or carboxyl groups can be used as the site for —X*-A*.

Another general category of interest is the pesticides, e.g., insecticides, fungicides, bacteriocides and nematocides. Illustrative compounds include phosphates such as malathion, DDVP, dibrom, carbamates, such as Sevin, etc.

Since many of the biologically active materials are active in only one stereoisomeric form, it is understood that the active form is intended or the racemate, where the racemate is satisfactory and readily available. The antibodies will be specific for whatever form is used as the hapten.

Free Radical Group (A)

The free radical group is a stable free radical, preferably one which has a fairly simple electron spin resonance spectrum, which can be conveniently bonded through a linking group to the ligand. Various stable free radicals may be used, such as verdazyls, diarylamino radicals, aroxyl radicals, and nitroxide radicals. See Forrester, *Organic Chemistry of Stable Free Radicals*, Academic Press, New York (1968).

In the subject invention, the most versatile compounds are the nitroxide radical compounds, wherein the nitrogen of the nitroxide group is a heteroannular member. These compounds may be mono-or bicyclic, fused or unfused, and will normally be of from 7 to 36 carbon atoms, more usually of from 7 to 16 carbon atoms, wherein the annular members will normally be of from 4 to 9. The compounds may have from 0 to 2 other heteroannular members, more usually from 0 to 1, which are oxygen, nitrogen or sulphur. The nitrogen and sulfur may be bonded to oxygen: nitrogen to one oxygen atom, and sulfur to from 0 to 2 oxygen atoms, more usually 0 to 2. The compounds will normally have from 0 to 1 site of endo ethylenic unsaturation.

A special group of nitroxide compounds are the monoaryl and diaryl nitroxides, where the ortho and para positions are substituted, usually with alkoxy groups, in order to inhibit reaction between the two nitroxide compounds. In the monoaryl nitroxide compound, the other valence of the nitrogen will be bonded to a tertiary carbon atom.

The nitroxide compounds which find use in this invention will have the following formula:

wherein:

α and α' are organic radicals, which are incapable of forming a double bond to nitrogen without a substantial change in structure and are either aryl, normally trialkoxyaryl, tertiary alkyl, or may be taken together with the nitrogen to which they are attached to form a mono-or bicyclic ring of from 4 to 9 annular members.

For the most part, the compounds which will be employed will have the following formula:

wherein:

R and R' are hydrocarbon groups of from 1 to 12 carbon atoms, more usually from 1 to 6 carbon atoms, and preferably alkyl of from 1 to 3 carbon atoms; and Y is a divalent functionality of from 3 to 27 atoms other than hydrogen, more usually of from 3 to 12 atoms other than hydrogen, having a total of from 0 to 2 heteroatoms; oxygen, nitrogen or sulfur, which are annular members; Y forms a ring of from 4 to 6 annular members with the carbon and nitrogen atoms to which it is attached. One of the hydrogen atoms bonded to carbon, usually an annular carbon atom, will be replaced so as to provide a site for linking to the ligand.

Y will be bonded to the nitrogen of the nitroxide through carbon, the carbon atom being free of hydrogen or being sterically prevented from forming a double bond to nitrogen, e.g. by a endo double bond.

One preferred group of free radical compounds has the following formula:

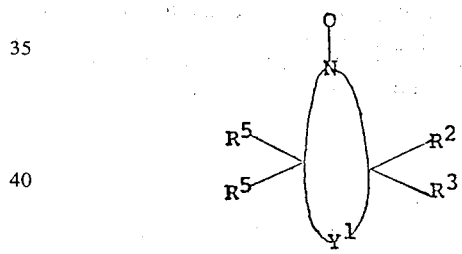

wherein $R^{2-5}$ are the same or different, preferably the same, and are hydrocarbon of from 1 to 12 carbon atoms, more usually of from 1 to 6 carbon atoms, preferably alkyl and particularly preferred methyl; $Y^1$ is a divalent radical having from 1 to 10 carbon atoms, more usually 1 to 4 carbon atoms and from 0 to 1 heteroatoms, there being from 1 to 3 annular members, usually carbon; $Y^1$ may have from 0 to 1 site of ethylenic unsaturation and preferably will form a pyrroline, pyrrolidine, or piperidine ring. The heteroatoms will normally be nitrogen, oxygen and sulfur.

A subgenus of the monocyclic nitroxide is the five membered ring having one annular heteroatom of the following formula:

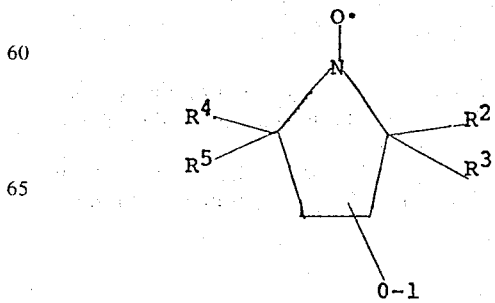

site of ethylenic unsaturation with $R^{2-5}$ defined as above.

Another subgenus is the six membered ring compounds which have the following formula:

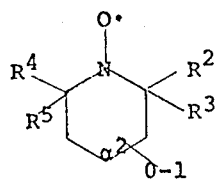

site of ethylenic unsaturation wherein $R^{2-5}$ are as defined above, and $\alpha^2$ is carbon or nitrogen.

The five membered rings having two annular heteroatoms will for the most part have the following formula:

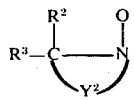

wherein $Y^2$ is

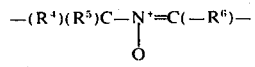

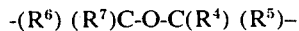
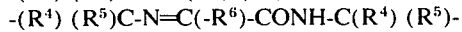

wherein $R^{2-5}$ are as defined above, $R^6$ and $R^7$ may be the same as $R^{2-5}$ or hydrogen.

A preferred nitroxide free radical containing group of compounds has the following formula:

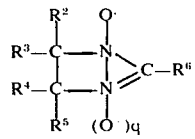

wherein q is 0 or 1, preferably 1, when q is 1, the nitrogen to which the oxygen is bonded is positive, $R^{2-5}$ have been defined previously, and $R^6$ is as defined above.

Illustrative rings include 1-oxylpiperidine, 1-oxylpyrrolidine, 1-oxylpyrroline, 1-oxylimidazolidine, 1-oxyl-3-oxyimidazolidine, 1-oxytetrahydropyridine and 3-oxyloxazolidine.

The bridgehead nitroxide compounds will for the most part have the following formula:

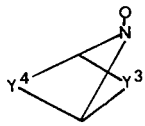

wherein:

$Y^3$ and $Y^4$ are divalent aliphatic hydrocarbon radicals having from 0 to 1 site of ethylenic unsaturation and of from 2 to 3 carbon atoms.

The last nitroxide to be specifically considered is the aryl nitroxide which will have the following formula:

wherein:

$\alpha^3$ is 2,4,6-trialkoxy benzene, wherein the alkoxy groups are of from 1 to 3 carbon atoms and $\alpha^4$ is the same as $\alpha^3$ or tertiary alkyl of from 4 to 12 carbon atoms, more usually of from 4 to 6 carbon atoms.

The verdazyls will for the most part have the following formula:

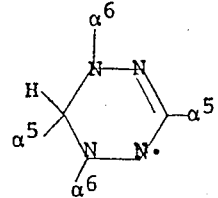

wherein:

$\alpha^5$ is hydrocarbon or a acyloxy of from 1 to 8 carbon atoms and $\alpha^6$ is aryl or substituted aryl, e.g., hydroxy or amino, of from 6 to 10 carbon atoms.

As already indicated, the free radical group is bonded to the ligand through a bond or linking group which is substituted on the free radical group by replacing one of the hydrogen atoms. In addition, sharper spectra can be obtained by replacing hydrogen atoms with deuterium atoms. It is therefore, to be understood when hydrogen is spoken of in referrring to the free radical group, that deuterium is to be treated as an equivalent.

In carrying out the subject invention, particularly where the ligand does not have a naturally occurring receptor or it is found to be more convenient to prepare antibodies, the ligand will be modified by providing a group which can be bonded to a protein. Therefore, some reactive functionality will be introduced into the ligand, either by activating a functionality which is present, e.g., by transforming a carboxylic acid to a mixed anhydride, or by introducing a new functionality, e.g., modifying a hydroxy group with a carboxymethyl group. Since the antibodies which are formed will recognize the ligand with its attached linking group, that was employed in preparing the antigenic material, normally the same ligand with its attached linking group used to prepare the antigenic material will also be used to bond to the free radical group. Therefore, most commonly, the substituents on the free radical group will be the relatively simple substituents such as amino, hydroxy and carboxy.

Illustrative compounds which will be used for linking to the ligand are 1-oxyl-3-amino-2,2,5,5-tetramethylpyrrolidine, 1-oxyl-3-hydroxy-2,2,5,5-tetramethylpyrrolidine, 1-oxyl-3-carboxy-2,2,5,5-tetramethylpyrrolidine, 1-oxyl-3-carboxy-2,2,5,5-tetramethylpyrrolidine, 1-oxyl-4-amino-2,2,6,6-tetramethylpiperidine, 1-oxyl-4-hydroxy-2,2,6,6-tetramethylpiperidine, 1-oxyl-4-carboxy-2,2,6,6-tetramethyltetrahydropyridine, 2-methylamino-1,3-dioxy-4,4,5,5-tetramethylimidazoline, 2-hydroxymethyl-1,3-dioxy-4,4,5,5-tetramethylimidazoline and 1-amino-7-oxyl-7-azabicycloheptane.

In many instances it may be advantageous to have a reactive group on the free radical group and bond that to the ligand. Whenever possible, this group would provide the same type or possibly even the same functional bridge to the ligand. In effect, it could merely be the reverse situation, the final compound being the same as if the linking group had been present in reverse on the ligand. For example, if there is an amino group on the ligand, it would be possible to modify the ligand group so as to form an isocyanate. Similarly, if there is an amino group on the free radical, it is also possible to modify that amino group to form an isocyanate. The bridge will be the ureylene, irrespective of which procedure was used.

Illustrative compounds which can be used for linking the free radical functionality to the ligand are 1-oxyl-2,2,5,5-tetramethyl-3-isocyanatopyrrolidine, 1-oxyl-2,2,5,5-tetraethyl-3-isothiocyanatopyrrolidine, N-(1-oxyl-2,6-dimethyl-2,6-dibenzylpiperidin-4-yl) succinamic acid, N-(1-oxyl-2,2,5,5-tetraethylpiperidin-4-yl) maleamic acid, N-(1-oxyl-2,2,5,5-tetrabutylpyrrolidin-3-yl) oxalamic acid, mono-(1-oxyl-2,2,5,5-tetramethylpiperid-4-yl) fumarate, N-(1-oxyl-2,2,5,5-tetramethylpiperid-4-yl)glycine, 1-oxyl-2,2,5,5-tetramethylpyrrolid-3-ylsulfonylacetic acid, 1-oxyl-2,2,5,5-tetramethyl-3-hydroxypyrrolidine, 1-oxyl-2,2,5,5-tetramethylpyrrolidin-3-ylcarboxylic acid, N-(1-oxyl-2,2,5,5-tetramethylpyrrolidin-3-yl) terephthalamic acid, 1-oxyl-2,2,5,5-pyrrolidin-3-yl malonate, 1-oxypyrrolidin-3-yl-3,5-dispiro-(1'-cyclopentane) carboxylic acid, 4,4,5,5-tetramethyl-1,2,3-trioxyimidazoline, 4,4,5,5-tetrapropyl-2-bromomethyl-1-oxyl-3-oxide-imidazoline, 4,4,5,5-tetrabenzyl-2-(p-aminophenyl)-1-oxyl-3-oxide-imidazoline, 4,4,5,5-tetramethyl-2-chlorosulfonylmethyl-1-oxyl-3-oxide-imidazoline, 4,4,5,5-tetramethyl-2-carboxymethyl-1-oxyl-3-oxide-imidazoline, 5,6-dimethyl-4,5-(butylene-1,4)-2-isocyanatomethyl-1-oxyl-imidazoline, 4,4,5,5-tetramethyl-2-carboxycarbonyl-1-oxyl-3-oxide-imidazoline, and 2-chlorocarbonyl-1-oxyl-3-oxide-imidazoline-4,5-dispiro(1'-cyclohexane).

Linking Groups

The group -X*- will vary depending on the available sites for attachment on A*. For the most part, the available groups on the ligand, either naturally present or introduced, will be hydroxyl (—OH); amino

where $R^8$ will usually be hydrogen or alkyl of from 1 to 6 carbon atoms); mercapto (—SH); oxo (—C=O); carboxy (—CO$_2$H); and methine ($\equiv$CH), where the H is bonded, usually to an aromatic carbon atom and preferably the ring is activated by oxy or amino substituents.

The primary function of the linking group is to bond the free radical to the ligand within a relatively short distance of each other. However, the linking group may also be used to fulfill other functions, such as to modify the solubility properties of the final product. Particularly when relatively large hydrophobic groups are employed, as in steroids, a group capable of forming a salt may be introduced into the linking group. Illustrative groups are carboxylates, sulfonates, sulfates and quaternary ammonium salts. The counter ion may be any convenient counter ion, preferably monovalent, such as chloride, fluoride, alkali metal salt, ammonium etc.

The linking group will usually be of from 0 to 8 carbon atoms, more usually of from 0 to 6 carbon atoms and from 1 to 8 heteroatoms, more usually of from 1 to 6 heteroatoms which are oxygen, sulfur and nitrogen, more usually oxygen and nitrogen. Any counter ion to a salt forming group is not to be counted in the number of hetero atoms. The preferred groups are the nonoxocarbonyl or thiocarbonyl, alkylamino or alkoxy as linking functionalities.

The chain length of the linking groups is preferably from 1 to 10 atoms, usually 2 to 6 atoms or the equivalent, when cyclic structures are involved.

A linking group that finds particular use is the hydrocarbylcarboxamido or oxyhydrocarbylcarboxamido of from 2 to 8 carbon atoms, usually of from 2 to 6 carbon atoms and from 0 to 1 site of aliphatic unsaturation. Usually the hydrocarbylene is aliphatic and will be represented by Z in the following formulas.

The following tabulation indicates the various linking groups, varying with the functonalities present on the ligand and the free radical.

| Ligand | Free Radical |
|---|---|
| (hydroxyl (—O—); amino(—N(R$^9$)) | (hydroxyl (—O—); amino(—N(R$^9$)) |
| | $-\overset{\overset{T}{\|}}{C}-$ |
| | $-\overset{\overset{T}{\|}}{C}-Z-\overset{\overset{T}{\|}}{C}-$ |
| | $-Z-\overset{\overset{T}{\|}}{C}-$ |
| | $-\overset{\overset{T}{\|}}{C}-Z-$ |
| | $-SO_2-Z-SO_2-$ |
| | $-\overset{\overset{T}{\|}}{C}-Z-SO_2$ |
| | $-SO_2-Z-\overset{\overset{T}{\|}}{C}-$ |
| | $-Z-SO_2$ |
| | $-SO_2-Z$ |
| | $=Z'-$ |
| | $-Z-$ | wherein:
$R^9$ is hydrogen or hydrocarbon of from 1 to 6 carbon atoms;

T is oxygen, sulfur, or NR', wherein R' is hydrogen or hydrocarbon of from 1 to 6 carbon atoms, usually H; T is usually oxygen;

Z' is alkylidenyl

Z is a bond; hydrocarbon of from 1 to 10 carbon atoms, more usually alkylene of from 1 to 6 carbon atoms, alkenylene of from 2 to 6 carbon atoms, alkynylene of from 2 to 6 carbon atoms, cycloalkylene of from 4 to 10 carbon atoms, arylene of from 6 to 10 carbon atoms, oxaalkylene of from 4 to 8 carbon atoms, and azaalkylene of from 4 to 8 carbon atoms.

When the linking functionality is hydroxyl, Z or a nonoxocarbonyl bond to the hydroxy is preferred, particularly Z.

When the linking functionality is amino, nonoxocarbonyl, the sulfur and nitrogen analogs, or Z are preferred, particularly nonoxocarbonyl.

| Ligand | Free Radical |
|---|---|
| (oxocarbonyl(—$\overset{\|}{C}$=O)) | (hydroxy(—O—); amino (—N(R$^9$)—) |
| | =N—O—Z |
| | =N—O—Z—CT |
| | =N—O$_2$CZCT— |
| | =CHCH— |
| | =NNH—Z—CT— |

| Ligand | Free Radical |
|---|---|
| (nonoxocarbonyl(—C(=O)—)) | (hydroxy(—O—); amino(—N(R⁹)—)<br>—O—Z—CT<br>—N(R⁹)—Z—CT—<br>—N(R⁹)—Z—<br>—O—Z— |

| Ligand | Free Radical |
|---|---|
| (methine(≡CH)) | (hydroxy(—O—); amino(—N(R⁹)—)<br>—N₂—Z″—<br>—N₂—Z″—CT— | wherein Z, T, and R⁹ are as defined previously and Z″ is arylene of from 6 to 10 carbon atoms Where the free radical group has a carboxy functionality (nonoxocarbonyl), the groups would then be $$-\overset{O}{\underset{\|}{C}}-O-\quad \text{or} \quad -\overset{O}{\underset{\|}{C}}-N(R^9)-$$

where the oxygen and nitrogen are bonded to any of the linking groups indicated above, and where Z or Z″ is bonded to the oxygen or nitrogen.

Where the free radical has an oxocarbonyl group and the ligand an hydroxy or amino group, one need only reverse the linking group for the oxocarbonyl on the ligand and hydroxy or amino on the free radical group.

The following table indicates the linking groups for oxocarbonyl being present in the free radical and other than hydroxy or amino on the ligand, the symbols having been defined previously.

| Ligand | Free Radical |
|---|---|
| (oxocarbonyl(—C=O)) | (oxocarbonyl(—C=O))<br>=N—O—Z—N=<br>=N—O₂C—Z—CO₂N=<br>=N—O—Z—CO₂N=<br>—NNH—Z—NHN= |

| Ligand | Free Radical |
|---|---|
| (nonoxocarbonyl(—C=O)) | (oxocarbonyl(—C=O))<br>—O—Z—O—N=<br>—N(R⁹)—Z—O—N=<br>—O—N=<br>—O—Z—HNN=<br>—N(R⁹)—ZHNN= |

| Ligand | Free Radical |
|---|---|
| (methine(=CH—)) | (oxocarbonyl(—C=O))<br>—N₂—Z″—O—N=<br>—N₂—Z″—NHN=<br>—N₂—ZCO₂N=<br>—N₂—ZCTNHN= |

The preferred Z groups (Z, Z′ and Z″) are hydrocarbylene having from 0 to 1 site of aliphatic unsaturation, e.g., ethylenic. Hydrocarbylene is a divalent radical composed solely of carbon and hydrogen, which may be aliphatic, alicyclic, aromatic or combinations thereof, e.g., aralkyl.

Where the ligand has a mercapto group, the maleimide functionality is particularly useful, where the imide nitrogen is either directly bonded to the free radical group, or bonded through the functionalities described above, e.g., carboxymethyl.

While for the most part, the free radical functionality may be bonded to any convenient position of the ligand, either through a functionality naturally present in the ligand or one introduced synthetically, there are preferred methods of bonding the free radical functionality to the ligand. First, it should be recognized that the free radical substituted ligand need not have any biologic activity. One is solely concerned in not disturbing the geometry and polar site relationships of a substantial portion of the molecule. Therefore, assuming synthetic convenience, the free radical functionality will normally be introduced at one end of the molecule.

Furthermore, if one is attempting to assay one of a variety of molecules which are quite similar, for example steroids, but differing in their substituents at the 17 position, one would choose to mark the molecule with the free radical functionality at a site distant from the functionality, which provides the distinction between the compound to be assayed and similar compounds which may also be present in the composition which is being assayed. For example, in assaying for steroids, it would frequently be preferable to bond at the 3 or 6 position rather than at the 17 position, since the distinctive portion of the molecule is normally at the 17 position, the 3 position for the most part remaining the same or differing in being an alcohol or a ketone with most steroids.

With a low molecular weight polypeptide, it would also be preferable to bond the free radical group to an amino acid which is not directly involved with the receptor site and not an amino acid which is involved in the receptor site. Therefore, a primary rule is that one does not modify the distinctive area of the molecule, by bonding the free radical functionality to that area, thus creating a geometry describing the free radical functionality and not the functionality of the molecule.

Also it may be found that better binding with a receptor is achieved by having the free radical functionality bonded to one site rather than another site. This can be readily determined by preparing a number of free radical modified ligand compounds and determining their equilibrium concentration with the receptor. This is particularly true where the ligand is a hapten. Almost invariably, the site of the ligand, and usually the linking group, will be the same for bonding the ligand to the protein as the ligand to the free radical. In this way, that portion of the ligand molecule which extends from the protein and is the most likely portion of the molecule to provide a template for the antibodies, is the same portion of the molecule which remains unmodified by the linking group to the free radical group.

For an excellent discussion of linking groups for steroids, for conjugation to proteins, see Peron, et al., Immunologic Methods in Steroid Determination, Appleton, Century Crofts, New York 1970.

RECEPTOR

In the subject invention, for the most part, the receptors will be macromolecules which have sites which recognize specific structures. The recognition of the specific structures will be based on van der Waals forces, which provide a specific spatial environment which maximizes the van der Waals forces; dipole interactions, either by permanent or induced dipoles; hydrogen and ionic bonding; coordinate covalent bonding; and, in some cases, covalent bonding. For a detailed discussion of mechanisms by which receptors bond ligands, see Goldstein, et al., Principles of Drug Action, Harper and Rowe, New York 1968.

The macromolecules of greatest interest are proteins and nucleic acids which are found within cells, blood, and other biological fluids. These compounds include enzymes, antibodies, ribonucleic acid (RNA) and deoxyribonucleic acid (DNA), carrier proteins, such as transcortin, thyroid binding globulin (TBG), thyroid binding prealbumin (TBP), and "bound" receptors (that is, receptors bound to cell membranes).

The most convenient group of proteins for use in the subject invention are antibodies. These materials are conveniently used in the analysis of the category of ligands referred to as haptens. Antibodies are produced by introducing an immunogenic substance into the bloodstream of a living animal. The response to the introduction of the immunogenic substance or antigen is the production of antibodies which act to coat the antigen and detoxify it or precipitate it from solution. The antibodies form a coat which is geometrically arranged so as to fit the spatial arrangement of the antigen. This may be analogised to a lock and key. The interaction is normally reversible, in that the antigen is subject to displacement or removal by various means without destruction of the receptor site.

There are many materials which are antigens and will produce an immunogenic response by being introduced into the bloodstream of a mammal. However, a number of materials of interest are not antigens, but are haptens, and in that situation, an extra step in preparing the antibody is required. This method of preparing antibodies with materials other than antigens is well known and may be found in Microbiology, Hoeber Medical Division, Harper and Rowe, 1969. See also, Landsteiner, Specificity of Serological Reactions, Dover Publications, N.Y. 1962; Kabat, et al., Experimental Immunochemistry, Charles C. Thomas, Springfield, Illinois, 1967; and Williams, et al, Methods in Immunology and Immunochemistry, Vol. I, Academic Press, New York, 1967.

The material which is to be assayed is bonded to a protein by any convenient means and the modified protein introduced into the bloodstream. The same type of bonding groups used with the free radical attachment to the ligand may be employed. The antibodies which form will include groups of antibodies which are shaped to fit the foreign moiety (hapten) bonded to the protein. Therefore, antibodies are obtained which are specific to the compound or hapten bonded to the protein. By careful separation techniques, the antibodies primarily concerned with the hapten in question, can be concentrated so as to provide an antibody composition which is primarily related to the specific hapten which was bonded to the protein.

To illustrate this method, para-aminobenzene arsonate is diazotized to form the diazo salt. By combining the diazo salt with rabbit globulin, the rabbit globulin is labeled with para-azobenzene arsonate. By introducing this composition into the bloodstream of an animal other than a rabbit, for example, a sheep, antibodies can be formed which will have a spatial arrangement which recognizes the azobenzene arsonate.

In addition to antibodies, there are a number of naturally occurring receptors which are specific to compounds of biological interest. Compounds for which receptors are naturally occurring include thyroxine, corticosterone, cortisone, 11-desoxycortisol, 11-hydroxyprogesterone, estrogen, insulin and angiotensin. See, for example, Vonderhaar, et al., Biochem. Biophysics Acta, 176, 626 (1969). All of these ligands have been studied and reported upon in the literature in connection with studies on their binding with specific receptors.

If desired, the antibodies may be bonded to a variety of supports. The bonding may be carried out similarly to that employed for bonding the protein to a ligand. Various supports include polyacrylamides, copolymers of vinyl acetate and acrylic acid, polyvinyl esters, modified cellulose Agarose, Sepharose, etc. The value of the support, is that the antibody may be easily separated from the solution in this manner and the clear solution analyzed. Therefore, the spectrum resulting from any of the radical absorbed on the antibody will no be present in the assay. An illustrative support is para-aminobenzamidoethyl-Bio-Gel P-60 supplied by Bio-Rad Laboratories of Richmond, California.

Method

The method employing the compounds of this invention is concerned with determining the amount of a specific material "ligand" - in a solution by bringing together a high molecular weight material having a site characteristic of the polar nature and spatial geometry of the ligand to be determined - "receptor" and a free radical analog of the ligand - "ligand analog" -. The electron spin resonance spectrum of the free radical functionality will vary when associated with a relatively small molecule, as compared to being associated with a substantially larger molecule. In a solution containing only ligand analog and receptor, at equilibrium the receptor sites will be substantially filled with ligand analog. Upon adding a small amount of ligand to the solution, the ligand and ligand analog will compete for the deficiency of receptor sites, affecting the position of the equilibrium and the appearance of the spectrum. By using known amounts of ligand, the effect on the equilibrium can be readily determined, as seen by the change in the electron spin resonance spectrum. Once the standards have been calibrated, various devices can be employed which will provide a reading indicating directly the amount of the unknown material.

In carrying out the assay, three basic reagents are involved: the unknown or ligand; the free radical analog; and the receptor. The free radical analog and the receptor are conveniently prepared as reagent solutions, with additional reagents, as required, being in one or both of the solutions. Reagents may be transported either dry or in solution. Liquids are convenient for the transfer of small amounts of materials, since they are readily metered.

Polar solvents will normally be used, particularly hydroxylic solvents, such as water and aqueous alkanols of from 1 to 2 carbon atoms (methanol and ethanol). Other oxygenated solvents may also be employed, such as ethers, esters, dimethyl formamide, dimethyl sulfoxide, hexamethyl phosphoramide, etc., usually in combination with water in amounts of 0 to 40, more usually 1 to 30 volume percent.

In carrying out the assay, the dilution factor for each reagent will usually be 1.5 to 10, more usually 1.5 to 5. Therefore, the original concentration of the reagent in the reagent solution will to some extent anticipate the final concentration of the reagent in the assay.

The concentration of the receptor in the reagent solution will usually be in the range of $10^{-9}$ to $10^{-3}$ M, preferably $10^{-7}$ to $10^{-3}$ M, based on active sites. (The method of determination of active sites will be described in the experimental section.) Usually, this will roughly be about $10^{-4}$ to 100 mg/ml, more usually, about $10^{-2}$ to 10 mg/ml. For the assay, the concentration of receptor sites, should be about $10^{-3}$ to $10^{-9}$ M, more usually $10^{-4}$ to $10^{-8}$ M.

The motor concentration ranges for the ligand analog will parallel those of the receptor, both as to the reagent solution and as to the assay concentration. The ratio of ligand analog to receptor will usually be from 0.5 to 10, more usually 0.5 to 3 molecules per receptor site. The ratio will be governed by the binding constants, the method of determination, the suspected concentration of ligand and the specificity of the assay.

Usually, it will be desirable to have the assay mixture buffered, so as to have a mixture with a pH in the range of 5.0 to 10.5, preferably 7.0 to 8.5. The concentration of buffer will vary with the buffer, usually in the reagent solution being about 0.05 to 0.8 M, more usually 0.2 to 0.7 M. The more acid the unknown solution, the higher the pH of the reagent solution which is used. In the assay mixture, the buffer concentration will usually be about 0.1 to 0.6 M.

The choice of buffer will vary widely, depending on its effect on the reagents, e.g., solubility, inertness to the reagents, etc. Various buffers which are commonly used include tri(hydroxymethyl)methyl amine (Tris); alkali metal and ammonium borates, e.g., sodium borate; alkali metal and ammonium phosphate e.g., sodium and disodium phosphate; alkali metal bicarbonate and carbonate, e.g., sodium bicarbonate and carbonate; ethylenediaminetetraacetic and, amine diols in combination with their salts, e.g., 2-amino-2-methyl-1,3-propandiol hydrochloride; ammonium chloride-ammonium hydroxide combination; barbital-alkali metal barbital combination; heterocyclic amines in combination with their salts, e.g., collidine-hydrochloric acid, collidine-pyridine-acetic acid, ethanolamine-hydrochloric acid, N-ethylmorphine-pyridine-acetic acid, glycine-hydrochloric acid, piperazine-glycylglycine, etc. The preferred buffers are Tris, bicarbonate-carbonate, phosphate and borate. With the inorganic buffers, it is frequently convenient to neutralize the inorganic acid, e.g., boric acid, with an alkali metal base, e.g., sodium hydroxide, to the desired pH.

Other salts or reagents may also be present in the reagent solution, as required.

In some instances, pretreatment of the unknown substrate may be required. Where the unknown is suspected of containing a reductant, e.g., ascorbic acid, which is capable of reducing the free radical, the unknown substrate may be treated with an oxidizing agent, such as sodium dichromate, sodium perborate, sodium periodate, iodine, etc. The choice of oxidizing agent will be governed by its effect on the other reagents which will be present in the assay. Alkali metal dichromate, particularly sodium dichromate and sodium hypoiodite, are oxidants of choice. The amount of oxidant will be governed by the suspected amount of reductant. With urine, concentrations $10^{-1}$ to $10^{-3}$ M will usually suffice.

The order in which the reagents are brought together will be relatively arbitrary, governed to some degree on the interaction between the free radical ligand analog and the receptor. Therefore, the free radical ligand analog may be used bound to the receptor, and the unknown solution added. Or, the unknown solution and free radical ligand analog may be added simultaneously to compete for the sites on the receptor. In some instances, the ligand may first be bound to the receptor, and the ligand analog added. Any of these methods can be accurately calibrated and used for determination of a particular ligand. When convenient, the solution may be separated from the receptor, and the concentration of the free radical ligand analog in the solution determined. This can also be related to the unknown ligand concentration.

The solutions are mixed to provide reasonable homogeneity and, if necessary, transferred to an electron spin resonance sample holder. The holder is then introduced into an electron spin resonance spectrometer cavity. The temperature in the cavity is normally maintained in the range of about 15° C to 40° C, and the change in the spectrum metered. Depending on the method of standardization and method of calibration, one or more points may have to be determined in order to determine the concentration of the unknown ligand.

Extremely small volumes are employed for the determination, usually in the range of 10 to 100 $\mu l$ for the total volume of reagents and unknown. The amount of unknown ligand that is required will normally be in the range of about $10^{-5}$ to $10^{-15}$ moles, more usually $10^{-7}$ to $10^{-13}$ moles.

A modification, which adds an additional procedural step, is to have the receptor bound to a support. This normally involves a heterogeneous system, rather than a homogeneous system. In many instances the advantageous use of the support in a heterogeneous system, more than offsets the additional effort involved in bonding the receptor to the support.

One way in which the support could be used is to pack a column (a column would probably be a small capillary tube) with the receptor bound to the support, and then bind ligand analog to the receptor. The amount of ligand analog present could be determined by measuring the electron spin resonance spectrum of the column, or preferably measuring the amount of ligand analog in solution before and after passage through the column. Now, relatively large amounts of the unknown fluid could be passed through the column, followed by determining the spectrum of the column or of the effluent. The change in spectrum would be proportional to the amount of ligand in the fluid passed through the column. (Also the rate of flow if equilibrium is not established.)

Alternatively, one could mix ligand and ligand analog, with the receptor bound to the support in a tube. After equilibrium was established, by separating the receptor bound to the support from the supernatant liquid, one could measure the electron spin resonance of either or both, the support or the supernatant liquid. A further variation, would be to determine the remaining ligand analog bound to the support by addition of ligand to the support, so as to release any remaining ligand analog and to analyze for the ligand analog in solution.

In addition, supports will find particular use, when a large molecule, usually in excess of 5,000 molecular weight, and more usually in excess of 10,000 molecular weight, is the ligand to be assayed. It is found, that when the free radical compound is bonded to a large molecule, significantly in excess of 5,000 molecular weight, the spin approximates that of an immobilized spin in solution. Therefore, further binding to a receptor, does not significantly change the spin of the free radical. It is thus appropriate to bind the receptor to the support, carry out the assay by adding ligand analog and ligand to the support and then determining the amount of ligand analog in a solution and/or on the support. In this instance, one is not determining the change in electron spin resonance spectrum due to change of immobilized spin to mobilized spin, but rather the absolute number of free radical groups which are present.

In order to demonstrate the broad spectrum of compounds which may be assayed, a number of different haptens of distinctively different structure and polar nature were used and bonded in a variety of ways to different nitroxide containing radical compounds. These compounds are not antigens and were therefore bonded to proteins which are then used for the formation of antibodies. The antibodies are shown as being used both with and without supports.

Experimental

The following examples are offered by way of illustration and not by way of limitation.

(All the temperatures are reported in Centigrade)

| | | |
|---|---|---|
| A. | Preparation of rabbit serum and γ-globulin | 88 |
| B. | Isolation of antibodies | 90 |
| C. | Binding of antibodies to support | 91 |
| 1.1 | 3-[2'-(2'',4''-Dinitroanilino) acetamido]-2,2,5,5-tetramethylpyrrolidinyl-1-oxyl | 92 |
| 1.2 | 3-[3'-(2''',4''-Dinitrophenylamino)propyl]carbamoyl 2,2,5,5-tetramethylpyrrolidinyl-1-oxyl | 93 |
| 1.3 | 4'(2',4'-Dinitroanilino)-2,2,6,6-tetramethylpiperidino-1-oxyl | 94 |
| 2.1 | 3-[2'-(O$^{3''}$-Morphino)acetamido]-2,2,5,5-tetramethylpyrrolidinyl-1-oxyl | 95 |
| 2.2 | 4-[2'-(O$^{3''}$ Morphino)acetamido]-2,2,6,6-tetramethylpiperidino-1-oxyl | 96 |
| 2.3 | 3-(O$^{3'}$-Morphinomethyl)-2,2,5,5-tetramethylpyrrolinyl-2-oxyl | 97 |
| 2.4 | 3-(O$^{3'}$-Morphinoacetamido)-2,2,5,5-tetramethylpyrrolidinyl-1-oxyl | 98 |
| 2.5 | 3-[2'-(O$^{3''}$-Morphino)butyramido]-2,2,5,5-tetramethylpyrrolidinyl-1-oxyl | 100 |
| 2.6 | 3-(2'-(O-$^{3''}$-Morphino)-3'-methylbutyramido)-2,2,5,5-tetramethylpyrrolidinyl-1-oxyl | 103 |
| 2.7 | O$^3$-(Carbomethoxyhexamethylene-)morphine | 106 |
| 2.8 | 3-[(N-Normorphino)acetamido]-2,2,5,5-tetramethylpyrrolidinyl-1-oxyl | 108 |
| 2.9 | Conjugation of carboxymethyl morphine with poly-L-lysine (PLL) | 112 |
| 2.10 | Conjugation of carboxymethyl morphine to bovine serum albumin (BSA) | 114 |
| 2.11 | Conjugation of N-carboxymethylnormorphine to bovine serum albumin (BSA) | 115 |
| 3.1 | 3-(N-(1'-Phenyl-2'-propyl)glycinamido)-2,2,5,5-tetramethylpyrrolidinyl-1-oxyl | 116 |
| 3.2 | 3-[N'(1'-Phenyl-2'-propyl)glycinamido]-2,2,5,5-tetramethylpyrrolidinyl-1-oxyl | 117 |
| 3.3 | 3[p-(2'-Aminopropyl-1')phenoxy)acetamido]-2,2,5,5-tetramethylpyrrolidinyl-1-oxyl | 119 |
| 3.4 | [4'-(1''-Phenyl-2''-propylamino)crotonamido]-2,2,5,5-tetramethylpyrrolidinyl-1-oxyl | 121 |
| 3.5 | 3-[5'-(1''-Phenyl-2''-propylamino)pentanamido.]-2,2,5,5-tetramethylpyrrolidinyl-1-oxyl | 123 |
| 3.6 | N-Trifluoroacethyl, N-methyl p-(2'-aminopropyl-1')-phenoxyacetic acid | 125 |
| 3.7 | N-Trifluoroacetyl 4-amino-5-phenylpentanoic acid | 127 |
| 3.8 | 4-Methylamino-5-phenylpentanoic acid | 129 |
| 3.9 | 3-Methylamino-4-phenylbutyric acid | 130 |
| 3.10 | Conjugate of N-carboxymethyl amphetamine and bovine serum albumin (BSA) | 132 |
| 3.11 | Conjugate of 3-methylamino-4-phenylbutyric acid and bovine serum albumin (BSA) | 134 |
| 3.12 | Conjugate of p-(2-amino-and 2-methylaminopropyl-1)-phenoxyacetic acid and bovine serum albumin (BSA) | 135 |
| 3.13 | Conjugation of 4-amino-and 4-methylamino-5-phenylpentanoic acid | 137 |
| 3.14 | Conjugation of N-carboxymethylamphetamine to bovine serum albumin (BSA) | 138 |
| 4.1 | N-Carboxymethyl phenobarbitone | 139 |
| 4.2 | 4-(2'-Pentyl)-5'-(carboxymethyl)barbituric acid | 142 |
| 4.3 | 4-(2'-Pentyl)-5-(3'-carboxyprop-2'-enyl-1')barbituric acid | 144 |
| 4.4 | N-carboxymethyl seconal | 145 |
| 4.5 | N-(1-Carboxyethyl)phenobarbitone | 146 |
| 4.6 | N-Carboxymethyl glutethimide | 148 |
| 4.7 | General procedure for spin labeling carboxy derivatized compounds | 149 |
| 4.8 | 3-[4'-(5''[5''-(2'''-pentyl)barbituryl)crotonamido]-2,2,5,5-tetramethylpyrrolidinyl-1-oxyl | 151 |
| 4.9 | 3-[5'-(5''-Ethyl-5''-phenylbarbituryl-1'')pentanamido]-2,2,5,5-tetrmaethylpyrrolidinyl-1-oxyl | 152 |
| 4.10 | 3-[4'-(5''-phenyl-5'''-ethylbarbituryl-1''')crotonamido]-2,2,5,5-tetramethylpyrrolidinyl-1-oxyl | 155 |
| 4.11 | 5'(3'-Carboxy-2'-dimethylaminopropyl)-5-phenyl-barbituric acid | 157 |
| 4.12 | Conjugate of N-carboxymethyl phenobarbitone and bovine serum albumin (BSA) | 159 |
| 4.13 | Conjugation of 5-(γ-crotonic acid)-5-(2'-pentyl) barbituric acid with bovine serum albumin (BSA) | 160 |
| 4.14 | Conjugation of N-carboxymethyl glutethimide with bovine serum albumin (BSA) | 161 |
| 5.1 | 3-Carboxy-2,2,5,5-tetramethyl-1-pyrrolidinyl-1-oxyl (4-'-carbethoxy-4'-phenyl)piperidide | 162 |
| 5.2 | 4'-(2-(4'-Carbethoxy-4'-phenyl-1'-piperidino)acetamido)-2,2,6,6-tetramethyl-1-piperidinooxyl | 163 |
| 5.3 | 3-[N-(4'-(4'-Phenyl-1'-methylpiperidinyl))carbamoyl]-2,2,5,5-tetramethylpyrrolidinyl-1-oxyl | 164 |
| 5.4 | 3-(2'-(4''-Carbethoxy-4''-phenylpiperidinyl-1''')acetamido]-2,2,5,5-tetramethyl-1-pyrrolidinyl-1-oxyl | 165 |
| 5.5 | Conjugation of 4-carboxy-1-methyl-4-phenyl-pipericine with bovine serum albumin (BSA) | 166 |
| 5.6 | Conjugation of 4-carbethoxy-1-carboxymethyl-4-phenyl- | |

| | | |
|---|---|---|
| 6.1 | piperidine to bovine serum albumin (BSA) N-2′,2′,5′,5′-tetramethylpyrrolidin-3′-yl-1′-oxyl 6-keto-7,7-diphenyl-9-(dimethylamino)-decanamide | 167 170 |
| 6.2 | Methadone-BSA conjugate | 172 |
| 7.1 | N-(p-cocainyl) and N-(p-benzoylecgonine) (1-oxyl-2,2,5,5-tetramethylpyrrolidinyl-3)formamide | 173 |
| 7.2 | 3-(N′-Norcocainyl)acetamido)-2,2,5,5-pyrrolidinyl-1-oxyl | 176 |
| 7.3 | N-[p-(1-Oxyl-2,2,5,5-tetramethylpyrrolidinyl-3-formamido]benzyl ecgonine methyl ester | 179 |
| 7.4 | 5-(N-Norcocainyl)valeric acid | 183 |
| 7.5 | 4-(N-Norcocainyl)crotonic acid | 185 |
| 7.6 | Conjugate of ecgonine and bovine serum albumin (BSA) | 187 |
| 7.7 | Conjugate of p-diazobenzoylecgonine with bovine serum albumin | 188 |
| 7.8 | Conjugate of N-(p-diazobenyl-)nor-ecgonine methyl ester with bovine serum albumin (BSA) | 189 |
| 7.9 | Conjugate of N-(p-diazobenzyl) nor-ecgonine with bovine serum albumin (BSA) | 190 |
| 7.10 | Conjugate of N-carboxymethyl nor-cocaine with bovine serum albumin (BSA) | 192 |
| 8.1 | 3-[(O³-Estradiolyl)acetamido]-2,2,5,5-tetramethyl-1-pyrrolidinyl-1-oxyl | 193 |
| 8.2 | 3-[(O³-Estronyl)acetamido]-2,2,5,5-tetramethyl-pyrrolidinyl-1-oxyl | 195 |
| 8.3 | Conjugate of O³-carboxymethyl estradiol with bovine serum albumin (BSA) | 196 |
| 8.4 | N-(2′,2′,5′,5′-Tetramethyl-1′-oxylpyrrolidinyl-3′) O³-estradiolylacetamidine | 197 |
| 8.5 | N-(O³-estradiolylethyl) N′-(2,2,5,5-tetramethyl-1-oxyl-pyrrolidinyl-3)thiourea | 199 |
| 8.6 | N-(2′,2′,5′,5′-Tetramethyl-1′-oxylpyrrolidinyl-3′) 6-[(O-aminocarbonylmethyl)oximino]estradiol | 201 |
| 8.7 | Conjugate of 6-(O-carboxymethyl)oximinoestradiol with bovine serum albumin | 204 |

EXAMPLE A

Preparation of Rabbit Serum and γ-Globulin

Antisera may be obtained as follows: The antigen (hapten coupled to an appropriate protein) is made up in a saline solution (9 g/liter) at a 2 mg/ml concentration. Per 1.0 ml aliquot of the above solution introduced, there is introduced simultaneously 3 ml of Complete Freund's Adjuvant in homogenized form by means of a two-way needle. For subcutaneous injections, approximately 0.3 ml (antigen + Freund's solution) is injected per site and for intraperitonealy injections, approximately 0.4 ml is injected. The total dosage is about 4.0 ml per rabbit.

After 3 to 4 weeks, a booster shot is given intramuscularly consisting of 0.5 ml of the above saline solution and 0.5 ml of Complete Freund's Adjuvant. A period of 5 to 7 days is allowed to pass and the rabbit is bled by heart puncture.

When the desired amount of blood is collected, the blood is allowed to clot and the clot removed. The remaining solution is then centrifuged at 2,000 rpm for 10 minutes. The serum is collected free of loose red cells.

An equal volume of saturated ammonium sulfate solution is added to the serum dropwise with stirring at 4°. After standing for 1 hour at that temperature, the solution is centrifuged at 10,000 rpm for 15 minutes and the supernatant removed. The residue is suspended in as small a volume as possible of 1X PBS (phosphate buffered saline, see below for description), transferred to a dialysis bag and dialyzed overnight against 1X PBS pH 7.0. The residue in the dialysis bag is then isolated and frozen.

(To make 1 l. of 10X PBS combine 76.5 g NaCl, 7.25 g $Na_2HPO_4$ (anh.), 2.12 g of $KH_2PO_4$ and 10.0 g of $NaN_3$; make up to 1 liter with distilled water, and adjust PH to 6.5 with 1N HCl. The 1X PBS is obtained by diluting 10X (tenfold), the pH changing to 7.0–7.1 as a result of the dilution.)

EXAMPLE B

Isolation of Antibodies

In 20 ml of dimethyl formamide was introduced 400 mg aminoethyl-Bio-Gel-P-60 and 300 mg of carboxymethyl morphine (See Example 2.4) and 1 g sodium bicarbonate added. After stirring the suspension for two days at 4°, the suspension was filtered, the residue washed with water until the washings were neutral, and then the residue was dried in vacuum.

The resulting product was then suspended in 20 ml rabbit serum containing morphine antibodies and stirred for 4 hours at 4°. Filtration gave a residue which was resuspended in 5 ml phthalate buffer, pH 3.8 (0.1M) and stirred for 2 hours. The gel was separated by centrifugation and the supernatant liquid dialyzed against phosphate buffer, pH 7.4 (0.1M) to give a buffered solution of substantially pure antibodies.

EXAMPLE C

Binding of antibodies to support

A. Para-aminobenzamidoethyl-Bio-Gel P-60 (50 mg) was suspended in 10 ml of water and acidified with 1N hydrochloric acid to pH 4.5. The suspension was cooled to 4° and 6 mg sodium nitrite dissolved in 2 ml water added over a period of 10 minutes. A one ml portion of $10^{-5}$ M solution of purified morphine antibodies was mixed with the above material at pH 9 while maintaining the temperature. After 40 minutes, 20 mg resorcinol was added to scavenge the remaining diazonium compound. The solid was then filtered and washed with pH 8 borate buffer.

B. The above supported morphine antibodies (50 mg) were suspended in 10 ml of pH 8 borate buffer solution $10^{-4}$ M in 4-[2′-(O³′′-morphino)acetamido]-2,2,6,6-tetramethylpiperidino-1-oxyl and stirred for 2 hours. Filtration and washing with water gave a solid (50 mg) which showed broad ESR signals indicating the binding of the free radical labeled morphine to the receptor.

EXAMPLE 1.1

3-[2′-(2′′,4′′-Dinitroanilino)acetamido]-2,2,5,5-tetramethylpyrrolidinyl-1-oxyl 3-Glycylamido-2,2,5,5-tetramethylpyrrolidinyl-1-oxyl (250 mg) was dissolved with stirring in 2 ml methanol. Potassium bicarbonate (0.5 g) was added followed by 0.5 ml of 2,4-dinitrofluorobenzene. Gas evolution subsided after one hour whereupon the solution was diluted with 10 ml of water and extracted with three 15 ml portions of chloroform. The combined organic layers were dried over anhydrous magnesium sulfate, filtered and evaporated. The oily residue was chromatographed on silica gel with 500 ml of chloroform followed by 250 ml of 1:1 chloroform/acetone. Evaporation of the solution and recyrstallization of the residue by addition of benzene yielded 370 mg (86 %). m.p. 125°–127° (decomp.) (recrystallization from 5 ml of ethyl acetate).

Anal. Calcd. for $C_{16}H_{22}N_5O_6$: C, 50.52; H, 5.82; N, 18.41

Found: C, 50.45; H, 5.89; N, 18.17
M.W. 380.396
ESR spectrum $a_N = 14.1$ Gauss (benzene)

EXAMPLE 1.2

3-[3'-(2'',4''-Dinitrophenylamino)propyl]carbamoyl-2,2,5,5-tetramethylpyrrolidinyl-1-oxyl 3-[3'-Aminopropyl]carbamoyl-2,2,5,5-tetramethylpyrrolidinyl-1-oxyl (250 mg) was dissolved in 2 ml methanol with stirring and 0.5 g of potassium bicarbonate and 0.5 ml 2,4-dinitrofluorobenzene added. After 2 hours the mixture was transferred to a separatory funnel, diluted with 15 ml water and extracted with three 15 ml portions of chloroform. The combined organic layers were dried over anhydrous magnesium sulfate, filtered and evaporated. The brown residue was chromatographed on silica gel with ethyl acetate. Evaporation of the solvent yielded an oil which crystallized on addition of ethyl acetate/carbon tetrachloride, yellow crystals (280 mg) m.p. 150°–151°.

Anal. Calcd. for $C_{18}H_{26}N_5O_6$: C, 52,92; H, 6.42; N, 17.15

Found: C, 52,60; H, 6.40; N, 16.95
M.W. 408.4

EXAMPLE 1.3

4-(2',4'-Dinitroanilino)-2,2,6,6-tetramethylpiperidino-1-oxyl

4-Amino-2,2,6,6-tetramethylpiperidino-1-oxyl (50 mg) was dissoved in 2 ml methanol with stirring and 0.5 mg potassium bicarbonate and 0.5 ml 2,4-dinitrofluorobenzene was added. A precipitate appeared, and after 12 minutes the reaction mixture was diluted with 15 ml of water and extracted with three 15 ml portions of chloroform. The combined organic extracts were dried over anhydrous magnesium sulfate, filtered and evaporated. Chromatography on silica gel with chloroform gave two yellow bands. The slower moving orange-yellow component was collected and the residue obtained from evaporation of the solvent was recrystallized from chloroform to give orange crystals, m.p. 178°–179°, followed by resolidification and remelting at 189°–190°

Anal. Calcd. for $C_{15}H_{21}N_4O_5$: C, 53.40; H, 6.28; N, 16.61

Found: C, 53,29; H, 6.18; N, 16.38
M.W. 337.3

EXAMPLE 2.1

3-[2'-($O^{3''}$-Morphino)acetamido]-2,2,5,5-tetramethylpyrrolidinyl-1-oxyl

3-Bromoacetamido-2,2,5,5-tetramethylpyrrolidin-1-oxyl (139 mg) and 153 mg morphine were refluxed under nitrogen in 4 ml ethanol with 22 mg sodium hydroxide for 2 hours. The reaction mixture was diluted with water and 2 ml of 2 M potassium hydroxide was added. After extraction with chloroform and reextraction of the extracts with water, the chloroform solution was dried with magnesium sulfate and evaporated to give a yellow residue (glass) m.p. 75°–81°. Attempts to recrystallize it failed. Chromatography on silica gel with chloroform/methanol 9:1 gave one main fraction which was the nitroxide radical. The radical was isolated by methanol extraction of the silica gel, rechromatographed, and isolated as before. Evaporation of the methanol, redissolution in chloroform, and centrifugation removed silica gel that was soluble in the methanol. On evaporation 113 mg of a yellow glass was obtained. ESR spectrum: $a_N - 14.58$ Gauss $(CHCl_3)$

EXAMPLE 2.2

4-[2'-($O^{3''}$ Morphino)acetamido]-2,2,6,6-tetramethylpiperidino-1-oxyl

Morphine (153 mg) was dissolved in 4 ml abs. ethanol under nitrogen and 146 mg of 4-bromoacetamido-2,2,6,6-tetramethylpiperidino-1-oxyl were added with stirring. After stirring the solution for 2 hours under reflux it was kept overnight at room temperature. The solution was diluted with water and extracted with chloroform (2 × 30 ml). The combined organic layers were reextracted with 50 ml water (3 drops aq. KOH) and then dried over anhydrous magnesium sulfate. After filtration and evaporation of the solvent there remained a brown oil, which showed one main component by thin layer chromatography (TLC). The product could not be crystallized.

EXAMPLE 2.3

3-($O^{3'}$-Morphinomethyl)-2,2,5,5-tetramethylpyrrolinyl-1-oxyl

A. To a stirred solution of 100 mg (0.58 mmole) of 3-hydroxymethyl-2,2,5,5-tetramethylpyrrolinyl-1-oxyl and 11.49 mg (0.62 mmole) of tri-n-butylamine in 15 ml of absolute ether was added 71.3 mg (0.60 mmole) of thionyl chloride. The reaction was stirred at room temperature for 2 hours and then evaporated. The resulting oil was purified by TLC on silica gel plates with chloroform. The yellow liquid obtained was used directly in the next reaction.

B. Sodium hydride was dissolved in absolute ethanol, and titrated with standard hydrochloric acid to a phenolphthalein end point.

Morphine (30.2 mg, 0.10 mmole) was dissolved in ethanol containing 0.10 mmole of sodium hydride and stirred under nitrogen to which was added 18.8 mg (0.1 mmole) of the above compound dissolved in 1 ml of absolute ethanol and the solution was refluxed for 2 hours. The reaction mixture was then decanted and evaporated. The resulting oil was purified by TLC, using silica gel plates with chloroform-methanol, 9:1, as the eluent. The product was a yellow glass, 15 mg.

EXAMPLE 2.4

3-($O^{3'}$-Morphinoacetamido)-2,2,5,5-tetramethylpyrrolidinyl-1-oxyl

A. Morphine (909 mg) was dried for 4 hours at 50°, 0.01 mm Hg. The dried morphine was dissolved in 18 ml of abs. ethanol and 350 mg dry sodium chloroacetate was added, followed by 125 mg sodium hydroxide. After purging with nitrogen, the solution was stirred and refluxed for four hours. The hot solution was treated with 3.8 ml. ethanolic hydrogen chloride (0.85 M) and then filtered while still warm. On cooling overnight, a precipitate (272 mg) formed which was collected and recrystallized from ethanol/water. On addition of ether to the original filtrate an additional precipitate was obtained which was also recrystallized from ethanol/water. Total yield 600 mg (55 %). On heating this product to 75° in vacuo there was a weight loss corresponding to 0.48 molecule of ethanol or 1.15 molecule of water. The dried compound decomposes at 190°–220° (depends on rate of heating).

Anal. Calcd. for $C_{19}H_{21}NO_5$: C, 66.45; H, 6.16; N, 4.08

Found: C, 65.87; H, 6.98; N, 4.09, 4.07

NMR $(C_5D_N)$ 2.44 ppm (-$CH_3$), 5.08 ppm (-$CH_2$-COO)

B. To 1.03 g (3.0 mmole) $O^3$-(carboxymethyl) morphine in 15 ml dry DMF at 0° was added 393 µl (3.0 mmole) isobutyl chloroformate and the mixture stirred for 1 hour under $N_2$. To the stirring solution was added a cooled (0°) solution of 470 mg (3.0 mmole) 3-amino-2,2,5,5-tetramethylpyrrolidinyl-1-oxyl in 5 ml dry DMF. The solution was allowed to come to room temperature over the weekend. The reaction mixture was poured into 60 ml of 10% aqueous sodium chloride, made basic with sodium carbonate, extracted with 4 × 60 ml benzene, dried over sodium carbonate and evaporated in vacuo to a glassy oil. The oil was triturated with 2 × 500 ml petroleum ether and recrystallized from 300 ml boiling cyclohexane. The yellow crystals were filtered and washed with 100 ml petroleum ether. 800 mg (55%) TLC:$R_f$ (0.3), $CHCl_3$:MeOH, 9:1. m.p. 60°–75°

EXAMPLE 2.5

3-[2'-($O^{3''}$-morphino)butyramido)-2,2,5,5-tetramethylpyrrolidinyl-1-oxyl

A. Anhydrous morphine (6.30 g, 22.1 mmoles) and 883 mg (22.1 mmoles) sodium hydroxide in 50 ml absolute ethanol was degassed and refluxed under $N_2$ until dissolution occurred. The ethanol was then removed under vacuum and 40 ml of freshly distilled anhydrous hexamethylphosphortriamide (HMPA) added along with 4.4 g (24.5 mmoles) methyl α-bromobutyrate and 1 g sodium iodide. The mixture was degassed and placed under $N_2$ at 65° for 5 hours. The cooled reaction mixture was poured into 400 ml of ice slurry and the aqueous slurry made basic with aqueous sodium carbonate, extracted with 2 × 200 ml ether. Combined ethereal extracts were washed with 100 ml 5% aqueous sodium carbonate, 100 ml water, 50 ml saturated aqueous sodium chloride, dried over sodium carbonate and evaporated in vacuo. The residue was placed under a vacuum of 0.05 mm Hg for 1 hour and taken up in one liter dry ether to which hydrogen chloride was added until precipitation ceased. The precipitate was filtered, washed with 500 ml ether and taken up in 100 ml water. The aqueous solution was made basic with sodium carbonate and the resulting oil taken up in 100 ml ether, dried over sodium carbonate, evaporated in vacuo and placed under vacuum for 2 hours to yield a viscous yellow oil which crystallized on standing. TLC $R_f$ (0.4) $CHCl_3$:MeOH, 9:1, silica gel.

B. The above ester (500 mg) in 10 ml 2N HCl was refluxed for 2 hours, stripped in vacuo and put under a vacuum of 0.05 mm Hg for 1 hour. The residue was taken up in 5 ml water neutralized to pH 6.5 with 2 N sodium hydroxide, washed with 10 ml of benzene, stripped in vacuo and dried at 0.05 mm Hg for 1 hour. Hot absolute ethanol (10 ml) was added to the residue and the suspension was centrifuged. The supernatant was decanted into 50 ml of acetone and the resulting ppt. was filtered and washed with 10 ml acetone to yield 400 mg of white crystals. TLC $R_f$(0.35)n-BuOH:-$H_2O$:HOAc 8:2:2, on silica.

C. The mixed anhydride was prepared by adding 67 µl (0.508 mmole) isobutyl chloroformate to a solution of 188 mg (0.508 mmole) $O^3$-carboxymethylmorphine(prepared above) in 3 ml anhydrous dimethylformamide (DMF) at 0° (ice bath) and allowing the resulting mixture to stir at 0° for 1 hour under nitrogen. To this was added a cooled solution of 80 mg (0.51 mmole) 3-amino-2,2,5,5-tetramethylpyrrolidinyl-1-oxyl in 1 ml DMF and the mixture allowed to stir under $N_2$ over the weekend. The reaction mixture was poured into 20 ml 10% aqueous sodium chloride and 5 ml 5% aqueous sodium carbonate, which was extracted with 3 × 20 ml benzene and the combined extracts dried with sodium carbonate and evaporated in vacuo. The residue was taken up in 10 ml boiling cyclohexane and an oil was obtained upon cooling. The cyclohexane was decanted and the procedure repeated with 10 ml cyclohexane to obtain pale yellow crystals upon cooling.

Crystals were filtered and washed with 10 ml of petroleum ether to yield 60 mg. $R_f$ (0.3) $CHCl_3$/MeOH, 9/1, Anal. Calcd. for $C_{29}H_{40}N_3O_5$: C, 68.21; H, 7.89; N, 8.23

Found: C, 67.94; H, 7.95; N, 7.94

EXAMPLE 2.6

3-(2'-($O^{3''}$-morphino)-3'-methylbutyramido)-2,2,5,5-tetramethylpyrrolidinyl-1-oxyl A. A mixture of 9.45 g (30.2 mmoles) morphine and 1.22 g (30.2 mmoles) sodium hydroxide in 50 ml absolute ethanol was degassed and refluxed under $N_2$ until dissolution. The solvent was evaporated in vacuo and the residue dried at 0.05 mm Hg for 1 hour. The residue was dissolved in 50 ml freshly distilled HMPA, 6.6 g (33.3 mmoles) methyl α-bromo-β-methylbutyrate and 1 g sodium iodide added. The mixture was degassed and heated to 65° for 4 days under $N_2$. The cooled mixture was poured into 400 ml of ice slurry and extracted with 3 × 100 ml ether. The ethereal extracts were combined, washed with 100 ml 5% aqueous sodium carbonate, 100 ml water, 50 ml saturated aqueous sodium chloride, dried over sodium carbonate, evaporated in vacuo and stored at 0.05 mm Hg for 1 hour. The residue was dissolved in 400 ml dry ether and hydrogen chloride added until precipitation ceased. After filtration and washing with 1 liter of dry ether, a white powder was obtained, which was dissolved in 100 ml water and made alkaline with sodium carbonate solution. The resulting oil was taken up in 2 × 200 ml ether, dried over magnesium sulfate, evaporated in vacuo and placed in vacuo overnight to give 5.4 g (45%). TLC:$R_f$(0.4), 10% MeOH in $CHCl_3$, silica gel, yellow oil crystallized on standing m.p. 98°–107°.

B. The above ester product (450 mg, 1.2 mmoles) was refluxed in 10 ml 2N hydrochloric acid for 3 hours. The reaction mixture was evaporated in vacuo and the vacuum maintained for 1 hour. The residue was taken up in 10 ml water and the pH adjusted to 6 with 2N sodium hydroxide. The resulting suspension was centrifuged until clear and the supernatant decanted and washed with 20 ml of ether, 20 ml of benzene, then evaporated in vacuo and dried with a vacuum for 1 hour. Hot absolute ethanol (2 ml) was added to the residue and the resulting brown suspension centrifuged and the supernatant decanted into 10 ml of acetone. After filtration and washing with 10 ml of a 2:1 mixture of acetone:abs. ethanol, 100 mg (22% ) of off-white crystals was obtained. TLC:$R_f$ 0.35, n-BuOH:$H_2O$:-

HOAC 8:2:2.

C. To 77 mg (0.2 mmoles) O³-(isopropylcarboxymethyl)morphine in 2 ml dry DMF at 0° was added 26.2 μl (0.2 mmoles) isobutylchloroformate and the mixture stirred under N₂ at 0° for 1 hour. To this mixture was added 31.4 mg (0.2 mmole) 3-amino-2,2,5,5-tetramethylpyrrolidinyl-1-oxyl and the mixture stirred overnight under N₂. The mixture was added to 20 ml of water and made basic with sodium carbonate solution and extracted with 2 × 20 ml benzene. The combined benzene extracts were evaporated in vacuo and the residue placed in vacuo (0.05 mm Hg) at 80° for 1 hour. The resulting residue was dissolved in 4 ml boiling cyclohexane and cooled to give pale yellow crystals upon washing with 10 ml pet. ether. TLC: R$_f$(0.3), CHCl₃:MeOH, 9:1

ESR verifies presence of radical.

Anal. Calcd. for $C_{30}H_{42}N_3O_5$: C, 68.67; H, 8.07; N, 8.01

Found: C, 70.37; H, 9.36; N, 5.56

EXAMPLE 2.7

O³-(Carbomethoxyhexamethylene-)morphine

Dry morphine (5.7 g, 20 mmoles) and 800 mg (20 mmoles) sodium hydroxide in 50 ml absolute ethanol was degassed under aspirator vacuum and refluxed under nitrogen until the sodium hydroxide had dissolved. The solution was then evaporated in vacuo and the residue dissolved in 40 ml of dry freshly distilled HMPA to which was added 4.2 g (20 mmoles) methyl ω-bromoheptanoate and 1.0 g sodium iodide. The resulting mixture was degassed and put under nitrogen with stirring at 65° for 48 hours. Upon cooling to room temperature, the mixture was poured into a slurry of ice and water (400 ml) and extracted with 3 × 100 ml ether. The combined ether extracts were washed with 100 ml 5% aqueous sodium carbonate, 100 ml water and 50 ml saturated aqueous sodium chloride and dried over anhydrous magnesium sulfate. The dried ethereal extract was stripped in vacuo and placed in 0.05 mm Hg vacuum overnight to yield a yellow oil. The oil was dissolved in dry ether (400 ml) and dry hydrogen chloride bubbled in until precipitation ceased. The white suspension was filtered and washed with 500 ml dry ether, dissolved in 25 ml water and basified with 100 ml 5% aqueous sodium carbonate. The liberated amine was taken up in 200 ml ether, dried over magnesium sulfate and stripped in vacuo. After pumping (0.05 mm Hg) overnight, 5.2 g (61%) light yellow oil was obtained. R$_f$ 0.35 (5% - MeOH/CHCl₃; silical gel) NMR (CDCl₃) 3.7 (s).

By following the procedures of the foregoing examples, the morphine derivatives can be spin labeled, to provide, for example 3-[7'-(O³''-morphinoxy)heptamido]-2,2,5,5-tetramethylpyrrolidinyl-1-oxyl.

EXAMPLE 2.8

3-[(N-normorphino)acetamindo]-2,2,5,5-tetramethylpyrrolidinyl-1-oxyl

A. Morphine (8.66 g) was acetylated with acetic anhydride (32 g) and pyridine (25 g) at room temperature overnight. After removal of the solvents by azeotroping with benzene, the residue was dissolved in dichloromethane, washed with saturated sodium chloride solution, 2.5% sodium chloride solution, 2.5% sodium carbonate solution, 2N-hydrochloric acid, and finally, saturated sodium chloride solution. Evaporation of the dichloromethane after drying over anhydrous sodium sulfate afforded heroin in a solid state (10.59 g) mp 169°–173°.

A mixture of heroin (10.59 g) and cyanogen bromide (4.3 g) in chloroform (43ml) was heated at 50° for 2 hours. The mixture was cooled in an ice water bath and then poured into ether (170 ml) and stirred for 15 minutes to give a white precipitate, which was washed with hot absolute ethanol (50 ml), and dried over phosphorous pentoxide yielding 8.02 g of cyanonorheroin. m.p. 204°–241° (lit. m.p. 235°–237°)

Cyanonorheroin (8.02 g) was heated at 50° for 5 min. in a solution of potassium hydroxide (3.0 g) in 50% aqueous ethanol (60 ml). Addition of water (180 ml) and then glacial acetic acid (8 ml) gave crystals of cyanonormorphine, which were collected on a filter, washed with water, and dried over phosphorous pentoxide in vacuo affording 6.4 g, m.p. 289° dec (lit. m.p. 288°)

B. Cyanonormorphine (15.4 g) was suspended in 6% hydrochloric acid (450 ml) and heated at 70° for 15 hours with continuous stirring. After being cooled, a precipitate was collected on a filter and dried yielding 14.8 g of N-carbomoylnormorphine, m.p. 268°. Recrystallization from water gave 10.7 g, m.p. 282°, (1st crop), 0.5 g. m.p. 281° (2nd crop) and 0.5 g, m.p. 277° (3rd crop). The mother liquor was purified by column chromatography on silica gel (120 g). Elution with a 1:50 mixture of methanol and chloroform yielded an additional 1.2 g, m.p. 277.5° after crystallization from water. The yield was 79.4%.

C. N-Carbamoylnormorphine (1 g) was gently refluxed in 6% hydrochloric acid (30 ml) for 12 hours. The resulting homogeneous solution was treated with charcoal (200 mg) at 30° for 10 min. After removal of the charcoal, powdered anhydrous sodium carbonate was added carefully to the filtrate until the solution ceased foaming. Addition of 5% sodium carbonate solution brought the pH up to 7.5 to give light gray crystals in the filtrate. The crystals were collected, washed with cold water, dried over phosphorous pentoxide in vacuo, and afforded 860 mg, m.p. 277°, (lit. m.p. 262°–263°; m.p. 276°–277°) of normorphine. Yield, 97.7%.

D. A mixture of normorphine (9.4 g, 0.0347 mole) and powdered sodium bromoacetate (7.1 g, 0.0433 mole) in absolute methanol (175 ml) was gently refluxed for 12 hours, and then cooled to room temperature. Crystals were separated and filtered, washed with cooled water and dried to yield 6.0 g, m.p. 246°. Recrystallization afforded an analytically pure N-carboxymethylnormorphine, 5.9 g, m.p. 269°–271°. Yield, 75%. Anal. Calcd. for $C_{18}H_{21}NO_6 \cdot H_2O$: C, 62.42; H, 6.10; N, 4.03 Found: C, 62.27; H, 6.12; N, 4.05.

E. N-Carboxymethylnormorphine (500 mg) was treated with acetic anhydride (7 ml) and pyridine (7 ml) at room temperature overnight. After removal of the solvents, trituration of the residue with ether gave a crystalline solid (590 mg), m.p. 258°–259°. Recrystallization from a mixture of methanol and ether afforded an analytically pure diacetate (520 mg) m.p. 266°–8°. Anal. Calcd. for $C_{22}H_{23}NO_7$: C, 63.91; H, 5.61; N, 3.39 Found: C, 63.95; H, 5.53; N, 3.31

F. To a solution of diacetyl N-carboxymethyl normorphine (411 mg), 0.943 mmole in dry dimethylformamide (8 ml) and acetonitrile (40 ml) was added 3-amino-2,2,5,5-tetramethylpyrrolidinyl-1-oxyl (193 mg, 1.14 mmoles) in acetonitrile (1 ml) and dicyclohexylcarbodiimide (2.28 mg, 1.14 mmoles) in acetonitrile (1 ml). The mixture was allowed to stir at room temperature for 20 hours. After removal of the precipitate, the filtrate was condensed to leave an oil, which was shaken with a mixture of dichloromethane and water to extract the compound. The dichloromethane layer was purified by preparative TLC. The yellow band with $R_f$ 0.52 (silica gel, 5% methanol-95% chloroform) was collected by cutting and extracted with methanol, and after removal of the solvent, the residue was dissolved in 50% aqueous ethanol containing potassium hydroxide (0.1 g), and heated at 50° for 10 minutes. To the cold solution was added 2N-hydrochloric acid to pH 8. Crystals separated out, 60 mg, which were recrystallized from aqueous ethanol, 57 mg (12.9%), m.p. 218°–221° as an analytically pure sample of 3-[2'-(N-normorphino) acetamido]-2,2,5,5-tetramethylpyrrolidinyl-1-oxyl; ESR ($H_2O$) 3 lines in ratio of 1:1:1, $a_N$ = 16.7 G. Anal. Calcd. for $C_{26}H_{34}N_3O_5$: C, 66.65; H, 7.31; N, 8.97 Found: C, 66.56; H, 7.27; N, 8.70.

G. Diacetate (see paragraph E) (200 mg. 0.463 mmole) was dissolved in dry dimethylformamide (10 ml) and cooled at 0° with stirring. To the solution was added dropwise isobutylchloroformate (127 mg, 0.926 mmole) and then triethylamine (93 mg, 0.926 mmole). After being stirred for 1.5 hours, 3-amino-2,2,5,5-tetramethylpyrrolidinyl-1-oxyl (145 mg, 1.39 mmoles) in dimethylformamide (0.5 ml) was added and stirred at room temperature overnight, and then water (50 ml) added. The mixture was extracted with dichloromethane. The extracts were washed with water and dried. Evaporation of the solvent left an oil, which was treated by preparative TLC in the same manner as above. The oil with $R_f$ 0.52 was obtained and further worked up in the same manner as above to afford yellow crystals (124 mg, m.p. 218°–221°, 57% yield).

EXAMPLE 2.9 --

Conjugation of carboxymethyl morphine with poly-L-lysine (PLL)

Poly-L-lysine hydrobromide (50 mg, Miles Lot. LY 115 A) ($1.14 \times 10^{-6}$ Mole) was suspended in 1 ml dry DMF and 0.241 ml of 1N NaOH was added. The slurry dissolved nearly completely (5 mg residue).

In a separate flask 12.4 mg (0.033 mM) of carboxymethyl morphine were dissolved in 1 ml dimethyl formamide (DMF) (less DMF will not dissolve the acid) and cooled to $-15°$. To this solution was added 3.28 g (0.033 mM) of ethyl chloroformate. The solution was stirred at $-15°$ for 20 minutes after which the poly-L-lysine solution was added followed by the addition of 2 ml of DMF used to wash the flask that contained the poly-L-lysine. A precipitate formed. The reaction was stirred overnight at 0°, diluted with water and dialyzed against distilled water (6 changes). Lyophilization gave 19 mg residue.

Determination of the Degree of Conjugation

The ultraviolet spectrum was measured at 280 nm in a 1 cm cell: d=0.25 when the concentration was 0.287 g/l. in water. $\epsilon_{CMM}^{280} = 1070$, $\epsilon_{PLL}^{280} = 0$. The degree of conjugation can be determined from this data and the formula $$d = \frac{(X\epsilon_{CMM} + \epsilon_{PLL})W}{XMW_{CMM} + MW_{PLL}}$$

where X = number of haptens per molecule, W = weight of protein conjugate per liter and MW is the molecular weight where CMM refers to the hapten and PLL refers to the protein. Since the molecular weight of the protein was 27,000

X = 30 haptens/molecule.

EXAMPLE 2.10 --

Conjugation of carboxymethyl morphine to Bovine Serum Albumin (BSA)

Carboxymethyl morphine (240 mg) suspended in 8 ml dry DMF was cooled to $-15°$ and treated with 84 $\mu$l isobutyl chloroformate. The solid dissolved while stirring for 30 minutes at $-15°$. BSA (400 mg) dissolved in 56 ml water containing 2.6 g sodium bicarbonate was added to this solution and the mixture was kept at 0° overnight. It was then dialyzed against distilled water with 4 changes of water (dialysis 1:80) and lyophilized to give 350 mg of conjugate.

Hapten concentration on the protein: $d = 0.59$ $\epsilon_{BSA}^{280} = 41600$ $\epsilon_{CMM}^{280} = 1070$ $MW_{CMM} = 327$ $MW_{BSA} = 64\,600$ X = 46.6 haptens/molecule.

EXAMPLE 2.11 --

Conjugation of N-carboxymethylnormorphine to Bovine Serum Albumin

A. To a suspended solution of N-carboxymethylnormorphine (250 mg, 0.74 mmole) in dry dimethylformamide (8 ml) was added isobutylchloroformate (124 mg, 0.89 mmole) and triethylamine (92 mg, 0.89 mmole) with stirring at $-15°$. After the mixture was continuously stirred and cooled below 0° for 1.5 hours, bovine serum albumin (426 mg, 0.37 mmole) in a cooled 0.7% sodium bicarbonate solution (100 ml) was added gradually with stirring. After the mixture was stirred in the cold room for one day, and then centrifuged (22 min, 4°, 15,500 rpm) to remove the white precipitate, the clear solution was dialyzed with distilled (1 l. $\times$ 9 times) in the cold room for 3 days. Water was evaporated below 0° in vacuo to leave fluffy white residue (450 mg).

The degree of conjugation (n) was 16 normorphines/molecule.

B. The reaction was done in the same manner as A. using instead isobutylchloroformate (299 mg, 1.63 mmoles) and triethylamine (169 mg, 1.63 mmoles), and finally gave a less soluble residue (151 mg, n = 38) than A.

EXAMPLE 3.1 --

3-(N-(1'-Phenyl-2'-propyl)glycinamido)-2,2,5,5-tetramethylpyrrolidinyl-1-oxyl

A solution of amphetamine (2 mmoles, prepared from 368 mg of the sulphate) in methanol (20 ml) was treated with sodium carbonate (106 mg, 1 mmole) and 3-(2'-iodoacetamido)-2,2,5,5-tetramethyl-1-pyrrolidinyl-1-oxyl (321 mg, 1 mmole). The reaction mixture was stirred overnight at room temperature, evaporated to dryness and the residue partitioned between water and ether. The residue obtained by evaporation of the ether was chromatographed on silica gel (8% methanol in dichloromethane) to give 187 mg (59%) of a deep-yellow mixture of oil and crystals which ran as a single spot on TLC in the above system ($R_f$ 0.5).

ESR (in water) $a_n$ 15.9 G.

EXAMPLE 3.2 --

3-[N-(1'-Phenyl-2'-propyl)glycinamido]-2,2,5,5-tetramethylpyrrolidinyl-1-oxyl

A. Amphetamine sulfate (3.68 g, 20 mmoles) was dissolved in water (50 ml) and 1N NaOH (30 ml) was added. The liberated base was extracted with ether (3 $\times$ 50 ml) and the organic layer was dried and evaporated. The residue was dissolved in dry benzene (50 ml) and diisopropylethylamine (3 ml) was added, followed by ethyl bromoacetate (2.2 ml) and the mixture refluxed for one hour. The cooled reaction mixture was cooled and filtered, and the residue which was left on evaporation of the filtrate was partitioned between ether and water. The ether layer was washed several times with water, evaporated to dryness and the residue chromatographed on silicagel. The pure ester was eluted with hexane:ether 7:3 and was obtained as an oil (3.1 g, 70%).

B. A mixture of the ester (2.5 g, 11.3 mmoles) methanol (25 ml) and 1N sodium hydroxide (25 ml) was left overnight at room temperature. The solution was concentrated to a small volume, washed with ether and the pH adjusted to 6.0. The crystallized compound that came out was recrystallized from ethanol-acetone. Two fractions were obtained: 900 mg, m.p. 222°–25°, and 450 mg, m.p. 210°–18°.

C. N-(Carboxymethyl) amphetamine hydrochloride (1.70 g, 7.9 mmoles) was powdered in a pestle and mortar and dried at 80° in a 0.05 mm Hg vacuum. The dried, well powdered material was suspended in 30 ml acetyl chloride at 0° and 2.0 g (10 mmoles) phosphorus pentachloride quickly added. After stirring for 20 minutes at 0°, the mixture was stirred for 16 hours, under $N_2$ at room temperature. Filtration under $N_2$, washing of the solid with 30 ml acetyl chloride then 2 × 50 ml pet. ether and drying under a stream of $N_2$ gave 1.9 g (97% yield) of fluffy white powder as the acid chloride.

To 1.20 g (4.83 mmoles) of the acid chloride was added a solution of 2.24 g (14.3 mmoles) 3-amino-2,2,5,5-tetramethylpyrrolidinyl-1-oxyl in 20 ml of chloroform (dry) and resulting solution stirred under $N_2$ for 2 hours. The reaction mixture was then washed with 10 ml 5% aqueous sodium carbonate, 2 × 10 ml water, dried over sodium carbonate and evaporated in vacuo. The resulting yellow oil was column chromatographed using 100 g silica and chloroform with increasing amounts of methanol as eluent to give 1.5 g (93%) of an orange oil showing one spot on TLC and an $R_f$ 0.4 (5% MeOH/CHCl$_3$, silica). ESR verifies presence of radical.

EXAMPLE 3.3 –

3-[p-(2'-Aminopropyl-1')phenoxy)acetamido]-2,2,5,5-tetramethylpyrrolidinyl-1-oxyl A. p-Hydroxyamphetamine hydrobromide (4.6 g, 20 mmoles was dissolved in a half-saturated solution of sodium chloride (30 ml) and neutralized by the addition of sodium hydroxide (800 mg, 20 mmoles). The free base was extracted with ethyl acetate, but even after complete saturation of the aqueous phase with sodium chloride, only 2.3 g of the free amine were obtained.

A solution of the above amine in trifluoroacetic anhydride (20 ml) (which was made at $-5°$) was warmed slowly to 80° (about 40 minutes). Most of the anhydride was removed by evaporation and the residue was crystallized twice from boiling water. m.p. 126°–7° (2.63 g, 45.7%). A higher yield, 70% is obtained by a direct trifluoracetylation of the hydrobromide. Anal. Calcd. for $C_{11}H_{12}F_3NO_2$: C, 53.44; H, 4.89; N, 5.66; F, 23.05 Found: C, 53.59; H, 4.92; N, 5.63; F, 23.10.

B. N-Trifluoracetamido p-hydroxyamphetamine (96 mg, 0.33 mmoles) was added, under argon, to a suspension of sodium hydride (16 mg, 0.33 mmoles) in dry DMF (5 ml) at 0°. After stirring at room temperature for 40 minutes, 3-(2-iodoacetamido)-2,2,5,5-tetramethyl-1-pyrrolidinyloxyl (108 mg, 0.33 mmoles) was added and the reaction mixture was stirred at room temperature for 6 hours. The DMF was evaporated, and the residue was partitioned between water and dichloromethane. The yellow gum which was obtained on evaporation of the dichloromethane was dissolved in a few ml of a 1:1 mixture of conc. ammonia and methanol and the solution left overnight. The solvent was evaporated and the residue partitioned between ether and 0.1N sodium hydroxide. The residue which was left on evaporation of the ether (mixture of oil and crystals) was pure on TLC (silica, dichloromethane:-methanol 4:1, ethyl acetate: methanol 1:1. Alumina: 5 and 7% methanol in chloroform), 54 mg, 46%. An attempt to purify the compound by prep. TLC (methanol:chloroform 1:1) gave 30 mg of an oil, which had the characteristic 3-line ESR. Anal. Calcd. for $C_{19}H_{30}N_3O_3$: C, 65.48; H, 8.68; N, 12.06 Found: C, 63.16; H, 8.64; N, 11.11

EXAMPLE 3.4 –

[4'-(1''-Phenyl-2''-propylamino)crotonamido]-2,2,5,5-tetramethylpyrrolidinyl-1-oxyl A. Amphetamine sulfate (2.76 g) was treated with 2N-sodium hydroxide solution and dichloromethane to give free amphetamine (2.03 g)

A mixture of amphetamine (2.03 g, 0.0151 mole) ethyl 4-bromocrotonate (2.8 g, 0.0147 mole) and diisopropylethylamine (3.90 g, 0.0302 mole) was heated in dry benzene (15 ml) at 50° for 1.5 hours. After a precipitate was removed from the cooled reaction mixture, the filtrate was washed with water, dried and evaporated to leave an oil (3.3 g). This oil was separated by preparative TLC (silica gel, ether). After being worked, the fraction with $R_f$ value 0.8 gave an oily monoalkylated compound (1.76 g, 47.5% yield).

B. The above product (300 mg, 0.833 mmole) in a 1:1 mixture (5 ml) of ethanol and water containing sodium hydroxide (0.1 g) was kept at room temperature overnight. The reaction mixture was washed with dichloromethane after evaporation of ethanol, and then acidified with conc. hydrochloric acid. The acidic solution was washed with dichloromethane, and evaporated to dryness in vacuo. The residue was treated with a 1:9 mixture of absolute methanol and dry tetrahydrofuran for removal of sodium chloride as a precipitate. The filtrate was evaporated to leave an oil, which on crystallization from a mixture of acetone and tetrahydrofuran gave white crystals of 4-(1'-phenyl-2'-propylamino)crotonic acid hydrochloride (290 mg, 93.5% yield, m.p. 184°–5°). Recrystallization from the same solvents afforded an analytical sample, m.p. 184°–5°. Anal. Calcd. for $C_{13}H_{18}O_2NCl$: C, 61.05; H, 7.09; N, 5.48; Cl, 13.86 Found: C, 60.96; H, 7.07; N, 5.49; Cl, 13.91.

C. To a suspended solution of the above product (126 mg, 0.493 mmole) and 3-amino-2,2,5,5-tetramethylpyrrolidinyl-1-oxyl (85 mg, 0.493 mmole) in a solution of dimethylformamide (5 ml) and acetonitrile (5 ml) was added in a dropwise manner, a mixture of dicyclohexylcarbodiimide (124 mg, 0.592 mmole) and additional pyrrolidinyl-1-oxyl compound (255 mg, 1.480 mmole) in acetonitrile (1 ml). The mixture was stirred at room temperature overnight, and then heated at 50° for 3 minutes giving a clear solution. The cooled mixture gave a precipitate which was filtered off. The filtrate was evaporated under reduced pressure to leave an oil. This oil was dissolved in ether, and, after being washed with water, dried over anhydrous sodium sulfate. Evaporation of the solvent gave an oil, which was purified by preparative TCL (silica gel, 5% methanol -- 95% chloroform). After extraction of a yellow band ($R_f$ 0.35) and evaporation of the solvents, the residual oil was dissolved in dichloromethane to be washed with water and to be dried over anhydrous sodium sulfate. Evaporation of dichloromethane gave a light yellow oil (50 mg, 27.3% yield) as the desired product.

EXAMPLE 3.5

3-[5'-(1''-Phenyl-2''-propylamino)pentanamido]-2,2,5,5-tetramethylpyrridolinyl-1-oxyl A. Amphetamine sulfate (2.34 g, 0.0133 mole) was treated with 2N sodium hydroxide solution and dichloromethane to give free amphetamine (1.8 g). A mixture of this amphetamine (1.80 g, 0.0133 mole), ethyl 5-bromovalerate (2.78 g, 0.0133 mole) and diisopropylethylamine (3.45 g, 0.0266 mole) was refluxed in dry benzene for 10 hours. The cooled solution gave a precipitate of hydrobromide salt of diisopropylethylamine, which was removed by suction filtration. The filtrate was washed with water, dried with anhydrous sodium carbonate and evaporated to dryness. The oil (3.20 g) obtained was separated by preparative TLC (silica gel, 5% methanol -- 95% ether). Each fraction was extracted with methanol. The extracts were dried with anhydrous sodium carbonate and evaporated to dryness to give oils. One fraction ($R_f$ 0.45) gave a colorless oil (1.44 g) of N-(4'-ethoxycarbonylbutyl) amphetamine in 41% yield.

Anal. Cald. for $C_{16}H_{25}O_2N$: C, 72.96; H, 9.57; N, 5.32 Found: C, 72.97; N, 9.51; N, 5.32.

B. The ethyl ester (300 mg) prepared above in 50% aqueous EtOH, (5ml) containing 2% NaOH was kept at room temperature overnight. After evaporation of EtOH, the residual solution was washed with $CH_2Cl_2$ and then evaporated under reduced pressure to dryness. The residue was treated with dry THF to remove crystalline NaCl, and after evaporation of THF, hydroscopic needle crystal (250 mg) of the aminoacid hydrochloride m.p. 100°–115° were obtained from a 1:1 mixture of THF-acetone in 81% yield. Trituration with acetone converted the hygroscopic crystals to non-hygroscopic powdered crystals, m.p. 119° for analysis.

Anal. Cald. for $C_{14}H_{22}ONCl$: C, 61.87; H, 8.02; N, 5.10; Cl, 13.04 Found: C, 61.82; H, 8.02; N, 5.10; Cl, 12.92.

C. To a suspended solution of the above product (136 mg, 0.500 mmole) and 3-amino-2,2,5,5-tetramethylpyrrolidinyl-1-oxyl (85 mg, 0.500 mmole) in a mixture of DMF (5 ml) and $CH_3CN$ (5 ml) was added a mixture of dicyclohexylcarbodiimide (124 mg, 0.600 mmole) and 3-amino-2,2,5,5-tetramethylpyrrolidinyl-1-oxyl (255 mg, 1.5 mmole) in $CH_3CN$ (1 ml). The mixture was stirred at room temperature for 15 hours, and then heated at 50° for 3 minutes, giving a clear solution. The cooled mixture gave a precipitate which was filtered off. The filtrate was evaporated under reduced pressure to leave an oil. This oil was worked up as usual and purified by preparative TLC (silica gel, ether containing 5% MeOH). The yellow band with $R_f$ value of 0.60 was collected and extracted with 5% MeOH-ether, and worked up as usual, affording a light yellow oil, (40 mg, 20.6% yield) of the desired product. ESR ($H_2O$), 3 lines in ratio of 1=1=1, $A_N$ = 16.8 G Anal. Cald. for $C_{22}H_{36}O_2N_3$: C, 70.55; H, 9.69; N, 11.22

Found: C, 68.98; H, 9.70; N, 11.23.

EXAMPLE 3.6

N-trifluoroacetyl, N-methyl p-(2'-aminopropyl-1')-phenoxyacetic acid

A. A mixture of N-TFA-p-hydroxyamphetamine (0.5 g, 2 mmoles) (TFA - trifluoroacetyl), potassium carbonate (anhydrous, 1.5 g), methyl chloroacetate (1 ml) and dry acetone (30 ml) was refluxed overnight with exclusion of moisture. The cooled reaction mixture was filtered and the filtrate evaporated to give a crystalline mass. Recrystallization from chloroform-hexane gave long needles, m.p. 105°–6° (555 mg).

Anal. Calcd. for $C_{14}H_{16}NO_4F_3$: C, 52.66; H, 5.05; N, 4.38; F, 17.85 Found: C, 54.52; H, 5.48; N, 4.05; F, 17.10.

B. To a refluxing mixture of the methyl ester (160 mg, 0.5 mmole) prepared above and methyl iodide (285 mg, 2 mmole) in dry acetone (5 ml), powdered potassium hydroxide (112 mg, 2 mmole) was added, and the heating was continued for 8 minutes. Acetic acid (2 ml) was added to the cooled (ice) reaction mixture and the solvent evaporated to dryness. The residue was purified by prep. TLC (silica, ether) to give 95 mg of an oil.

C. The crude product prepared above (~1 g) was mixed with 1N sodium hydroxide (30 ml) and the mixture was kept at 80° for one hour. The brown residue which was left on evaporation of the solvent was taken up in 2N hydrochloric acid and the clear solution was evaporated to dryness. The well-dried ($P_2O_5$) residue was extracted with boiling iso-propanol (2 × 50 ml) and the brown solution was treated with Norite and filtered. Evaporation left a light brown oil. It was mixed with trifluoroacetic anhydride (20 ml) and the mixture was refluxed for one hr. Evaporation left a gummy residue which was treated with boiling water and then extracted with ether. The ether was dried and evaporated to give an oil (600 mg).

Anal. Calcd. for $C_{14}H_{16}NO_4F_3$: C, 52.66; H, 5.05; N, 4.38; F, 17.85 Found: C, 49.84; H, 5.07; N, 3.58.

Following the procedure of Example 3.2 the carboxylic acid can be spin labelled with 3-amino-2,2,5,5-tetramethylpyrrolidinyl-1-oxyl and the trifluoroacetyl group removed from the amino group as described previously to provide the product 3-[p-(2'-methylaminopropyl-1')phenoxyacetamido]-2,2,5,5-tetramethylpyrrolidinyl-1-oxyl.

EXAMPLE 3.7

N-Trifluoroacetyl 4-amino-5-phenylpentanoic acid

A. A mixture of 5-phenyllevulinic acid [prepared as described by Y. Lzumi, et al, Bull. Chem. Soc. Japan, 38 (8) 1338-40 (1965] (4.0 g, 20.6 mmoles), ammonium acetate (15.4 g), sodium cyanoborohydride (0.780 g) and methanol (80 ml) was stirred for 4 days at room temperature. The brown reaction mixture was acidified and after 1 hour it was evaporated to dryness. The residue was partitioned between water and ether and the water was evaporated to dryness. The residue was extracted with THF: MeOH 9:1 [2 × 50 ml], the extract evaporated and the residue was taken up in dichloromethane, which was then filtered and the filtrate evaporated. The residue was dissolved in ethanol, and the brown color of the solution was removed with Norite. The ethanol was evaporated and the residue crystallized from dichloromethane-ether. A white solid was obtained (3.73 g) m.p. 120°–125°. The solid was suspended again in dichloromethane, and the insoluble fraction was filtered off. That fraction was recrystallized several times from ethanol-ether to give 1.46 g of a white solid, m.p. 145°–7° (Lit. m.p. 129.5°–32.2°: Munemitsu Tomeda, et al., C. A. 67, 2960, [1967]).

The dichloromethane-soluble fraction was mixed with conc. HCl (30 ml) and the mixture was refluxed for one hour. The residue which was left on evaporation of the acid was crystallized from ethanol-ether, and it had the same $R_f$ on TLC (silica, methanol: ethylacetate:acetic acid 5:4:1) as the compound which was not soluble in dichloromethane, m.p. 145°–7°. Total yield: 2.72 g, 57.5%

B. Ethyl trifluorothioacetate (0.25 ml) was added to a solution of the amino acid (230 mg, 1 mmole) in 1N sodium hydroxide (2 ml), and the heterogeneous mixture stirred at room temperature for 4.5 hours. The pH at the beginning of the reaction was 9.5, and a few drops of 1N sodium hydroxide were added from time to time to keep the mixture at that pH. The crystalline reaction product which came out of the solution was filtered, washed with a little water and recrystallized once from boiling water to give 73 mg of the protected amino acid 26.5%, m.p. 126°–7°.

Anal. Calcd. for $C_{13}H_{14}NO_3F_3$: C, 53.98; H, 4.87; N, 4.84; F, 19.70 Found: C, 53.75, 53.85; H, 4.96, 2.85; N, 4.70; F, 18.8.

Following prior procedures, the product can be spin labeled with 3-amino-2,2,5,5-tetramethylpyrrolidinyl-1-oxyl to provide the spin labeled amphetamine derivative 3-(4'-amino-5 phenylpentanamido)-2,2,5,5-tetramethylpyrrolidinyl-1-oxyl.

EXAMPLE 3.8

4-Methylamino-5-phenylpentanoic acid

A. A mixture of 5-phenyllevulinic acid (4.0 g, 206 mmoles), methylamine hydrochloride (6.75 g), sodium cyanoborohydride (1.0 g) and methanol (100 ml) was stirred at room temperature for 4 days, then acidified to pH 1.0 and evaporated to dryness. The residue was partitioned between water and ether, and the water phase was evaporated to dryness. The residue was extracted with dichloromethane (2 × 250 ml) which was then dried and evaporated. The residue was re-dissolved in dichloromethane, the solution filtered from some insolubles and evaporated. The residue was crystallized by a slow addition of ether to its solution in ethanol to give methyl 4-methylamino-5-phenylpentanoate hydrochloride. m.p. 117°–20°.

B. A solution of the above product (200 mg, 0.78 mmoles) in conc. hydrochloric acid (5 ml) was refluxed for one hour. The residue which was left after evaporation was crystallized from ethanol-ether to give 150 mg (79%) of the pure acid as the hydrochloride, m.p. 128°–9°.

Anal. Calcd. for $C_{12}H_{18}NO_2Cl$: C, 59.13; H, 7.44; N, 5.74; Cl, 14.54 Found: C, 59.20; H, 7.35; N, 5.55; Cl, 14.72.

The above product can be spin labeled according to prior procedures with 3-amino-2,2,5,5-tetramethylpyrrolidinyl-1-oxyl to provide 3-(4'-methylamino-5'-phenylpentanamido)-2,2,5,5-tetramethylpyrrolidinyl-1-oxyl.

EXAMPLE 3.9

3-Methylamino-4-phenylbutyric acid

A. A mixture of freshly-distilled phenylacetaldehyde (24 g, 0.24 moles) monoethyl malonate (60 g, 0.455 moles) dry pyridine (100 ml) and piperidine (2.5 ml) added in that order, was stirred at room temperature for 48 hours. Most of the solvent was evaporated out and the residue partitioned between water and ether. The organic phase was washed with water, dil. HCl and water. The residue which was left on evaporation of the ether was distilled. b.p. 112°–15°/0.4mm Hg. Yield: 25 g. (The preparation is according to H. Moureu, P. Chovin and L. Petit, Bull. Soc. Chem. France, 1951, 203)

B. Methylamine (liquid, 40 g) was added to a solution of the above ester (10 g, 52.6 mmoles) in methanol (400 ml) and the reaction mixture was left for two days at room temperature. The solvent was evaporated and the residue extracted with dil. HCl. The acid was washed with ether and made strongly alkaline with KOH. The oil which separated out was extracted with ether. Drying and evaporation of the ether yielded the crude amide as a yellow oil (5 g). The oil was dissolved in 6N HCl (55 ml) and the clear solution was refluxed for 6 hours and evaporated to dryness. The solid residue was dissolved in 2N NaOH (50 ml) and the solution evaporated to dryness. The solid residue was dissolved in conc. HCl (20 ml) and the solution was evaporated again to dryness. The residue was extracted with boiling abs. ethanol (80 ml), the ethanol was evaporated and the residue dissolved in boiling isopropanol and the solution filtered and concentrated to about half the volume (40 ml). On cooling, the amino acid (as the hydrochloride) crystallized out, and addition of a small amount of ether completed the crystallization. The pure amino acid has a m.p. 179°–180° (2.97 g, 24.5% from the unsaturated ester).

Anal. Calcd. for $C_{11}H_{16}NO_2Cl$: C, 57.52; H, 7.01; N, 6.09; Cl, 15.43 C, 57.74; H, 7.00; N, 6.02; Cl, 15.46.

The above product can be spin labeled according to prior procedures with 3-amino-2,2,5,5-tetramethylpyrrolidinyl-1-oxyl to provide 3-(3'-methylamino-4'-phenylbutyramido)-2,2,5,5-tetramethylpyrrolidinyl-1-oxyl.

EXAMPLE 3.10

Conjugate of N-carboxymethyl amphetamine and bovine serum albumin (BSA)

A. Amphetamine sulphate (3.68 g, 20 mmoles of amine) was dissolved in 0.5 N sodium hydroxide (80 ml). The alkaline solution was extracted with ether, the ether dried and evaporated. The residue was dissolved in benzene (50 ml) and diisopropylethylamine (3 ml) was added followed by ethyl bromoacetate (2.2 ml, 20 mmoles). The reaction mixture was refluxed for one hour, cooled, filtered and the filtrate evaporated. The residue was taken up in ether, washed several times with water, the ether dried and evaporated. The pure amino-ester was obtained by column chromatography on silica gel (hexane: ether 7:3). Yield 3.1 g (70%). NMR and IR agree with the structure.

B. The amino-ester (2.5 g, 11.3 mmoles) was dissolved in 1:1 mixture of methanol and 1N sodium hydroxide (50 ml) and left at room temperature overnight. The mixture was evaporated to a small volume, washed twice with ether (2 × 25 ml) and acidified to pH 6 with conc. HCl. The crystals that separated out were recrystallized from ether-acetone to give two fractions: 900 mg, m.p. 222–25 (m.p. lit. 220°–5°, Tetra. Letters, 1966, 4603-7) and 450 mg, m.p. 210°–218°. Only the first fraction was used for further reactions $\lambda_{max}{}^{H_2O}$ 257, $\epsilon$=159.

C. Amphetamine-carboxylic acid (700 mg, 3.8 mmoles) was suspended in dry dioxane at 40° (50 ml) and phosgene (12.5 wt. % in benzene, 20ml) was added in one portion. The reaction mixture was stirred at 40°–50° for 3 ½ hours, evaporated to dryness, and re-dissolved in dry dioxane (20 ml). This solution was kept in ice for the next step.

D. The above solution was added in 4 portions during ½ hour to a stirred solution of BSA (2 g) in 100 ml 2% NaHCO$_3$ solution at 0° C. The reaction mixture was kept for 24 hours at 0° and 18 hours at room temperature. It was dialyzed for 2 days against 35 l. of water at 0° and lyophylized. The volume of the dialysis solution at the end was 200 ml; 10 ml of it contained 110 mg — total yield 2.2 g. The actual amount of conjugate isolated was 1.91 g. The degree of conjugation (from UV) was estimated to be approximately 76 units of amphetamine/BSA.

EXAMPLE 3.11

Conjugate of 3-methylamino-4-phenylbutyric acid and bovine serum albumin (BSA)

A. A solution of phosgene in benzene (about 12%, 10 ml) was added to a suspension of the hydrochloride of 3-methylamino-4-phenylbutyric acid (Example 3.9) (460 mg, 2 mmoles) in dry dioxane (40 ml). The mixture was stirred at 50°–70° for 0.5 hour at which time all of the amino acid went into solution. More phosgene-solution was added (10 ml) and after 0.5 hour at the above temperature, the reaction mixture was cooled and evaporated to dryness. The light, yellow-brown oil was dissolved (under argon) in dry dioxane (30 ml). Triethylamine (0.28 ml, 2 mmoles) was added and the mixture was stirred for one hour at about 10°. This reaction mixture was used, without any further manipulations in the next step.

B. The reaction mixture containing the N-carboxy anhydride prepared above was added, in one portion, to a solution of BSA (1.4 g) in a 2% sodium bicarbonate solution (100 ml) cooled in an ice-bath. The mixture was stirred overnight at 0°, filtered, dialyzed for 4 days and lyophilyzed to give 1.10 g of the conjugate. The degree of conjugation was estimated to be 60 from a calibration curve.

EXAMPLE 3.12

Conjugate of p-(2-Amino-and 2-methylaminopropyl-1)-phenoxyacetic acid and bovine serum albumin (BSA)

A. p-(Aminopropyl-1)phenoxyacetic acid (0.5 g, 2.4 mmoles) was suspended in trifluoroacetic anhydride (3.5 ml) and the mixture warmed slowly to 80° (at 70° all was in solution). The clear solution was cooled to room temperature and cold water (30 ml) was added. The crystalline product was filtered and washed with a little water and dried. Yield 614 mg, 84%, m.p. 173°–4°. Analytical sample was recrystallized from aqueous methanol, m.p. 174°–5°.

Anal. Calcd. for $C_{13}H_{14}NO_4F_3$: C, 51.15; H, 4.62; N, 4.58; F, 18.67 Found: C, 50.99; H, 4.61; N, 4,76; F, 18.62.

B. To a solution of N-trifluoroacetyl p(2-aminopropyl-1)phenoxyacetic acid (475 mg, 1.5 mmoles) in dry DMF (4 ml) cooled in ice-salt bath (10°), dry triethylamine (0.21 ml, 1.5 mmoles) was added and after stirring for two minutes, isobutyl chloroformate (0.19 ml, 1.5 mmoles) was added. The reaction mixture was stirred for 15 minutes at −10° to −6°, and then 15 minutes at 0°. The mixed anhydride thus obtained was added to a fast-stirred solution of BSA (1.5 g) in a mixture of water (200 ml), sodium bicarbonate (9.5 g) and methanol (90 ml), which was cooled in ice. The clear solution was kept overnight at 0°. Piperidine (30 ml) was added and the mixture was stirred at 0° for 2 hours to remove the trifluoroacetyl protecting group. The conjugate was purified by dialysis and gel-filtration.

Determination of the degree of conjugation was based on the UV spectrum of the purified conjugate, taken in 0.1N sodium hydroxide. The average degree of conjugation was found to be 14.2.

C. The above procedure was followed to prepare the N-methyl analog. The amounts were: 350 mg (1.1 mmoles) of the N-trifluoroacetyl p-(3-methylaminopropyl-1)phenoxyacetic acid and one g of BSA. The conjugate was purified by dialysis (4 days). The yield was 700 mg, and the degree of conjugation, which was calculated from the UV spectrum of the conjugate was found to be 9.

EXAMPLE 3.13

Conjugation of 4-amino-and 4-methylamino-5-phenylpentanoic acid

The mixed anhydride of N-trifluoroacetyl 4-amino-5-phenylpentanoic acid was prepared as described previously from 415 mg, (1.43 mmoles) of the acid, 0.2 ml triethylamine and 0.19 ml of isobutyl chloroformate. The DMF solution of the mixed anhydride was added, in one portion, to a solution of BSA (15 g) in a mixture of water (200 ml), sodium bicarbonate (9.5 g) and methanol (90 ml) and cooled in an ice bath. After stirring for 24 hours at 0°, the reaction mixture was worked up as described previously in Example 3.12 to give 1.20 g of the conjugate. The degree of conjugation was estimated from a calibration curve, to be 18 molecules of the amino acid per BSA.

EXAMPLE 3.14

Conjugation of N-carboxymethylamphetamine to bovine serum albumin (BSA)

A. N-Carboxymethyl amphetamine (700 mg, 3.03 mmoles) was suspended in dry dioxane (50 ml) and a solution of phosgene in benzene ($\approx$12% phosgene, 20 ml) was added. The reaction mixture was stirred at room temperature until all the amino acid went into solution (2.5 hours) and an additional hour at 40°. The reaction mixture was evaporated to dryness and the residue dissolved in dry dioxane and the solution kept in ice for the next step.

B. To an ice cooled solution of BSA (2 g) in 2% sodium bicarbonate (100 ml), the above product was added in four portions during 30 minutes. The reaction mixture was stirred for 24 hours at 0° and at room temperature for 18 hours. Dialysis for 2 days against distilled water (35 l.) followed by lyophylization yielded 2.2 g of the conjugate. The degree of conjugation was estimated from a calibration curve to be 56.

EXAMPLE 4.1

N-Carboxymethyl phenobarbitone

A. 1. Sodium phenobarbital, (the sodium salt of phenobarbitone) (5.8 g, 0.02 moles), methyl chloroacetate, (2.16 g, 0.02 moles), methanol (14 ml) and a catalytic amount of DMF (1 ml) were refluxed for 2 hours. A white precipitate separated out during this period. The reaction mixture was cooled to room temperature and filtered. The methanolic filtrate was evaporated to dryness to yield about 5 g of a gummy material which solidified on standing. (The precipitate from the above filtration partially dissolved when washed with distilled water. The water-insoluble material, about 50 mg, proved to be the dialkylated product).

The solidified material was stirred with 20 ml of 1N NaOH solution for 15 minutes and then filtered. This separates the alkali-insoluble dialkylated material (1.1 g) from the alkali-soluble derivatives of the monoalkylated product and unreacted phenobarbitone. Purification of the dialkylated material by column chromatography on silica gel (elution with chloroform) yielded the analytical sample as gum which crystallized on standing.

Anal. Calcd. for $C_{18}H_{20}N_2O_7$: C, 57.44; H, 5.35; N, 7.44 Found: C, 57.05; H, 5.39; N, 7.26 The alkaline filtrate was acidified with conc. HCl to a pH ~2 and the white gummy precipitate formed was taken up in methylene chloride.

Drying ($MgSO_4$) and evaporation of the organic solvent yielded ~4 g of gummy material. This was dissolved in benzene and chromatographed over a column of silica gel (40 g). Elution was with chloroform and 100 ml fractions were collected. (The progress of the chromatography was followed by TLC, since the dialkylated product has an $R_f$~0.9, the monoalkylated material $R_f$~0.6 and phenobarbitone $R_f$~0.1 with chloroform/methanol 95:5.)

Fractions 2–5 combined yielded on evaporation 1.6 g of a gum which solidified on standing. Trituration with petroleum ether and filtration yielded 1.5 g of a white powder which was shown by NMR to be the required monoalkylated derivative.

Anal. Calcd. for $C_{15}H_{16}N_2O_5$: C, 59.20; H, 5.30; N, 9.20 Found: C, 59.52; H, 5.34; N, 9.60.

A. 2. The monoester prepared above (1 g) was refluxed with 10 ml of 20% HCl solution for 3.5 hours. The cooled reaction mixture was diluted with water (20 ml) and extracted with ether. Evaporation of the ether extract yielded 0.98 g of a colorless gum which very slowly solidified on standing. NMR and TLC showed that complete hydrolysis had occurred to the acid.

A pure sample of the acid was prepared by preparative TLC, with chloroform/methanol (5:1) as eluent.

B. A solution of sodium phenobarbitone (8.8 g, 35 mmoles), and sodium chloroacetate (4.5 g, 38 mmoles) in methanol (250 ml) was mixed with a solution of $CaCl_2$ (3 g) in methanol (50 ml). After addition of 5 ml DMF the mixture was refluxed for 36 hours. After removal of the solvent, the residue was treated with water (100 ml) and acidified with conc. HCl followed by extraction with chloroform. The organic layer was evaporated to dryness and the residue treated with 10% $NaHCO_3$ solution. Extraction with chloroform and evaporation of the organic layer yielded 3 g of unreacted phenobarbital. The bicarbonate layer was acidified with conc. HCl and extracted with chloroform. Evaporation of the dried ($MgSO_4$) chloroform yielded 4.5 g of a gummy material which solidified slowly on standing. TLC and NMR showed this to be nearly pure monoacid with only traces of unreacted phenobarbitone and dialkylated derivative.

EXAMPLE 4.2

5-(2'-Pentyl)-5-(carboxymethyl)barbituric acid

A. Ozone was passed through a cooled (dry ice/acetone) solution of sodium secobarbital (2.6 g, 0.01 mole) in methanol (250 ml). After ozonolysis was completed (positive KI test) nitrogen was passed through the reaction mixture to remove all traces of ozone and then dimethyl sulfide (7 ml) was added to the cold solution with a syringe and the solution allowed to stand overnight at room temperature. After evaporation of the solvent, the residue was diluted with water (20 ml), acidified with conc. HCl and extracted with chloroform (3 × 20 ml). The chloroform extract was dried ($MgSO_4$) and evaporated to yield 2.4 g of gummy colorless material.

This was used without further purification in the reaction with malonic acid.

B. The same reaction was repeated with 6.23 g of seconal (the free acid) and the yield was 6 g of crystalline aldehyde.

C. A mixture of the aldehyde prepared above (0.48 g, 2 mmoles) in ethanol (60 ml), sodium hydroxide (0.6 g), water (60 ml) and freshly prepared silver oxide (obtained from a solution of 1.36 g $AgNO_3$ in water and excess 2N NaOH solution, filtered and the precipitate washed with distilled water) was refluxed for 5 hours. The reaction mixture was filtered hot and the solution was concentrated to a volume of about 10 ml. This was acidified with conc. HCl whereupon a white precipitate separated out, which was collected by filtration. The filtrate was extracted with ether and the residue obtained from the ether evaporation was combined with the white precipitate from the filtration. The combined solids were then treated with excess 10% $NaHCO_3$ solution and the mixture extracted with chloroform to remove unreacted aldehyde. The bicarbonate aqueous layer was then carefully acidified with conc. HCl and extracted with ether (2 × 56 ml) and then chloroform (2 × 50 ml). The combined organic layers were evaporated to yield 0.38 g of a white solid. NMR showed this to be the expected carboxymethyl derivative. Crystallization from $CCl_4$/ether yielded the analytical sample.

Anal. Calcd. for $C_{11}H_{16}N_2O_5$: C, 51.55; H, 6.29; N, 10.93 Found: C, 51.33; H, 6.21; N, 10.93.

EXAMPLE 4.3

5-(2'-Pentyl)-5-(3'-carboxyprop-2'-enyl-1')barbituric acid

A. The pure aldehyde prepared as in Example 4.2 (0.24g, 1 mmole), malonic acid (0.21 g, 2 mmoles), 20 ml pyridine and 1 ml piperidine were refluxed together for 5 hours. The solvent was removed on the flash evaporator and the residue dissolved in 10% sodium bicarbonate solution. The bicarbonate solution was washed with ether (3 × 20 ml) and then acidified with conc. HCl. Extraction with ether (2 × 20 ml) and then with chloroform (2 × 25 ml) followed by drying ($MgSO_4$) and evaporation of the combined organic layers yielded 0.23 g (80% yield) of a white solid shown by NMR to be the desired acid. Recrystallization from $CHCl_3/CCl_4$ yielded 0.16 g of pure material.

Anal. Calcd. for $C_{13}H_{18}N_2O_5$: C, 55.31; H, 6.42; N, 9.92. C, 55.06; H, 6.32; N, 9.85.

EXAMPLE 4.4

N-Carboxymethyl seconal

Sodium seconal (2 g) was dissolved in a small volume of water and mixed with a conc. aqueous solution of $CaCl_2$. The white precipitate which separated out was filtered, washed with water, then with ether and air dried on the filter funnel. A white powder (2.3 g) assumed to be the Ca salt of seconal was collected. This was dissolved in methanol (50 ml) and, after addition of 1.1 g of sodium chloroacetate and 2 ml DMF, was refluxed for 6 hours, and then allowed to stir at room temperature overnight. After evaporation of the solvent, the residue was treated with water (30 ml) and acidified with conc. HCl. The mixture was extracted with chloroform (3 × 30 ml) and the organic layer evaporated to dryness. The residue was stirred with 30 ml of 10% $NaHCO_3$ solution and then extracted with chloroform. The chloroform extract, on evaporation, yielded 0.82 g of unreacted seconal. The bicarbonate layer was acidified and extracted with chloroform. The organic layer upon evaporation yielded 0.86 g of a gummy material which had an NMR spectrum consistent with the expected acid. This acid was redissolved in 10% $NaHCO_3$ and the above procedure of acidification and chloroform extraction was repeated, leading to a yield of 0.62 g of a colorless gum which slowly crystallized on standing. This material was analytically pure.

Anal Calcd. for $C_{14}H_{20}N_2O_5$: C, 56.74; H, 6.80; N, 9.45 Found: C, 56.34; H, 6.77, N, 9.32.

EXAMPLE 4.5

N-(1-Carboxyethyl)phenobarbitone

Sodium phenobarbital (5.08 g, 20 mmoles) dissolved in DMF (125 ml) was mixed with a solution of $CaCl_2$ dissolved in DMF (75 ml). After addition of ethyl 2-bromopropionate (3.96 g, 22 mmoles) the mixture was heated to 140° for 3 hours. After cooling, the reaction mixture was poured over ice, acidified with conc. HCl and extracted with ether (4 × 75 ml). Evaporation of the ether yielded 6 g of oily residue. This was treated with excess 10% $Na_2CO_3$ solution and extracted with ether. Evaporation of the ether extract yielded 2.3 g of gummy material, which showed one spot on TLC and had an NMR spectrum compatible with the N,N-dialkylated material.

The carbonate layer was acidified with conc. HCl and extracted with ether. Evaporation of the ether extract yielded 3.4 g of a gummy residue which showed two spots on TLC, unreacted phenobarbitone and N-monoalkylated compound. The NMR spectrum confirmed the TLC result. The above mixture was then refluxed for 3.5 hours with 50 ml of 20% HCl solution. After cooling, the reaction mixture was extracted with ether (2 × 75 ml) and then with chloroform (2 × 75 ml). Evaporation of the combined organic layers left a residue which was treated with 10% $NaHCO_3$ solution and then extracted with ether to separate the carboxylic acid derivative from unhydrolyzed ester and the unreacted phenobarbitone.

The bicarbonate solution as acidified with conc. HCl and extracted with ether (2 × 50 ml) and with chloroform (2 × 50 ml). After evaporation of the solvents there remained 1.0 g of a white solid which was very hygroscopic and hand an NMR spectrum compatible with the structure of the desired product.

The analytical sample was dried at 56°/0.1 mm Hg for 62 hours.

Anal. Calcd. for $C_{15}H_{16}N_2O_5$: C, 59.20; H, 5.30; N, 9.20 Found: C, 59.59; H, 5.52; N, 9.02.

EXAMPLE 4.6

N-Carboxymethyl glutethimide

Sodium hydride (0.85 g of a 50% oil paste, 18 mmoles) was added in small amounts to a stirred solution of glutethimide, (3.7 g, 17 mmoles) in dry DMF (10 ml). Stirring was continued for about 5 minutes, when gas evolution was no longer observed. Sodium chloroacetate (2.2 g) was then added and the reaction mixture was stirred with heating in an oil bath at 100° for 3 hours. After cooling, the reaction mixture was diluted with 50 ml water, acidified with conc. HCl and then poured into 200 ml ether. The ether layer was separated and washed with water (2 × 50 ml). The organic layer was dried ($MgSO_4$) and evaporated to yield 3.4 g of a white solid. Recrystallization from carbon tetrachloride/methylene chloride yielded the analytical sample of the acid.

Anal. Calcd. for $C_{15}H_{17}NO_4$: C, 65.44; H, 6.22; N, 5.08 Found: C, 64.92; H, 6.20; N, 4.99.

EXAMPLE 4.7

General procedure for spin labeling carboxy derivatized compounds

A solution of dicyclohexyldiimide (DCC) (1 mmole) in methylene chloride (5 ml) was added to a solution of the carboxy derivatized compound (1 mmole) and 3-amino-2,2,5,5-tetramethyl-1-pyrrolidinyl-1-oxyl (spin label) (1 mmole) in methylene chloride (10 ml). The reaction mixture was stirred at room temperature for 4–6 hours during which time a white precipitate of dicyclohexyl urea (DCU) separated out. The precipitate was removed by filtration and the filtrate evaporated to dryness. The residue was triturated with 10% $NaHCO_3$ solution (to dissolve unreacted carboxy derivative) and extracted with ether. The ether extract, which contained unreacted spin label and the spin labeled product, was extracted with several portions of sodium carbonate solution, which dissolved the spin labeled product. The carbonate layer was carefully acidified with conc. HCl and immediately extracted with ether. Evaporation of the ether yielded the crude spin labeled product. This was purified by preparative TCL (silica) (elution with chloroform/methanol, 95:5).

The following table indicates the spin labeled compounds which were prepared in accordance with the above procedure and their elemental analyses.

| Precursor Compound Example No. | Emipirical Formula | SPIN LABELED DERIVATIVES Analysis %C | | %H | | %N | |
|---|---|---|---|---|---|---|---|
| | | Calcd. | Found | Calcd. | Found | Calcd. | Found |
| 4.1 | $C_{22}H_{29}N_4O_5$ | 61.52 | 60.68 | 6.80 | 6.80 | 13.04 | 12.50 |

-continued

SPIN LABELED DERIVATIVES

| Precursor Compound Example No. | Emipirical Formula | %C Calcd. | %C Found | %H Calcd. | %H Found | %N Calcd. | %N Found |
|---|---|---|---|---|---|---|---|
| 4.3 | $C_{21}H_{33}N_4O_5$ | 59.83 | 58.78 | 7.89 | 7.76 | 13.29 | 12.70 |
| 4.4 | $C_{22}H_{35}N_4O_5$ | 60.66 | 60.25 | 8.10 | 7.94 | 12.86 | 12.31 |
| 4.5 | $C_{23}H_{31}N_4O_5$ | 62.28 | 60.75 | 7.04 | 6.82 | 12.63 | 12.12 |
| 4.6 | $C_{23}H_{32}N_3O_4$ | 66.64 | 66.21 | 7.78 | 7.85 | 10.13 | 9.81 |

EXAMPLE 4.8

3-[4'-(5''-[5''-(2'''-pentyl)]barbituryl)crotonamido]-2,2,5,5-tetramethylpyrrolidinyl-1-oxyl To 804 mg (3.0 mmoles) of 4-[5'-(5'[2''-pentyl]) barbituryl] crotonic acid and 423 μl isobutylchloroformate and the resulting mixture stirred at 0° under $N_2$ for one hour. 3-Amino-2,2,5,5-tetramethylpyrrolidinyl-1-oxyl (475 mg, 3.0 mmole) was added and the resulting yellow solution stirred under anhydrous conditions overnight, allowing the temperature to increase by letting the ice in the bath melt. In the morning, the reaction mixture was poured into 40 ml 5% aqueous sodium carbonate and washed with 2 × 50 ml of chloroform. The combined chloroform extracts were washed with 20 ml of saturated aqueous sodium bicarbonate and dried over sodium sulfate. Evaporation in vacuo gave a red oil which was column chromatograhed over 100 g silica gel eluting with 1 liter chloroform, 1 liter ether (abs.) and increasing gradient of acetone in ether. Obtained 1.0 g (79%) yellow solid of m.p. 142° C (decomp.), TLC: $R_f(0.4)$ 5% MeOH/CHCl$_3$.

EXAMPLE 4.9

3-[5'-(5''-Ethyl-5''-phenylbarbituryl-1'')pentanamido]-2,2,5,5-tetramethylpyrrolidinyl-1-oxyl A. To a suspended solution of sodium phenobarbital (1.0 g, 3.93 mmoles) in dry dimethylformamide (12 ml) was added ethyl 5-bromovalerate (920 mg, 4.43 mmoles) with stirring, and the mixture was heated at 40° for 10 minutes to give a clear solution. The mixture was stirred at room temperature for 15 hours, and then potassium iodide (200 mg) was added to complete the reaction which was followed by TLC (silica gel, 5% methanol-95% chloroform). Most of the solvent was evaporated under reduced pressure to leave an oil, which was dissolved in dichloromethane (50 ml) and washed with water. The solution was shaken once with 2.5% sodium carbonate solution (25 ml) to remove unchanged starting phenobarbituric acid. The dichloromethane layer, after being washed with water and dried over anhydrous sodium sulfate, was evaporated to leave an oil (1.4 g). This oil was separated into two fractions by preparative TLC, using 14 plates; each is made of 10 g of silica gel with an area of 20 cm by 20 cm. The oil was developed with 5% methanol--95% chloroform, and each fraction was collected by cutting and extracted with acetone. The products, after removal of the solvent, were dissolved in dichloromethane, washed with water, and dried over anhydrous sodium sulfate. One fraction ($R_f$ 0.7) gave a colorless oil (0.5 g, 36%) which proved to be analytically pure monoalkylated compound.

Anal. Calcd. for $C_{19}H_{24}O_5N_2$: C, 63.62; H, 6.71; N, 7.77 Found: C, 63.35; H, 6.75; N, 7.86.

B. Ethylester prepared above (120 mg, 0.333 mmole) was dissolved into a mixture of conc. HCl (2.5 ml), tetrahydrofuran (5 ml) and water (1 ml), and then kept at room temperature over night. After evaporation of tetrahydrofuran under reduced pressure, the residue was diluted with saturated sodium chloride solution (10 ml) and extracted with dichloromethane. The dichloromethane layer was extracted with saturated sodium bicarbonate solution, and then the combined alkaline layers, after being carefully acidified with conc. HCl in an ice-bath, were extracted with dichloromethane. The dichloromethane solution was washed with water, dried over anhydrous soidum sulfate, and evaporated to dryness to give an oily residue (100 mg, 93%), which crystallized on standing. Recrystallization from ether/n-hexane gave an analytical sample of product, m.p. 129°–130°.

Anal. Calcd. for $C_{17}H_2O\ O_5N_2$: C, 61.43; H, 6.07; N, 8.43 Found: C, 61.48; H, 6.08; N, 8.43.

C. A solution of the acid (66 mg, 0.199 mmole) in dry acetonitrile (1 ml) was added to a solution of dicyclohexylcarbodiimide (49 mg, 0.239 mmole) and 3-amino-2,2,5,5-tetramethylpyrrolidinyl-1-oxyl (37 mg, 0.235 mmole) in dry acetonitrile (2 ml) After the mixture was kept at room temperature with stirring overnight, the precipitate which separated was removed by filtration. After the solvent was evaporated, the filtrate gave an oil, which was dissolved in dichloromethane, washed with 2N-HCl solution, and then water. The dichloromethane solution was dried and evaporated to leave an oil, which was purified by preparative TLC (silica gel, 5% methanol-95% chloroform). The yellow band ($R_f$ 0.4), after being worked up as usual, gave the product as an oil, 70 mg; yield, 75%. ESR, 3 lines in ratio of 1:1:1, $a_N$ = 16.8 G ($H_2O$).

Anal. Calcd. for $C_{25}H_{35}O_5N$: C, 61.67; H, 7.48; N, 11.88 Found: C, 63.21; H, 7.53; N, 11.64.

EXAMPLE 4.10

3-[4'-(5''-phenyl-5''-ethylbarbituryl-1'')-crotonamido]-2,2,5,5-tetramethylpyrrolidinyl-1-oxyl A. To a suspended solution of sodium phenobarbital (1.5 g, 5.80 moles) in dimethylformamide in an ice-water bath was added ethyl 4-bromocrotonate (1.28 g, 6.5 mmoles). After the mixture was stirred for 30 minutes sodium iodide (400 mg) was added. After being stirred at room temperature for an additional 30 minutes, the mixture was diluted with water and extracted with ether. The ether solution was washed with water, dried and evaporated to leave an oil. This oil was dissolved in dichloromethane (50 ml), washed with 2.5% sodium carbonate aqueous solution (25 ml), to remove unchanged starting phenobarbitone, and washed with water. The dichloromethane solution, after drying and evaporation of the solvent gave an oil (1.3 g), which was separated into two fractions by preparative TLC (silica gel, 5% methanol - 95% chloroform). One fraction ($R_f$ 0.5) gave an oil (0.5 g, 25% yield) of monoalkylated compound.

Anal. Calcd. for $C_{18}H_{20}O_5N_2$: C, 62.78; H, 5.85; N, 8.14 Found: C, 62.76; H, 5.92; N, 8.21.

B. The above ester (250 mg, 0.727 mmole) was dissolved in a mixture of tetrahydrofuran (5 ml) conc. HCl (2.5 ml) and water (1 ml), and heated at 50° overnight. After the cooled solution was worked up in the same manner as in Example 4.9, the residual oil gave crystals (220 mg, 94%), m.p. 159°–60° of the $\alpha,\beta$-unsaturated acid.

Anal. Calcd. for $C_{16}H_{16}O_5N_2$: C, 60.75; H, 5.10; N, 8.86 Found: C, 60.89; H, 5.21; N, 8.87

C. The $\alpha,\beta$-unsaturated acid prepared above (60 mg, 0.190 mmole) in acetonitrile (1 ml) was added to a mixture of dicyclohexylcarbodiimide (47 mg, 0.229 mmole) and 3-amino-2,2,5,5-tetramethylpyrrolidinyl-1-oxyl (40 mg, 0.254 mmole) in acetonitrile (2 ml) and stirred at room temperature overnight. After removal of the solvent and precipitates, the residual oil was dissolved in dichloromethane solution which was dried and evaporated to give an oil, which was purified by preparative TLC (silica gel, 5% methanol - 95% chloroform). After being worked up as usual, a yellow oil (25 mg, 34.5%) as the product with $R_f$ 0.4 was obtained. ESR, 3 lines in a ratio of 1:1:1, $a_N$ = 16.8 G. Anal. Calcd. for $C_{24}H_{31}O_5N_4$: C, 63.28; H, 6.86; N, 12.30 Found: C, 63.05; H, 7.12; N, 10.52.

EXAMPLE 4.11

5-(3'-Carboxy-2'-dimethylaminopropyl)-5-phenylbarbituric acid

A. To a solution of the $\alpha,\beta$-unsaturated ester prepared in Example 4.10 (100 mg, 0.291 mmole) in absolute ethanol (0.5 ml) was added dimethylamine (about 1 ml). After the mixture was kept at room temperature for 40 hours, all the solvents were removed under reduced pressure to leave an oil (105 mg). This oil was purified by preparative TLC (silica gel, a 2:1 mixture of ether and petroleum ether). The extraction of a band with $R_f$ 0.7 with ether afforded a colorless oil (100 mg) in 89% yield.

Anal. Calcd. for $C_{20}H_{27}O_5N_3$: C, 61.68; H, 6.99; N, 10.79 Found: C, 61.82; H, 6.74; N, 10.52.

B. The above product (250 mg, 0.643 mmole) was dissolved in 0.5N sodium hydroxide solution (3 ml), and kept at room temperature for 2 hours until the starting material disappeared. The starting material shows $R_f$ 0.5 on silica plate using a 1:1 mixture of ether and petroleum ether as a solvent. The solution was washed with ether and then acidified wth conc. hydrochloric acid. The acidic solution was washed with ether and evaporated under reduced pressure to dryness to leave a mixture of ether and petroleum ether as a solvent. The solution was washed with ether and evaporated under reduced pressure to dryness to leave a mixture of sodium chloride and an oily product. After the mixture was treated with dry acetone to remove sodium chloride, evaporation of acetone gave a pure colorless oil (210 mg, 82%) of the hydrochloride product.

Anal. Calcd. for $C_{18}H_{24}O_5N_3Cl$: C, 54.34; H, 6.08; N, 10.56; Cl, 8.91 Found: C, 52.08; H, 6.46; N, 9.95; Cl, 8.40.

The above product can be used according to prior procedures for combining with 3-amino-2,2,5,5-tetramethylpyrrolidinyl-1-oxyl to provide the spin labeled product 3-[4'-(5''-ethylbarbituryl-5'')-3'-dimethylaminobutyramido]-2,2,5,5-tetramethylpyrrolidinyl-1-oxyl.

EXAMPLE 4.12

Conjugate of N-carboxymethyl phenobarbitone and bovine serum albumin (BSA)

N-Carboxymethyl phenobarbitone and bovine serum albumin (3 ml) prepared as described in Example 4.1 was cooled to −15°. To the magnetically stirred solution was added triethylamine (0.14 ml, 1.0 mmole) and isobutylchloroformate (0.13 ml, 1 mmole). The reaction mixture was stirred at −15° for 10 minutes and then at 0° for 30 minutes. The mixed anhydride prepared above was added slowly to an ice-cooled solution of bovine serum albumin (BSA) (400 mg) in water (56 ml) containing sodium bicarbonate (2.6 g). The reaction mixture was stirred at 0° for 6 hours and was then dialyzed against distilled water with four changes of 4 l. of water each. The dialyzed solution was then centrifuged and decanted to obtain 118 ml of a clear solution. Lyophylization of 10 ml of this solution yielded 0.0362 g of protein conjugate equivalent to a total yield of 0.427 g of conjugate. The bulk of the solution was dialyzed again with a phosphate buffer at pH 8 with 4 changes of the buffer solution in intervals of 3, 17, 25 and 49 hour intervals. Finally, dialysis against water for 48 hours, followed by freeze-drying, yielded 0.325 g of protein conjugate. A U.V. calibration curve with BSA and N-carboxymethyl phenobarbitone in $H_3BO_3$/NaOH/KCl buffer at pH 10 provided the means for determining the number of hapten molecules on the BSA. This was found to be 15 N-carboxymethyl phenobarbitone molecules per molecule of BSA.

EXAMPLE 4.13

Conjugation of 5-($\gamma$-crotonic acid)-5-(2'-pentyl)barbituric acid with bovine serum albumin (BSA)

To a solution of 5-($\gamma$-crotonic acid)-5-(2'-pentyl)-barbituric acid (0.282 g, 1 mmole) in DMF (3 ml) cooled to −15° (ice-salt bath) there was added triethylamine (0.28 ml, 2 mmoles) and isobutylchloroformate (0.13 ml, 1 mmole). Stirring was continued at −15° for 15 minutes and then at 0° for 30 minutes. The reaction mixture was then added dropwise, with a syringe, to a cooled solution of BSA (400 mg) in water (56 ml) containing $NaHCO_3$ (2.6 g). The reaction mixture was stirred at 0° (cold room) for 5 days when initial turbidity had nearly all disappeared. The solution was then dialyzed against 4 l. of phosphate buffer (pH 8) followed by distilled water (8 l.). After lyophilization the yield of conjugate was 0.52 g. U.V. measurement of an aliquot of the dialyzed solution, before lyophilization and comparison with a calibration curve, showed a degree of conjugation of about 50–60 hapten moles per mole of BSA.

EXAMPLE 4.14

Conjugation of N-carboxymethyl glutethimide with bovine serum albumin (BSA)

Triethylamine (2.8ml, 20 mmoles) and isobutylchloroformate (1.3 ml, 10 mmole) were added to a cooled solution (ice bath) of N-carboxymethyl glutethimide (2.75 g, 10 mmole) in DMF (10 ml). A mixture of 10 ml DMF and 10 ml dioxane were added to the reaction but there was no effect on the turbidity of the reaction mixture. Stirring at 0° was continued for 1 hour after which the mixed anhydride solution was added slowly to a solution of BSA (4.0 g, 6.2 × $10^{-5}$ moles) in a mixture of methanol (250 ml) and sodium bicarbonate (26 g) dissolved in water (550 ml). After stirring overnight in the cold room the reaction mixture was centrifuged and then dialyzed with 80 l. of water. Lyophilization of the dialyzed solution yielded 4.2 g of conjugate.

EXAMPLE 5.1

3-Carboxy-2,2,5,5-tetramethyl-1-pyrrolidinyl-1-oxyl (4'-carbethoxy-4'-phenyl)piperidide 3-Carboxy-2,2,5,5-tetramethyl-pyrrolidinyl-1-oxyl (52.2 mg.) was dissolved in 2 ml. of dry benzene along with 30 μl of pyridine. Thionyl chloride (27 μl) was added to the ice-cold solution. After stirring for 1 hour the salts were removed by filtration with exclusion of moisture and washed with dry benzene. The filtrate was evaporated and the residue dried at 0.1 mm. Hg. for one hour (room temperature). 4-Carbethoxy-4-phenyl-piperidine (77.4 mg.) was dissolved in 1 × 3 ml. pyridine and added to the solution of the above acid chloride at 0°. After stirring at 0° for 1 hour the reaction was diluted with 20 ml. ethyl acetate and extracted with 20 ml. 0.1 N. hydrochloric acid. The residue from the organic phase was separated on preparative TLC (methanol/chloroform 1:9). There was a colorless band with a $R_f$ of 0.8 which was the title compound. After elution of the silica gel with methanol, a pale yellow compound is obtained which melted after two recrystallizations from cyclohexane at 114°–116°.

EXAMPLE 5.2

4'-(2-(4'-Carbethoxy-4'-phenyl-1'-piperidino)acetamido)-2,2,6,6-tetramethyl-1-piperidinooxyl 4-Carbethoxy-4-phenyl-piperidine (83.7 mg.) was dissolved in 2 ml. of dry ethanol and added to a solution of 104.3 mg. 4-(2'-bromoacetamido)-2,2,6,6-tetramethyl-1-piperidinooxyl in 2 ml. ethanol containing 49.8 mg. potassium carbonate. After heating the reaction to reflux for two hours the solution was diluted with 20 ml. water. The pH was adjusted to 12 and the solution extracted with ether. All the yellow color went into the organic phase. On evaporation of the ether a residue remained which was recrystallized from benzene/hexane. m.p. 137°–138° (48 mg.).

EXAMPLE 5.3

3-[N-(4'-(4'-Phenyl-1'-methylpiperidinyl))carbamoyl]-2,2,5,5-tetramethylpyrrolidinyl-1-oxyl A. Meperidine hydrochloride (142 mg.) was refluxed under nitrogen in 2.5 ml. potassium hydroxide (4M) and 5 ml. methanol for two hours. The methanol was removed on the rotary evaporator. The aqueous solution was made alkaline to pH 8.1. A precipitate formed which was collected and dried. 79 mg. (76%). m.p. 298°–300°.

B. 4-Carboxy-1-methyl-4-phenyl-piperidine (110 mg.) (prepared above) was refluxed in 3 ml. of freshly-distilled THF and 178 mg. (110 μl) thionyl chloride for 30 minutes. The insoluble acid resulted in a voluminous precipitate. After removal of the solvent in vacuo the residue was dissolved in 3 ml. dry pyridine and added to 231 mg. 3-amino-2,2,5,5-tetramethylpyrrolidinyl-1-oxyl. After one hour at 0° the reaction was diluted with water and the pH adjusted to 11. Two extractions with ether and two extractions with ethyl acetate removed the radical from the aqueous phase. The residue from the extraction was separated by preparative TLC. The yellow band with the lowest $R_f$ value contained an amide (IR). It was removed from the silica gel with methanol and recrystallized from benzene/hexane. m.p. 84°–86°.

EXAMPLE 5.4

3-(2'-(4''-Carbethoxy-4''-phenylpiperidinyl-1'')acetamido)-2,2,5,5-tetramethyl-1-pyrrolidinyl-1-oxyl 4-Carbethoxy-4-phenylpiperidine (69.3 mg.) was dissolved in 2 ml. ethanol and 82.3 mg. of 3-(2'-bromoacetamido)-2,2,5,5-tetramethylpyrrolidinyloxy-1 in 2 ml. ethanol are added together with 40.8 mg. potassium carbonate. The solution was refluxed for 2 hours and diluted with 20 ml. water. On extraction with ether all of the yellow color went readily into the organic phase. The residue from the organic phase was recrystallized twice from benzene/hexane and yields 118 mg. of yellow crystals. m.p. 98°–99°.

EXAMPLE 5.5

Conjugation of 4-carboxy-1-methyl-4-phenylpiperidine with bovine serum albumin (BSA)

4-Carboxy-1-methyl-4-phenylpiperidine (54.8 mg.), prepared in Example 5.3, was suspended in 3 ml. DMF. The solution was cooled at −15° and 32.8 μl isobutyl-chloroformate was added. The mixture was maintained at −15° with stirring. After 30 minutes the solution was added to a solution of 161 mg BSA in 18 ml. water which had dissolved in it 1.1 g. of sodium bicarbonate. The mixture was kept in the cold room overnight. It was dialyzed against distilled water (80:1) with 3 changes during 36 hours. On lyophylization 159 mg. residue remained. It contained 32 haptens per molecule of BSA as shown by UV analysis.

EXAMPLE 5.6

Conjugation of 4-carbethoxy-1-carboxymethyl-4-phenylpiperidine to bovine serum albumin (BSA)

A. 4-Cyano-4-phenylpiperidine hydrochloride (2.23 g.) was dissolved in 15 ml. water to which was added 4 ml. of 50% aqueous potassium hydroxide. The oil was extracted with 3 × 15 ml. ether and the organic layers were dried over an anhydrous magnesium sulfate. Filtration and evaporation of the solution gave a residue which was placed in a glass ampoule along with 3 ml. of methanol and 1.23 ml. of 50% aqueous potassium hydroxide. The sealed ampoule was heated to 165°–170° for 3.5 hours and diluted with 50 ml. water. After extraction with chloroform the aqueous phase was neutralized with DOWEX 50-X8 ($H^+$ form) to pH 6. Filtration and evaporation yielded a residue (0.82 g.) which melted above 300°. Recrystallization from water and drying over phosphorus pentoxide gave a compound with m.p. 285°–286°.

B. 4-Carboxy-4-phenylpiperidine (1.8 g.) was refluxed in 50 ml. of 5% ethanolic hydrochloride for four hours. The residue on evaporation of the solvent was dissolved in acetone and the insoluble part filtered off.

From the acetone solution a viscous oil remained on evaporation, which crystallized on standing. m.p. 107°–110° (1.068 g.). It was used without further purification. or B.1. A solution of 4-cyano-4-piperidine hydrochloride in 6 ml. 66% sulfuric acid was heated to 145° and stirred for 45 minutes. On cooling to 125° the solution became slightly more viscous. The addition of ethanol (stem of the addition funnel below the surface of the reaction mixture) lowers the temperature to 105°. It was kept there for 4 hours. During the first hour 20 ml. ethanol were added, in the next hours 6 ml. each. The ethanol vapors were removed by a continuous distillation. At the end of the addition the temperature was raised to 125° until no condensation is formed any more. The hot solution was poured into 6 ml. water/40 gm. ice containing 8 g. sodium hydroxide. After extraction with 3 × 70 ml. ether, drying over anhydrous magnesium sulfate and removal of the solvent an oil remained which was distilled at 112°–115°/0.2 mm. Hg. 4.01 gm. (54%).

C. 4-Carbethoxy-4-phenylpiperidine (4.01 g.) was dissolved in 13 ml. absolute alcohol and refluxed together with 2.01 g. sodium chloroacetate. After 7 hours no starting material was present as evidenced by TLC. The precipitated sodium chloride was removed by filtration and washed with 3 ml. ethanol. On cooling of the filtrate white crystals appeared. Filtration and drying gave 2.9 g. (58%) of the title compound. m.p. 148°–150°C. Evaporation of the mother liquor gave a glass which did not crystallize from acetone/hexane.

D. A solution of 1.76 g. 4 -carbethoxy-1-carboxymethyl-4-phenylpiperidine in 65 ml. absolute DMF were cooled to −10° and to this 680 μl isobutylchloroformate were added. The reaction was kept at −10° for 45 minutes while stirring. The mixed anhydride is added dropwise to 3.2 g. BSA dissolved in 450 ml. water containing 21 g. sodium bicarbonate. A slight turbidity occurred after ⅓ of the DMF solution was added. It was partially removed by addition of another 250 ml. water. After stirring a 4° overnight and dialyzing against distilled water for 2 days, the solution was centrifuged to remove the precipitate and lyophylized. UV analysis showed 46 haptens per molecule BSA.

EXAMPLE 6.1

N-2′,2′,5′,5′-tetramethylpyrrolidin-3′-yl-1′-oxyl 6-keto-7,7-diphenyl-9-(dimethylamino)-decanamide A. A solution of tetramethylene dibromide (32.4 g., 150 mmoles) in dry ether (150 ml.) was added to magnesium (10.9 g., 450 mmoles) in ether (80 ml.) at such a rate that the ether refluxed. The reaction was carried out under argon. After the addition was completed, the reaction mixture was boiled for one hour. A solution of 2,2-diphenyl-4-dimethylaminovaleronitrile (I), (prepared according to J. W. CUSIC, J. Am. Chem. Soc., 71 3546) (8.4 g., 30 mmoles) in dry xylene (100 ml.) was added during 30 min. at room temperature, and the mixture was stirred at 55°C. for one hour. The reaction mixture was cooled in an ice-water bath and $CO_2$ was passed through with fast stirring for four hours. Water (200 ml.) and concentrated HCl (100 ml.) were added, the magnesium filtered off, and the filtrate was refluxed for two hours. The cooled, clear solution was washed with ether (3 × 150 ml.) and extracted with dichloromethane (3 × 150 ml.). This extract was evaporated to dryness, and the residue dissolved in 0.5 liter of 0.5 N sodium hydroxide.

This solution was washed with ether (3 × 100 ml.), made acidic with conc. HCl (150 ml.), saturated with sodium chloride and extracted with dichloromethane (3 × 200 ml.). Evaporation of the solvent left an oil (7.55 g., 60%), 6-keto-7,7-diphenyl-9-(dimethylamino) decanoic acid hydrochloride, which moves as a single spot on TLC ($HCCl_3$:MeOH 8.2 and 7:3).

U.V. Spectrum

| 0.02% $CF_3COOH$ | |
|---|---|
| λmax | 293 (ϵ=540); 264 (ϵ=500); 259 (ϵ=535); | b. The above product (1.170 g., 2.8 mmoles) and $Et_3N$ (423 μl.) were dissolved in dry DMF (5 ml.), cooled to 0°C. and treated with isobutyl chloroformate (393 μl.), with stirring under $N_2$ for 1 hour. 3 -Amino-2,2,5,5-tetramethylpyrrolidinyl-1-oxyl (450 mg.) was added and the reaction mixture was stirred at room temperature over night, poured into 5% $Na_2CO_3$ (40 ml.) and extracted with ether (3 × 20 ml.). The ether solution was washed with water (2 × 10 ml.) and with 19% NaCl solution (2 × 10 ml.). Evaporation of the ether left a red oil which was purified by chromatography on silica gel ($HCCl_3$ → $Et_2O$ → 50:50 $Et_2O$:acetone) to give an oil which solidified on standing. (900 mg., 62%).

Anal. Calc. for $C_{32}H_{46}N_3O_3$ : C 73.80; H 8.90; N 8.06
Found: C 73.27; H 8.86; N 7.98.

EXAMPLE 6.2

Methadone-BSA conjugate

The decanoic acid prepared in Example 6.1 (0.63 g., 1.5 mmoles) and $Et_3N$(0.63 ml., 4.5 mmoles) were dissolved in dry DMF (5 ml.) at −8°C. Isobutylchloroformate (0.19 ml.) was added and the mixture was kept at 8° C. for one-half hour and at 0°C. for another one-half hour. The solution of the mixed anhydride thus obtained was added dropwise to a solution of BSA (1.4 g., 1.07 mequiv.) in a mixture of water (200 ml.), methanol (110 ml.), and sodium bicarbonate (9.2 g.), at 0°C. The mixture was stirred a 0°C. for 18 hours, dialyzed (18 hours, constant flow of dist. water) and lyophylyzed. Yield of the conjugate: 1.2 g. (some mechanical losses). The degree of conjugation was found from the UV spectrum of the conjugate (using a calibration curve) to be about 50% (35 methadone molecules per BSA).

EXAMPLE 7.1

N-(p-Cocainyl) and N-(p-benzoylecgonine) (1-oxyl 2,2,5,5-tetramethylpyrrolidinyl-3)formamide A. Ecgonine hydrochloride (5.5 g, 24.8 mmoles, mw 221.7) was dissolved in 35 ml of anhydrous methanol and saturated with dry HCl keeping the receiver cool by immersion in an ice bath. Upon saturation the receiver was heated to 40° for 1/2 hour and then evaporated to dryness in vacuo. The white residue was stored at 0.05 mm Hg over potassium hydroxide for 16 hours and then dissolved in the minimum amount of hot methanol to which 200 ml of boiling acetone was quickly added. After cooling in ice and filtering, there was obtained 4.2 g of white crystals, m.p. 214°–215° (lit. 214°–215°). Evaporation of the mother liquor and repetition of the recrystallization yielded 0.8 g m.p. 212°–214°. Total yield was 86.3% of theory.

B. To 20 ml of cold saturated potassium carbonate solution in a 125 ml separatory funnel was added a solution of 5.0 g (213 mmoles) ecgonine methyl ester hydrochloride in 5 ml water. The aqueous mixture was extracted with 4 × 50 ml of chloroform. The combined chloroform extracts were dried over anhydrous sodium carbonate and evaporated in vacuo. Pumping at 0.05 mm Hg for 15 minutes yielded 4.0 g (93%) of TLC pure (20:1, CHCl$_3$:MeOH) ecgonine methyl ester.

The 4.0 g (20.1 mmoles) ecgonine methyl ester (m.w. 198.8 was dissolved in 50 ml dry benzene and then 30 ml benzene was distilled off. To the cooled distillation pot was added 3.65 ml triethylamine and dropwise with cooling (ice bath) and stirring a solution of 3.72 g freshly recrystallized p-nitrobenzoyl chloride in 5 ml of dry benzene was added.

The resulting sludge was stirred at 40° for 1 hour under nitrogen. After cooling to room temperature the reaction mixture was taken up in 100 ml of chloroform and washed with 3 × 20 ml 5% aqueous sodium carbonate solution. The chloroform solution was dried over sodium carbonate, evaporated in vacuo and pumped (0.05 mm Hg) on overnight to yield 5.7 g (85.3%) of a yellow oil [one spot on TLC (95/5, CHCl$_3$/MeOH)] and having the same R$_f$ as a known sample, but having a slight odor of triethylamine. No further attempt at purification was made and the product was used directly in next step.

C. To a solution of 6.5 g p-nitrococaine in 250 ml absolute methanol was added 600 mg 10% Pd/C under a N$_2$ blanket. The resulting mixture was hydrogenated at atmospheric pressure with rapid stirring and slight heating from the magnetic stirrer. After 1/2 hour H$_2$ uptake ceased [1.530 liters calculated is 1.440 liters without correction for atmospheric pressure]. The catalyst was removed by suction filtration over a Celite pad in a fritted glass funnel (Medium grade). The resulting clear solution was evaporated in vacuo to approximately 75 ml and heated to dissolve crystals and allowed to cool to room temperature, then cooled in ice and filtered to give 4.0 g of white crystals, m.p. 188°–189° (lit. 188°–189°). The mother liquor was concentrated to 3 ml, cooled in ice and filtered. After washing the crystals with 6 ml of cold methanol, there was obtained 1.2 g powdery crystals, m.p. 185°–188°. Total yield 88%.

D. To a mixture of 374 mg (2.0 mmoles) 3-carboxy-1-oxyl-2,2,5,5-tetramethylpyrrolidine and 292 µl (2.05 mmoles) triethylamine in 5 ml anhydrous ethyl ether was added 145 µl (2.0 mmoles) thionyl chloride and the resulting mixture stirred at room temperature for 1/2 hour under nitrogen. The ether was removed by heating to 40° for several minutes and a solution of 636 mg (2.0 mmoles) para-aminococaine and 292 µl (2.05 mmoles) triethylamine in 20 ml of anhydrous ethyl ether was added and the mixture refluxed under nitrogen for 1/2 hour. The mixture was cooled in ice and filtered. The filtrate was washed with 10 ml of 5% aqueous sodium carbonate solution and dried over anhydrous sodium carbonate. The dried ethereal solution was then poured into 200 ml of petroleum ether and the resulting pale yellow precipitate filtered and washed with 50 ml of petroleum ether. The precipitate was taken up in 5 ml of benzene and the precipitation procedure was repeated. The resulting pale yellow solid was dried at 0.05 mm Hg over phosphorus pentoxide at room temperature overnight to yield 100 mg m.p. 208°–210°. Anal. Calcd. for C$_{26}$H$_{36}$N$_3$O$_6$: C, 64.18; H, 7.46; N, 8.64; Found: C, 64.18; H, 7.57; N, 8.44.

E. A solution of 70 mg N-(p-cocainyl (1-oxyl-2,2,5,5-tetramethylpyrrolidinyl-3)formamide in 8 ml water and 8 ml dioxane was refluxed for 48 hours under nitrogen. After this time TLC (silica; 1:1 chloroform, methanol) indicated very little starting material to be present. The reaction was evaporated to dryness in vacuo while maintaining the temperature less than 40°. The residue was purified by preparative TLC and was removed from the silica by washing with methanol. The evaporated residue was freed of silica by trituration with acetone and filtering. The pure benzoylecgonine was isolated as a viscous oil. 70% yield (48 mg) Anal. Calcd. for C$_{25}$H$_{34}$N$_3$O$_6$·H$_2$O: C, 61.21; H, 7.39; N, 8.56 Found: C, 61.28; H, 7.38; N, 8.34.

EXAMPLE 7.2

3-(N'-norcocainyl)acetamido)-2,2,5,5-pyrrolidinyl)-1-oxyl

A. A solution of 1.33 g (4.6 mmole) of benzoyl ecgonine in 200 ml water was adjusted to pH 9 with a few drops of sodium hydroxide. Potassium permanganate (61 ml of 3% aqueous solution) was added dropwise with good stirring at 25°. After 18 hours at room temperature, the solution was cooled to 5° and 50 ml ethanol was added to destroy excess oxidant. After stirring for 1 hour the reaction mixture was filtered through Celite and the pH of the filtrate adjusted to 4 with 1N hydrochloric acid. The aqueous solution was evaporated to dryness in vacuo. Care was taken to maintain the temperature at less than 35° to prevent debenzoylation. The residue was triturated twice with hot ethanol and filtered. The ethanol was evaporated and the residue recrystallized from ethanol to give 0.875 g of colorless crystals; m.p. 227°–230°. Anal. Calcd. for C$_{15}$H$_{17}$NO$_4$·HCl·C$_2$H$_5$OH: C, 57.05; H, 6.76; N, 3.91; Cl, 9.91 Found: C, 56.78; H, 6.52; N, 3.85; Cl, 9.89.

B. A solution of 1.50 g benzoyl nor-ecgonine hydrochloride in 50 ml methanol was saturated with dry hydrogen chloride. The reaction mixture was then refluxed for one hour before being evaporated to a light yellow oil. The residue was dissolved in chloroform, washed once with dilute base and then evaporated to give 1.106 g of yellow oil. The product was chromatographed on silica gel using chloroform as the initial eluent. After a few minor impurities were eluted norcocaine was removed with 10% methanol in chloroform and was recovered as a colorless oil.

C. A solution of 1.43 g (5.2 mmole) norcocaine and 0.840 g (6.25 mmole) sodium bromoacetate was refluxed under nitrogen for 3 hours in 10 ml of anhydrous methanol. The reaction was judged to be complete at this point by TLC with 10% methanol-chloroform. The solution was evaporated to dryness before 10 ml chloroform and 15 ml water were added. The pH of the aqueous phase was adjusted to 3–4 with 1N hydrochloric acid. The chloroform phase was washed once with water and evaporated to give 0.470 g norcocaine. The aqueous phase was washed once with chloroform and evaporated in vacuo at 35°. The N-carboxymethyl norcocaine crystallizes as the solution is concentrated. A total of 1.75 g was recovered in this manner and was recrystallized from water: m.p. 173°–178°. Anal. Calcd. for C$_{18}$H$_{21}$NO$_5$·HCl: C, 56.32, H, 5.77; N, 3.65; Cl, 9.25 Found: C, 55.92; H, 5.80; N, 3.49; Cl, 9.06.

D. To a solution of 0.041 g (0.2 mmole) dicyclohexylcarbodiimide and 0.028 g (0.2 mmole) of 3-amino-2,2,5,5-tetramethylpyrrolidinyl-1-oxyl in 2 ml ethyl acetate and 2 ml dichloromethane was added 0.067 g (0.2 mmole) N-carboxymethyl norcocaine. The reaction was stirred a 25° for 24 hours, the urea was filtered, and the filtrate was evaporated to dryness. The residue was purified by preparative TLC (10% methanolchloroform) on silica gel. The product, isolated as a crystalline light yellow solid has a 3 line ESR spectrum $a_N(H_2O) = 16.5G$.

EXAMPLE 7.3

N-[p-(1-oxyl-2,2,5,5-tetraemthylpyrrolidinyl-3-formamido]benzyl norecgonine methyl ester A. nor-Benzoylecgonine hydrochloride (1.35 g, 9.5 mmoles) in 45 ml 2N hydrochloric acid was refluxed for three hours. The cooled reaction mixture was washed with 3 × 30 ml ether, the aqueous layer evaporated in vacuo and dried a 0.05 mm Hg over potassium hydroxide pellets for 16 hours. The white residue was dissolved in anhydrous methanol and saturated with hydrogen chloride keeping the receiver cooled in ice. The mixture was heated to 50° for 1/2 hour and stripped in vacuo, pumped on (0.1 mm Hg) for one hour and then 30 ml ice cold saturated aqueous potassium carbonate solution added. The suspension was quickly extracted with 3 × 50 ml of chloroform, combined extracts dried over sodium carbonate and evaporated in vacuo. The oil was pumped on (0.05 mm Hg) for 20 minutes to give 1.57 g (93%) straw colored oil. TLC $R_f$ (0.15) $CHCl_3MeOH$, 9/1, silica gel.

B. To a solution of 7.0 g (38.0 mmoles) nor-ecgonine methyl ester prepared above in 50 ml ether was added a solution of 8.22 g (38 mmoles) p-nitrobenzylbromide in 150 ml ether and 5.3 ml (38 mmoles) triethylamine. The resulting mixture was stoppered and stirred at room temperature for 2 days. Hydrochloric acid (1N, 150 ml) was added and the mixture shaken. After separation, the aqueous layer was washed with 100 ml ether and made alkaline with excess aqueous sodium carbonate. The resulting oil was quickly taken up in 2 × 100 ml chloroform, dried over sodium carbonate, evaporated in vacuo and pumped on for 1 hour to yield 9.0 g (73%) pale yellow oil which began to crystallize after 1/2 hour. The crystalline residue was recrystallized from 200 ml methylcyclohexane to give 7.2 g yellow crystals m.p. 78°–88°; repeated crystallization failed to raise the melting point. The mother liquor was stripped in vacuo, the residue taken up in 500 ml dry ether, hydrogen chloride bubbled in until precipitation ceased, filtered and recrytallized from 2% methanol in chloroform three times. The white crystals were dried at 100° (0.05 mm Hg) for 10 hours to give m.p. 210°–212° (decomp.) Anal. Calcd. for $C_{16}H_{21}N_2O_5Cl$: C, 53.85; H, 5.93; N, 7.85; Cl, 9.95 Found: C, 51.69; H, 5.76; N, 7.50; Cl, 10.01. TLC $R_f$ (0.45) ethyl ether, silica gel.

C. To 3.50 g (10.9 mmoles) N-(p-nitrobenzyl-) norecgonine methyl ester in 600 ml anhydrous 2% methanolic hydrogen chloride was added 350 mg 10% palladium on charcoal under a nitrogen blanket. The mixture was hydrogenated at atmospheric pressure and after 20 minutes, $H_2$ uptake ceased. Total uptake was 795 ml; calcd. was 805 ml, not taking atmospheric pressure into account. The catalyst was removed using a Celite pad on a medium grade glass frit and washed with 100 ml methanol. The resulting clear solution was evaporated in vacuo to approximately 50 ml and cooled in ice. The ensuing white crystalline precipitate was filtered and washed with 25 ml ice cold methanol. After drying overnight at 0.05 mm Hg over potassium hydroxide pellets, obtained 3.50 g (89%) white crystals m.p. 220° (decomp.). Repeated crystallization failed to change the melting point.

Anal. Calcd. for $C_{16}H_{24}N_2O_3$: C, 52.90; N, 7.71; H, 6.66; Cl, 19.52 Found: C, 52.62; H, 6.69; N, 7.73; Cl, 19.22.

188 mg of the dihydrochloride was treated with 10 ml ice cold 5% aqueous potassium carbonate, quickly extracted with 3 × 40 ml chloroform, dried over sodium carbonate, evaporated in vacuo and pumped on to yield 150 mg light brown oil. TLC $R_f$ (0.2) ethyl ether on silica gel.

D. To a solution of 187 mg (.1.0 mmole) 3-carboxy-2,2,5,5-tetramethylpyrrolidine-1-oxyl in 5 ml dry DMF at 0° was added 139 μl (1.0 mmole) triethylamine and 125 μl (1.0 mmole) isobutylchloroformate and the mixture stirred under $N_2$ for 45 minutes at 0°. To this mixed anhydride solution was added a suspension of 363 mg (1.0 mmole) N-(p-aminobenzyl norecgonine methyl ester dihydrochloride and 417 μl (3.0 mmoles) triethylamine in 10 ml dry DMF at 0°. The resulting mixture was stirred at 0° for 2 hours under $N_2$, then at room temperature overnight. The DMF was evaporated in vacuo, residue taken up in 10 ml water, made alkaline with aqueous sodium carbonate and quickly extracted with 3 × 20 ml ether. The combined ethereal extracts were dried over sodium carbonate stripped in vacuo and pumped on (0.05 mm Hg) for 2 hours. The residue was dissolved in 5 ml benzene and 15 ml ether added. The resulting precipitate was filtered and the supernatant stripped in vacuo to yield 100 mg (22%) yellow crystals. TLC $R_f$ 0.3, 5% MeOH/EtOH, on silica gel.

EXAMPLE 7.4

5-(N-Norcocainyl)valeric acid

A. Norcocaine (100 mg, 0.346 mmole), benzyl 5-bromovalerate (164 mg, 0.623 mmole), diisopropylethyl amine (130 mg, b.p. 126°/760 mm Hg, 1.04 mmoles) and potassium iodide (200 mg) were refluxed in dry benzene (5 ml) with continuous stirring for 12 hours until the starting norcocaine disappeared, as shown by TLC (silica gel, $R_f$ 0.45, 5% methanol -- 95% chloroform). The cooled mixture was diluted with ether and the precipitate separated and was removed by suction filtration. The filtrate was washed with water, dried, condensed and purified by preparative TLC (silica gel) using chloroform containing 5% -- methanol as a solvent. A band with $R_f$ value of 0.8 was collected by cutting and extracted with acetone. Removal of the acetone left an oil, which was dissolved in dichloromethane, washed with water, and dried over anhydrous sodium sulfate. The dichloromethane solution was evaporated to dryness and gave a colorless oil (140 mg) of the product in 92% yield. IR (neat) 1730, 1715, 1600 and 1584 $cm^{-1}$.

Anal. Calcd. for $C_{28}H_{33}NO_6$: C, 70.12; H, 6.94; N, 2.92 Found: C, 70.11; H, 7.08; N, 2.91.

B. The benzyl ester prepared above (70 mg, 0.149 mmole) in ethyl acetate (4 ml) was hydrogenolyzed over 10% palladium on charcoal (35 mg) at 20° for 30 minutes, at which time 4.0 ml of hydrogen (0.154 mmole) had been absorbed. After removal of the catalyst, the solvent was evaporated to leave a colorless oil, which was treated with a small amount of a 1:5 solution of ether and petroleum ether. The insoluble heavier oil was evaporated to dryess to afford a colorless oil (50 mg, 81%) of the product, which on purification by preparative TLC (silica gel, 10% methanol -- 90% chloroform) gave an analytically pure oil.

Anal. Calcd. for $C_{21}H_{27}NO_6$: C, 64.76; H, 6.99; N, 3.60 Found: C, 64.13; H, 7.56; N, 3.60.

EXAMPLE 7.5 -- 4-(N-Norcocainyl)crotonic acid

A. Norcocaine (100 mg, 0.358 mmole), benzyl 4-bromocrotonate and diisopropylethylamine (130 mg, 1.07 mmoles) in dry benzene (5 ml) were refluxed with continuous stirring for 2 hours. The mixture was cooled, and the precipitate which separated was removed. The filtrate was diluted with ether (10 ml) and then washed with water and dried over anhydrous sodium sulfate. After removal of solvents, the oil obtained was purified by preparative TLC (silica gel, 1:1 ether/petroleum ether), to give analytically pure benzyl 4-(N-norcocainyl)crotonate (130 mg, 81%), showing one spot ($R_f$ 0.45) on TLC. Anal. Calcd. for $C_{27}H_{29}NO_6$: C, 69.95; H, 6.31; N, 3.02 Found: C, 69.76; H, 6.36; N, 2.95.

B. Hydrogenolysis of the above esters (208 mg, 0.605 mmole) was carried out in the presence of 10% palladium on charcoal (30 mg) at 22° in ethyl acetate (5 ml) and ceased after 30 minutes, when 35.6 ml of hydrogen (1.47 mmoles had been consumed. After being worked up as usual, there were obtained 237 mg of an oil (54% yield) with $R_f$ value of 0.70, 17 mg of a solid, m.p. 200°–230°, with $R_f$ value of 0.62, and 27 mg of oil with $R_f$ value of 0.05. The most mobile oil was identical with norcocaine in all respects.

The above product according to prior procedure could be spin labeled with 3-amino-2,2,5,5-tetramethyl-pyrrolidinyl-1-oxyl to provide the product 3-[4'-(N-norcocainyl)crotonamido]-2,2,5,5-tetramethylpyrrolidinyl-1-oxyl.

EXAMPLE 7.6 --

Conjugate of ecgonine and bovine serum albumin (BSA)

A. Cocaine (5 g) was refluxed in 25 ml water for 6.5 hours. The remaining oil after evaporation of the solution was dissolved in 5 ml hot water. On cooling long, white crystals separated (2.87 g). Another 543 mg were obtained from the mother liquor.

B. Benzoylecgonine (1 g) was refluxed in 25 ml 2N hydrochloric acid for 1 hour. After cooling, the solution was filtered and extracted with ether. The aqueous phase was neutralized with sodium bicarbonate to pH 5.8. On evaporation a white residue remained which was refluxed with 40 ml ethanol (95%), filtered and the solvent evaporated. The oily residue (580 mg) crystallized on addition of 0.5 ml ethanol (130 mg) m.p. 135°–196° (decomp.).

C. Ecgonine (119 mg) was dissolved in 8 ml dry dimethyl formamide (DMF) and cooled to −10°. After addition of 84 μl isobutylchloroformate the reaction mixture was stirred for two hours.

D. BSA (400 mg) was dissolved in 25 ml water together with 2.1 g sodium bicarbonate. The mixed anhydride prepared above was added dropwise and the reaction mixture stirred overnight at 0°. The solution was transferred to a dialysis bag and was dialyzed against 1 l. of water for 24 hours (4 changes of the dialysate, 1:20 dialysis). On lyophilization a white compound was obtained. UV analysis showed that 18 haptens/ molecule BSA were present.

EXAMPLE 7.7 --

Conjugate of p-diazobenzolecgonine with bovine serum albumin (BSA)

A. p-Aminococaine (2.0 g) in 15 ml of water was refluxed with rapid stirring under nitrogen for 6 hours. The solution was allowed to cool to room temperature and then cooled in ice and filtered. The crystals were washed with 5 ml cold water and dried at 0.05 mm Hg for 2 hours to yield 1.2 g clear needlelike crystals, m.p. 287° (dec.). The compound slowly turns brown upon exposure to air and light. Recrystallization of 200 mg from 2 ml boiling water gave an analytically pure sample. Anal. Calcd.: C, 63.14; H, 6.62; N, 9.20 Found: C, 63.32; H, 6.62; N, 9.16.

B. To a solution of 95 mg (0.313 mmoles) para-aminobenzoylecgonine (m.w. 304.34) in 2.0 ml 0.1N hydrochloric acid was added dropwise a solution of 21.5 mg (0.313 mmole) sodium nitrite in 2.0 ml water keeping all solutions cooled to 0° in an ice bath. The diazotized solution was added dropwise over a period of five minutes to a well cooled (ice bath) vigorously stirred solution of 300 mg BSA in 20 ml water at pH 9 (adjusted with 0.1N sodium hydroxide). The pH of the reaction was kept constant by intermittent addition of 0.1N sodium hydroxide and continuous monitoring with a pH meter. The mixture was allowed to stir for 2 hours at 0° after addition was complete. Urea (100 mg) was added and the solution allowed to come to room temperature, desalted on a 100 cm × 5 cm Sephadex G-25 medium column and lyophilized to yield 290 mg light yellow conjugate.

EXAMPLE 7.8 --

Conjugate of N-(p-diazobenzyl-) nor-ecgonine methyl ester with bovine serum albumin (BSA)

To 300 mg (0.83 mmoles) N-(p-aminobenzyl-)nor-ecgonine methyl ester dihydrochloride in 5 ml 0.3N hydrochloric acid at 0° was added a solution of 57 mg (0.83 mmoles) sodium nitrite in ice cold water. After 10 minutes, the diazonium salt solution was added dropwise over a period of five minutes to a well-cooled (ice bath), vigorously stirring solution of 1 g BSA in 50 ml water at pH 9 (adjusted with 2N sodium hydroxide). The pH of the reaction was kept constant by intermittent addition of 2N sodium hydroxide and continuous monitoring with a pH meter. The solution was stirred at 0° for 20 minutes after addition was complete and 100 mg urea and 100 mg β-naphthol was added. The dark red solution was desalted on a 100 × 5 cm Sephadex G-25 (med.) column and lyophilized to give 1.10 g orange conjugate.

EXAMPLE 7.9 --

Conjugate of N-(p-diazobenzyl) nor-ecgonine with bovine serum albumin (BSA)

A. N-(p-Aminobenzyl-) nor-ecgonine methyl ester dihydrochloride (2.0 g, 5.5 mmoles) (prepared above) in 30 ml 2N hydrochloric acid was refluxed for 4 hours, evaporated in vacuo and stored at 0.05 mm Hg over potassium hydroxide pellets overnight. The residue was dissolved in 3 ml of water and 100 ml of hot absolute ethanol was quickly added. Cooling in ice resulted in a fine white precipitate which was filtered and washed with 5 ml cold ethanol. The mother liquor was evaporated in vacuo and the recrystallization repeated. Heating the material produces a yellow color.

Obtained 1.5 g (78%) slightly yellow crystals. TLC $R_f$ 0.2 [conc. $NH_4OH$:EtOH, 1:7, on silica gel] m.p. 235° (decomp.). Anal. Calcd. for $C_{15}H_{22}N_2O_3Cl_2$: C, 51.59; H, 6.35; H, 6.35; N, 8.02; Cl, 20.30 Found: C, 48.71; H, 6.16; N, 7.63; Cl, 19.53.

B. To a solution of 290 mg (0.83 mmoles) N-(p-aminobenzyl)-nor-ecgonine dihydrochloride in 5 ml 0.3 N hydrochloric acid at 0° was added a solution of 57 mg (0.83 mmoles) sodium nitrite in 20 ml water at 0°. After 10 minutes, the diazonium salt solution was was added dropwise over five minutes to a vigorously stirring solution of 1.0 g BSA in 50 ml water at 0° and pH 9. The pH of the reaction was kept constant by intermittent addition of 2N sodium hydroxide and continuous monitoring with a pH meter. After stirring for 20 minutes at 0° 100 mg urea and 100 mg β-naphthol was added and the dark red solution was desalted on a 100 × 5 cm Sephadex G-25 (medium) column using pH 9 water ($NH_4OH$) to elute. The desalted solution was lyophilized to yield 1.0 g orange conjugate.

EXAMPLE 7.10 --

Conjugate of N-carboxymethyl nor-cocaine with bovine serum albumin (BSA)

To 10 ml dry DMF containing 0.42 g (1.0 × $10^{-3}$ mmoles) of the hydrochloride of N-carboxymethyl nor-cocaine (see Example 7.2 ) was added 0.15 g(1.1 × $10^{-3}$ mmoles) isobutyl chloroformate and 0.11 g (1.1 × $10^{-3}$ mmoles) triethylamine. The mixture was stirred at —15° under $N_2$ for 1.5 hours. To the reaction mixture was added BSA at 4° in 100 ml water with 1 g $NaHCO_3$. An additional 70 ml water was added and the mixture stirred overnight. The resulting homogeneous solution was dialyzed against water for 3 days, changing the water 3 times the first day and two times on successive days. The resulting product was lyophilized to dryness, yielding 0.77 g. By U.V. analysis, the degree of conjugation was determined to be 22.4.

EXAMPLE 8.1 --

3-[$O^3$-Estradiolyl)acetamido]-2,2,5,5-tetramethyl-1-pyrrolidinyl-1-oxyl

A. Estradiol-17β (2.0 g, 7.35 mmoles) was combined with 2 ml of methyl chloroacetate, 10 g of finely powdered potassium carbonate and 80 ml of dry acetone. The reagents were mixed and refluxed for 20 hours in the absence of moisture. At the end of this time, the mixture was cooled, filtered, the potassium carbonate washed twice with dry acetone, and the filtrate evaporated to dryness. The residue, a clear oil, was dissolved in 120 ml of methanol and 120 ml of 0.5N sodium hydroxide added while keeping the solution cool. The solution was then heated to reflux and maintained at reflux for 1.5 hours. After lowering the temperature to below reflux, the mixture was acidified with 6N HCl to pH 1. Upon cooling and seeding, the carboxylic acid derivative crystallized, yielding 2.2 g (92%).

Because of a low melting point, the product was combined with 30 ml of methanol and 30 ml of 0.5N sodium hydroxide and refluxed again for 1.5 hours. After acidification with 6N HCl, the mixture was cooled and the crystalline particles isolated. The crystallization from acetone/hexane provided a product with a melting point of 188°–191°.

B. Into 15 ml of ethyl acetate was introduced 100 mg of $O^3$-carboxymethyl estradiol, 50.5 ml (0.32 mmoles) of 3-amino-2,2,5,5-tetramethylpyrrolidinyl-1-oxyl and 56 mg of dicyclohexylcarbodiimide. The mixture was stirred overnight, filtered and the solvent evaporated, leaving 188 mg of residue. A portion of the product was chromatographed on silica gel with ethyl acetate and then dissolved in diethyl ether/chloroform and filtered. The solvent was evaporated and the product dried in vacuo. Anal. Calcd. for $C_{28}H_{21}N_2O_4$: C, 71.61; H, 8.80; N, 5.96 Found: C, 69.93; H, 8.96; N, 5.89.

EXAMPLE 8.2 --

3-[$O^3$-estronyl)acetamido]-2,2,5,5-tetramethylpyrrolidinyl-1-oxyl

Into 15 ml dry ethyl acetate was introduced 100 mg (0.31 mmoles) of $O^3$-carboxymethyl estrone, 50.5 mg of 3-amino-2,2,5,5-tetramethylpyrrolidinyl-1-oxyl (0.32 mmoles) and 66 mg of dicyclohexylcarbodiimide (0.32 mmoles), the mixture stirred for 4 hours and then stored in a freezer. After filtering off the solids, the filtrate was evaporated, yielding 2.15 mg. The residue was dissolved in ethyl acetate and chromatographed on silica gel, an insoluble residue being discarded. The product was isolated from the silica gel and dried in vacuo yielding 94 mg. Anal. Calcd. for $C_{28}H_{39}N_2O_4$: C, 71.92; H, 8.41; N, 5.99 Found: C, 71.69; H, 8.51; N, 6.12.

EXAMPLE 8.3 --

Conjugate of $O^3$-carboxymethyl estradiol with bovine serum albumin (BSA)

$o^3$-Carboxymethyl estradiol (0.34 g) and 110 μl of triethylamine were dissolved in 5 ml of DMF (dry) and the mixture cooled to —15°. To the mixture with stirring was added isobutylchloroformate and the temperature maintained at —10° - 0° for one hour. To a solution of 585 mg of BSA in 100 ml cold water at pH 8.3 was slowly added the above mixture while maintaining the pH between 8.0 – 8.3 by the addition of 0.1N sodium hydroxide. The mixture was stirred for one hour while maintaining the pH, after which time, 0.5 g sodium bicarbonate was added and the mixture stirred overnight at 4'. The solution was very turbid and was centrifuged for 30 minutes at 20,000 rpm. The supernatant was then dialyzed against water over 5 days with 4 changes. The solution was then lyophilized and the product analyzed for number of haptens by ultraviolet analysis. The number of haptens per molecule of BSA was found to be 18.4.

EXAMPLE 8.4 --

N-(2', 2', 5', 5'-Tetramethyl-1'-oxylpyrrolidinyl-3') $O^3$-estradiolylacetamidine A. Estradiol (10 g), 7 ml of chloroacetonitrile and 50 g of potassium carbonate were dissolved in 4 ml of acetone and the mixture refluxed overnight. The solution was then filtered through a silica gel column (7.5 cm diameter × 12.5 cm length) which was packed with 25% hexane in chloroform. The product was eluted with chloroform and fractions 3 – 9 (250 ml each) combined and evaporated. The residual oil was treated with diethyl ether and the resulting crystals filtered and dried after washing with ether. Two crops were obtained to provide a total of 9.96 g. m.p. 112.5°–114° (softens at 97°).

B. To 200 mg of O³-cyanomethyl estradiol was added 3.6 ml of methanol and the mixture warmed to effect solution. To the methanolic solution was added 1.4 ml of sodium methoxide (1 g of sodium per ml of methanol) and the mixture stirred. After about 20 minutes crystals began to form and the stirring was continued. The mixture was allowed to stir overnight, at which time it was filtered, and the precipitate washed with cold methanol in vacuo. The product weighed 175 mg, m.p. 182°–185°. Anal. Calcd. for $C_{21}H_{29}N_1O_3$: C, 73.44; H, 8.51; N, 4.08 Found: C, 73.34; H, 8.41; N, 4.06.

C. A solution of 0.329 g (1 mmole) of 3-methoxyiminomethylestradiol and 0.227 g (1.5 mmole) of 3-amino-2,2,5,5-tetramethylpyrrolidinyl-1-oxyl in 5 ml dry dioxane is warmed to 50° and maintained at that temperature for 4 hours. The progress of the reaction is followed by TLC (10% methanol:chloroform). At the completion of the reaction, the mixture is evaporated to dryness, and the crude products purified by preparative TLC on silica gel.

EXAMPLE 8.5 --

N-(O³-estradiolylethyl) N'-(2,2,5,5-tetramethyl-1-oxylpyrrolidinyl-3) thiourea

A. A suspension was prepared of 200 mg of lithium aluminum hydride in 25 ml of diethyl ether. To the suspension was added 200 mg of O³-cyanomethylestradiol in 10 ml of diethyl ether and 7.5 ml of tetrahydrofuran over a period of 20 minutes while stirring under a nitrogen atmosphere. The mixture was then refluxed for one hour and allowed to cool. To the mixture was then added successively 0.3 ml water, 0.3 ml 10% NaOH and 1 ml water. The inorganic salts were filtered off, and the organic layer extracted once with water (pH 10) and once with brine (pH 10) dried and evaporated to leave an oil residue. The residue was dissolved in a mixture of 10 ml methanol and 10 ml diethyl ether and anhydrous hydrochloric acid bubbled in. The resulting precipitate was filtered and isolated. Recrystallization from methanolether yielded an analytical sample. m.p. 271°–274° (dec.)

B. The above amine hydrochloride (76 mg, .22 mmole) was added to 5 ml of water, followed by the addition of 88 mg potassium bicarbonate and 10 ml chloroform and the mixture stirred vigorously for 30 minutes. Some solid remained, and additional potassium bicarbonate was added, followed by stirring for an additional 20 minutes. A small amount of solid still remained. To this mixture was then added 50 μl of thiophosgene and the mixture stirred overnight. The organic phase was separated from the aqueous phase and washed once with water and the volatiles removed in vacuo. The product was chromatographed on silica gel with 5% methanol/chloroform.

C. To a solution of 0.36 g O³-isothiocyanatoethyl estradiol (1 mmole) in 5 ml ethyl acetate is added 0.15 g (1 mmole) of 3-amino-2,2,5,5-tetramethylpyrrolidinyl-1-oxyl in 1 ml ethyl acetate. The reaction is allowed to stir at room temperature and the course of the reaction followed by TLC (10% methanol/chloroform). The solvent is evaporated and the crude product is purified by preparative TLC over silica gel.

EXAMPLE 8.6 --

N-(2', 2', 5', 5'-Tetramethyl-1'-oxylpyrrolidinyl-3') 6-[(O-aminocarbonylmethyl)oximino]estradiol A. To a solution of 9 g of estradiol diacetate in 31 ml glacial acetic acid was added a solution of 7.6 g of chromium trioxide in 6.1 ml water and 45 ml acetic acid. The mixture was stirred at room temperature for 20 hours. After diluting the mixture to 500 ml with water, the aqueous solution was extracted 3 times each with 500 ml of diethyl ether and once with 100 ml of diethyl ether and the combined ether layers washed with saturated sodium bicarbonate until the aqueous solution was pink. The ether layer was then washed with ⅝ volume saturated sodium bicarbonate, 1N sodium carbonate (50 ml) and then 3 volumes 1N sodium carbonate, followed by two washings of 200 ml each of water and one washing with brine. After drying the ether layer, the ether was evaporated to yield 5.8 g of an oil. The product was purified by chromatographing with 250 g of silica gel packed with chloroform and eluting with 5% methanol/chloroform. Most of the product was in the first to sixth fractions. The product in the first five fractions was crystallized from aqueous ethanol followed by recrystallization in ethanol.

B. 6-Oxoestradiol diacetate was prepared according to the method of Dean, et al., Steroids, 18, 593 (1971). A few grams of the diacetate was dissolved in 20% methanolic potassium hydroxide and stirred at room temperature for 21 hours. The mixture was poured into 200 ml of water, acidified with concentrated hydrochloric acid and extracted 3 times with 100 ml diethyl ether. The ether extracts were dried and the solvent evaporated. A portion of the residue was crystallized from dichloromethane/ether/pet. ether. m.p. 271°–273°

C. Into 20% v/v aqueous methanol and 20 ml 1 M aqueous sodium acetate was introduced 200 mg of 6-oxoestradiol-17β and 500 mg of O-carboxymethylhydroxylamine hemihydrochloride. Dissolution was incomplete and about 15 ml additional methanol was added. After 47 hours, the solution was concentrated. Water was then added to bring the volume to 200 ml and the pH adjusted to 8.5 with 2N sodium hydroxide. The mixture was then extracted 3 times each with 200 ml of diethyl ether. To the vigorously stirred aqueous phase in combination with 100 ml of diethyl ether cooled in an ice bath was added 1N hydrochloric acid to bring the pH to 2.0. The layers were separated and the aqueous layer extracted 3 times each with 200 ml cold diethyl ether. The ether layers were combined, washed 3 times each with 200 ml water, once with 200 ml saturated sodium chloride solution and then dried, filtered and evaporated to yield 235 mg. m.p. 197°–198° (darkens 192°). The product was then recrystallized from acetone. m.p. 199°–200.5°

D. A solution of 6-(O-carboxymethyl)oximinoestradiol (0.15 g, 0.42 mmole) in 5 ml ethyl acetate is added dropwise with stirring to a solution of 71 mg (0.45 mmole) of 3-amino-2,2,5,5-tetramethylpyrrolidinyl-1-oxyl and 93 mg (0.45 mmole) of dicyclohexylcarboddimide in 4 ml ethyl acetate. The reaction mixture is allowed to stir for 24 hours at room temperature and the insoluble urea is then removed by filtration. The residue is evaporated to dryness and the crude product is purified by preparative TLC (silica gel; methanol:chloroform; 1:10).

EXAMPLE 8.7 --

Conjugate of 6-(O-carboxymethyl)oximinoestradiol with bovine serum albumin (BSA)

Into 6 ml dimethylformamide was dissolved 425 mg of 6-(O-carboxymethyl)oximinoestradiol and 0.49 ml triethyl amine added, and the mixture cooled to $-8°$. To the mixture was added with stirring 0.16 ml isobutylchloroformate and the temperature maintained at $-8°$ for 0.5 hours and then raised to $0°$ and maintained for 0.5 hours. To the mixture was then added dropwise 666 mg of BSA in 200 ml water ($3°$) keeping the pH in the range of 8.5–9 by the addition of 0.05N sodium hydroxide. The mixture was stirred in an ice bath for one hour, the pH adjusted to 8, and then 1 g sodium bicarbonate added, and the mixture stirred in the cold room at $4°$ overnight. After centrifuging for 20 minutes at 15,000 rpm, the supernatant was decanted, and the residue dialyzed against 3.5 l. water ($4°$). The water was changed at 3 hours, 6 hours, 22 hours, 30 hours, 102 hours, 110 hours, and stopped at 126 hours. The dialyzed material was centrifuged at 19,000 rpm for 30 minutes, the supernatant decanted, and the residue lyophilized. The yield was 750 mg. By ultraviolet analysis, the degree of conjugation was found to be about 22.

Immunoassays

The compounds of this invention were employed in assaying for a wide variety of ligands. 2,4-Dinitrophenylaniline was accurately assayed, demonstrating that simple small molecules can be determined according to the method employing the compounds of this invention. A number of other compounds having biological activity were also assayed.

While it was found that some variation in procedure was desirable with a few of the assays, for the most part, this did not go to operability but to enhance sensitivity. Also, as is well known, it was found that early harvests of antibodies were not always as good as later harvests of antibodies.

In evaluating an assay for commercial use, not only must the sensitivity for the ligand being assayed be determined, but also cross-reactivity. In some instances cross-reactivity is desirable, where a class of compounds is to be screened, e.g., barbiturates. In other instances substantial specificity will be desired, for example, with a hormone. Therefore, when bonding a hapten to an antigenic protein, these factors will be considered in the molecular engineering.

To demonstrate the analysis for ligands by the subject method, the labeled hapten, 3-(2',4'-dinitrophenylamino)-2,2,5,5-tetramethylpiperidine-1-oxyl, was added to the dinitrophenyl antibodies in an aqueous solution. (The antibodies were prepared according to Eisen, et al., JACS, 75, 4583 (1953) and the labeled hapten was prepared in accordance with Hsia, et al, Archives of Biochemistry and Biophysics 132, 466 (1969)). The following procedure was employed. The quantities of the compounds were chosen by adding small portions of the haptens to the antibody solution until the ESR signal intensity began to rise sharply with addition of each portion. At this point, all the binding sites on the antibodies were occupied by the label and the addition was stopped. Increasing amounts of N-epsilon-dinitrophenyllysine were then added to the solution. With the addition of increasing amounts of N-epsilon-dinitrophenyllysine to the antibodies-labeled hapten complex, an increase in the ESR signal was observed.

The antibody solution had a concentration of about 2 mg/ml which was equal to about $1-2 \times 10^{-5}$ M of binding site. The labeled hapten was dissolved in 20 percent aq. methanol at about $1-2 \times 10^{-5}$ M concentration. Approximately 10 $\mu$l of the antibody solution and 10–20 $\mu$l of the labeled hapten solution were combined and varying amounts of $10^{-5}$ M solution of N-epsilon-dinitrophenyllysine in water added, the maximum being 14 $\mu$l.

By using appropriate standards, the ESR signal intensity may be related to the concentration of the N-epsilon- dinitrophenyllysine in solution. Therefore, by taking an unknown solution suspected of having such a hapten, and introducing a standardized amount of the antibody-hapten complex, one can rapidly determine the concentration of the N-epsilon- dinitrophenyllysine in solution.

To illustrate the subject method in relation to a more useful hapten a variety of studies were made with morphine. Morphine antibodies were prepared by injection of the conjugated morphine prepared in Example 2.10 in rabbits as described earlier. The harvested serum was used in the following experiments:

Morphine antibodies were combined with the spin labeled morphine prepared by the method of Example 2.1. The quantities of the two components were chosen by a titration similar to that described for bonding labeled hapten to the dinitrophenyl antibodies. To an aqueous solution of the combined labeled norphine and morphine antibody were added increasing amounts of morphine and the change in the ESR signal intensity was observed.

Codeine is also detected by the same procedure because of its close structural similarity to morphine. Other closely related compounds such as nalorphine and morphine-$O^3$-glucuronide can also be detected, whereas the assay is insensitive to distantly related analogs such as methadone and unrelated compounds such as amphetamines.

As mentioned, a preferred application of the invention is to test for the presence of a drug in a biological fluid. To further illustrate, urine of drug addicts was tested in accordance with the following procedure. Morphine-$O^3$-glucuronide represents the main excretion product of morphine and heroin in humans. About 80% of the total morphine ingested appears as morphine glucuronide in the urine. Since the above spin labeled morphine combined with morphine antibodies can be used to detect both this metabolite and morphine, the assay is especially effective.

Detection of Morphine and its Metabolite in Urine

The urines were added to solutions containing spin labeled morphine of Example 2.1 bound to morphine antibody in about pH 7.9 buffered solution and the amount of increase in the ESR signal was recorded. The increase was recorded as a percentage of the maximum increase of signal that could be obtained in the presence of high concentrations of morphine.

The labeled morphine was first dissolved in a few drops of ethanol and then dissolved in water to provide a solution of $2 \times 10^{-5}$ M concentration. The antibody concentration in water was about $1-2 \times 10^{-5}$ M based on binding sites. Included in the antibody solution was approximately 0.4 M Tris or 0.6 M sodium borate to provide a pH of 7.5 with the former and 7.9 with the latter. The pH will drop due to dilution and the presence of acid in the urine. To 20 µl of urine was added sufficient sodium dichromate to provide a concentration of $2 \times 10^{-2}$ M in order to destroy any interfering reducing substances. The urine sample was then combined with 10 µl of an equivolume mixture of the antibody solution and the labeled morphine solution.

The data given for urine samples 1–5 in Table III are the percent increases for a randomly selected set of urine samples from people who had taken no narcotic agents for at least one week. Urine samples 6 – 10 in Table III were from known heroin addicts and patients known to be taking codeine. The high percentage increases for the latter group demonstrate the efficacy of the assay technique.

TABLE III

| Controls | | Study Group | | |
|---|---|---|---|---|
| Urine Sample No. | % Signal Increase | Urine Sample No. | % Signal Increase | Drug Taken |
| 1) | 6 | 6) | 58 | heroin |
| 2) | 3 | 7) | 81 | heroin |
| 3) | 5 | 8) | 100 | heroin |
| 4) | 7 | 9) | 75 | codeine |
| 5) | 4 | 10) | 62 | codeine |

As a demonstration of the sensitivity of the method, the results of the ligand assay technique were compared with the present commercial TLC test. In the TLC test, morphine is removed from the urine by solvent extraction and, after evaporation of the extracts, the residue is analyzed by thin layer chromatography. Since the morphine glucuronide is not extracted with benzene, only morphine is detected, and the test is relatively insensitive. In Table IV the results of the two assay methods are compared for the urine from a single heroin user who admitted taking the drug on the second and fifth days. It is apparent from the data that the ligand assay technique permits detection of the drug even three days after it was taken. This conclusion was verified by comparing the data with data obtained on the same urine samples using an improved TLC technique in which the morphine glucuronide is first hydrolyzed with acid to give free morphine. These data are included for comparison in Table IV. Although the improved TLC technique is still not as sensitive as the hapten assay technique, the results provide confirmation that the labeled ligand technique gives valid data.

TABLE IV

| Day | % Signal Increase | TLC Results | Improved TLC Results |
|---|---|---|---|
| 1 | 17 | – | + |
| 2 | 57 | + | + |
| 3 | 32 | – | + |
| 4 | 26 | – | + |
| 5 | 47 | + | + |
| 6 | 26 | – | + |
| 7 | 16 | – | – |
| 8 | 8 | – | – |
| 9 | 40 | + | + |

Barbiturate Assay

Seconal

Antibody (γ-globulin) was prepared using secobarbital-bovine serum albumin conjugate, prepared as described in Example 4.13. The spin label was N-2,2,5,5-tetramethylpyrrolidin-1-oxyl-3-yl 5-(gamma-crotonamide)-5-(2′-pentyl) barbituric acid. The γ-globulin had a binding constant of $2.2 \times 10^7$.

In carrying out the assay, two solutions were prepared. The first, solution A, employed 1,000 µl of γ-globulin ($7.35 \times 10^{-5}$ M) in binding sites, 725 µl of 1.5 M potassium phosphate solution adjusted to pH 7, and 87.5 µl of water. The second solution, solution B, employed 1,175 µl of the seconal spin label ($5 \times 10^{-5}$ M) and 637.5 µl of water.

The procedure employed for the assay is the same as for phenobarbital, infra. The following table indicates the response to various barbiturates, the results being reported as percent mobilization.

TABLE V

| Compound | Conc. µg/ml* | % Mobilization |
|---|---|---|
| secobarbital | 2.6 | 21 |
| sodium pentobarbital | 2.5 | 12 |
| amobarbital | 2.3 | 10 |
| sodium phenobarbital | 2.5 | 2 |
| thiopental sodium | 2.6 | 9 |
| glutethimide | 2.2 | 0 |

*$1 \times 10^{-5}$ M

While a variety of other barbiturates would be detected by the same antibody in accordance with the assay, the greatest sensitivity is achieved with secobarbital. Furthermore, by virtue of the cross reactivity, one can get a rapid indication as to whether there is any barbiturate in the sample. Various means could then be used to determine which barbital is involved.

Employing the secobarbital antibody, the following minimum concentrations of other barbitals could be detected: pentobarbital 2 µg/ml; amobarbital, 2.5 µg/ml; thiopental sodium, 3.5 µg/ml; heptabarbital, 7 µg/ml; and sodium phenobarbital, 40 µg/ml.

To test the assay with urine samples from donors who denied taking barbiturates, a total of 110 samples were tested. 106 samples gave readings below about 1 µg/ml indicating the substantial absence of any barbiturates recognized by the secobarbital antibody. Three samples gave results of 1.1 to 1.4 µg/ml which upon retesting were negative. The original results are believed to be due to erroneous procedures. One sample which gave between 12 - 13 µg/ml was checked by TLC and found to contain seconal.

In varying the procedure for the seconal assay, the loading of choice (antibody binding sites/spin label molecules) was 1.25, a mildly underloaded system. The preferred pH was 7, changing the pH to either 8 or 6 resulting in no significant change. Increasing buffer concentration had little effect. The order of addition of unknown sample and antibody followed by the addition of spin label was found to give a superior result over the order of addition of combining the spin label and antibody, followed by the addition of the unknown sample.

Phenobarbital

Phenobarbital antibody (γglobulin) was prepared using phenobarbital - bovine serum albumin conjugate prepared as described in Example 4.12. The ligand analog spin label was N-2′,2′,5′,5′-tetramethylpyrrolidin-1′-oxyl-3′-yl 5-ethyl-5-phenylbarbituryl-1-acetamide. The γ-globulin had a binding constant of $9.4 \times 10^6$.

In carrying out the assay, two solutions were prepared. The first, solution A, employed 1,000 µl of γ- globulin (5.96 × 10$^{-5}$ M in binding sites), and 475 μl of 1.5 M potassium phosphate adjusted to pH 7. The second solution, solution B, employed 404 μl of the phenobarbital spin label (1.18 × 10$^{-4}$ M) and 956 μl of water and 115 μl of 1.5 M potassium phosphate buffer.

Two plastic cups were employed: one cup contained 5 μl of 0.2 M sodium dichromate; the second contained 5 μl of solution A. A 50 μl aliquot of the sample to be tested is measured with a Drummond capillary and added to the dichromate in the first cup and exactly 20 μl of the resulting solution is withdrawn with the same capillary and added to the second cup. To the sample in the second cup is then added 5 μl of solution B. An aliquot of the solution is then drawn up into an ESR capillary and the spectrum read.

To test the assay with urine samples from donors who denied taking any barbiturates, a total of 100 samples was assayed. All the samples fell below a mobilization of 15%.

Employing the phenobarbital antibody, the following minimum concentration (15% mobilization) of other barbiturates could be detected: mephobarbital, 0.9–1.0 μg/ml; heptabarbital, 2.9–3 μg/ml; amobarbital, 3.1–3.2 μg/ml; thiopental and butisol, 7.2–7.3 μg/ml; and seconal, 7.3–7.4 μg/ml.

To further test the assay, 27 urine samples were taken from various donors who indicated they had taken barbiturates. Of the 27 samples tested, 22 were positive. Of the 5 negative results, one gave a positive with the seconal assay, two donors had taken the barbiturate a long time prior to giving the samples, and the remaining two samples are not readily explained.

In varying the procedures for the phenobarbital assay, higher ratios of antibody binding sites to spin label than employed above were found to be less satisfactory. Changing the pH from 7 did not offer any advantage. The optimum final buffer concentration was found to be about 0.1 M.

The following table shows the results with phenobarbital and analogous compounds.

TABLE VI

| Compound | Conc. μg/ml* | % Mobilization |
|---|---|---|
| phenobarbital | 2.5 | 25 |
| sodium pentobarbital | 2.5 | 10 |
| amobarbital | 2.3 | 16 |
| secobarbital | 2.6 | 7 |
| mephobarbital | 2.5 | 32 |
| metharbital | 2.5 | 6 |
| glutethimide | 2.2 | 0.5 |

*1 × 10$^{-5}$ M

Amphetamine Assay

Amphetamine antibody was prepared by employing amphetamine-bovine serum albumin conjugate prepared in accordance with Example 3.10. The spin label was prepared according to Example 3.1 and was 3-(N-(1'-phenyl-2'-propyl)glycinamido2,2,5,5-tetramethyl-1-pyrrolidinyloxyl. The binding constant for the γ-globulin was 4.5 × 10$^6$.

In carrying out the assay, two solutions were prepared: solution A comprised 22 μl of γ-globulin (2.18 × 10$^{-4}$ M in binding sites); 144 μl of 2 M borate buffer, pH 8, and 99 μl of saline solution; solution B had 160 μl of a 2.8 × 10$^{-5}$ M solution of spin label and 105 μl of water.

Two plastic cups were employed. In one cup was 2.5 μl of 0.2 M sodium dichromate. In the other cup was 5.0 μl of antibody solution. The sample was transferred employing a 25 μl Oxford Sampler and introduced into the cup containing dichromate. The dichromate sample solution was agitated by means of the sample, drawn up with the sampler and introduced into the cup containing antibody, without touching the antibody. To the resulting solution was then added 5 μl of spin label, the sample was then stirred with an ESR capillary tube, the sample allowed to rise into the capillary and the spectrum read.

The following table indicates the results:

TABLE VII

| Compound | Conc. μg/ml | M × 10$^{-5}$ | % Mobilization |
|---|---|---|---|
| amphetamine.HCl | 1.7 | 1.1 | 26 |
| phenylpropanolamine.HCl | 2.5 | 1.5 | 13 |
| phenethylamine | 2.5 | 2.1 | 26 |
| methamphetamine.HCl | 2.5 | 1.3 | 29 |
| benzophetamine.HCl | 2.5 | .9 | 12 |
| mephentermine.H$_2$SO$_4$ | 2.5 | .8 | 28 |
| propylhexedrine.HCl | 250 | 131 | 71 |

It is noted that the antibody recognizes besides amphetamine, methamphetamine and mephentermine, which have structural similarities to amphetamine.

In 100 urine studies, the vast majority gave mobilizations of 10% or less, the background value. Four "normal" urines were between ten to fourteen percent. Of six that were greater than 14 percent all individuals indicated taking substances known to cross react, e.g., phenethyl biguanide; decongestants containing phenylpropanolamine, amphetamine and pseudophedrine; and mescaline which is often cut with amphetamine. Four urines indicated as amphetamine positive by an independent clinic, gave positive results under the assay in the range of 0.7 – 1.5 μg/ml.

The loading ratio of spin label to antibody binding sites was 0.95 which gave a peak ratio of 5 (10$^{-3}$ molar amphetamine/saline). Higher loading ratios gave somewhat lower peak intensity ratios.

Methadone assay

The spin immunoassay was carried out similarly to the prior assays. Two plastic cups were employed, one cup containing 5 μl of 0.2 molar sodium dichromate and the second 5 μl of borate buffered antibody at pH 8. Sufficient buffer is present in the antibody solution to provide a final concentration of 0.18 molar. To the dichromate is added 50 μl of sample and a 20 μl aliquot is transferred from the first cup to the second cup containing the antibody solution. To the resulting solution was then added 10 μl of a solution of the spin label (prepared as described in Example 6.1) at a concentration of 3 × 10$^{-6}$ molar.

Fifty-five urine samples were tested according to the above procedure. The urines were collected from a methadone clinic. Only one urine which had been marked as being methadone positive by thin layer chromatography gave a negative result. Samples which indicated low methadone concentrations were run through the morphine assay to ensure that high concentrations of morphine might not be indicating a false positive.

In one urine sample, a positive reading was obtained with the methadone test which reverted to a normal background reading after three minutes. In this instance it is believed that the donor was a borderline diabetic who was taking DBI, a metabolite of which may have been oxidized under the conditions of the reaction to give an unstable radical. The results clearly indicate the excellent correlation between the subject assay and thin layer chromatography.

In variations of the test, it was found that an appropriate loading factor was 1.15:1 (spin label/antibody binding sites). Variation from this ratio resulted in decreased sensitivity. Dilution of the spin label concentration required a reduced scan speed to achieve the same results.

The following table indicates the substantial absence of cross-reactivity between methadone and structurally similar drugs.

TABLE VIII

| Compound | Conc. μg/ml | % Mobilization |
|---|---|---|
| methadone | 3.1 | 44 |
| demerol | 3.0 | 7 |
| thorazine | 3.4 | 9 |

Cocaine Assay

The spin labeled compound employed was prepared according to Example 7.1. It was found that the binding constant diminished with time unless the spin label was stored at pH 5 in the absence of any buffer (however, carbon dioxide was bubbled through the solution) in distilled water (substantially metal ion free).

In carrying out the assay, reagents were employed which provided a final antibody concentration (based on binding sites) of $4 \times 10^{-6}$ and a spin label to antibody binding site ratio of 1.15:1. A borate buffer was used at 1.18 M. In the test 10μl of spin label and antibody solution were combined with 20 μl of sample.

When testing urine, the background mobilization was equivalent to 1μg/ml cocaine. The results with a number of drugs were graphed. From the graph, the results which should be obtained at a concentration of 10 μg/ml are reported in the following table.

TABLE IX

| Compound | % Mobilization |
|---|---|
| cocaine | 80 (49)* |
| mephentermine | 35 |
| dextromethorphan | 33 |
| phenylpropanolamine | 26 |

*1 μg/ml

A second cocaine assay was devised employing as the spin label a compound prepared as described in Example 7.2. The procedure described above was employed with a 1:1 spin label to antibody site ratio, and an assay concentration of spin label of $5.25 \times 10^{-6}$ M. Seventeen urine samples from people who had snuffed cocaine were taken and assayed some time thereafter. Eight of the eleven samples taken 12 or 24 hours after snuffing were positive.

Ecgonine assay

The spin labeled compound employed was prepared according to Example 7.1. A ratio of antibody binding sites to spin label of 1:1.5 was used with an assay concentration of spin labelled compound of $2.64 \times 10^{-6}$ M. Seventeen urine samples which had been tested by the cocaine assay were tested with the ecgonine spin label.

Eleven samples, of which eight were positive by the above cocaine assay from eleven donors who had snuffed cocaine within 12 to 24 hours, had been frozen and then thawed inadvertently. Only one remained positive by the cocaine assay, but seven were positive by the ecgonine assay.

With urines spiked with benzoyl ecgonine, the following table indicates the results.

TABLE X

| No. of samples tested | Urine spiked with × μg/ml | Range of results for assays, μg/ml |
|---|---|---|
| 10 | 0 | <0.10 – 0.75 |
| 10 | 0.5 | 0.65 – 3.8 |
| 10 | 5.0 | 7.7 – 10.0 |
| 10 | 50.0 | 27.0 – 39.0 |

By employing compounds of the subject invention in combination with antibodies prepared in accordance with the subject invention, a rapid and convenient method is provided for accurately determining a wide variety of biologically interesting materials. Furthermore, by contrast with prior art methods, the subject method provides a higher degree of accuracy and freedom from other interfering materials. Since the radical ligand analog can be prepared with minimum interference with spatial geometry and salient polar features of the molecule, and there is no concern with retention of the physiological activity of the molecule to be assayed, the method is extremely versatile. In addition, reagents can be prepared and kept for long periods of time without significant change in activity or easily calibrated, and determination rapidly made without extensive manipulation or long periods of waiting. Isolation or substantial separation of the material to be assayed from other groups is generally not required. The use of radioisotopes which are frequently dangerous and have difficulties in manipulation is avoided. Also, the subject method does not suffer from the disadvantages of the colormetric techniques, which cannot be carried out in opaque or turbid solutions.

Although the foregoing invention has been described in some detail by way of illustration and example for purposes of clarity of understanding, it will be obvious that certain changes and modifications may be practiced within the scope of the appended claims.

What is claimed is:

1. A spin labeled reagent which is of the formula:

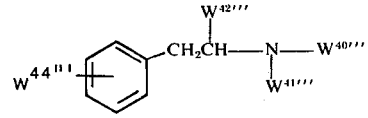

wherein one of $W^{40'''}$, $W^{42'''}$, and $W^{44'''}$ is -X*-A*; when other than -X*-A*;
$W^{40'''}$ is hydrogen;
$W^{42'''}$ is methyl; and
$W^{44'''}$ is hydrogen;
$W^{41'''}$ is hydrogen or methyl;
X* is -Z-CONH-, wherein Z is hydrocarbylene of from 1 to 7 carbon atoms, having from 0 to 1 site of ethylenic unsaturation, with the proviso that when $W^{44'''}$ is -X*-A*, X* is -O-Z-CONH-; and
A* of the formula:

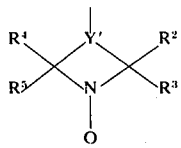

wherein $R^{2-5}$ is alkyl of from 1 to 3 carbon atoms and Y' is a trivalent radical of from 1 to 3 carbon atoms and 0 to 1 heteroatoms, wherein said heteroatom is oxygen, sulfur or nitrogen.

2. A spin labeled reagent according to claim 1, wherein Y' is trivalent radical of from 1 to 3 carbon atoms.

3. A spin labeled reagent according to claim 1, which is {4'-(1''-phenyl-2''-propylamino)-crotonamido}2,2,5,5-tetramethylpyrrolidinyl-1-oxyl.

4. A spin labeled reagent according to claim 1, which is 3-{N-(1'-phenyl-2'-propyl)glycinamido}-2,2,5,5-tetramethylpyrrolidinyl-1-oxyl.

5. A spin labeled reagent according to claim 1 which is 3-{p-(2'-aminopropyl-1')phenoxy)acetamido}-2,2,5,5-tetramethylpyrrolidinyl-1-oxyl.

6. A spin labeled reagent according to claim 1, which is 3-{5'-(1''-phenyl-2''-propylamino)pentanamido}-2,2,5,5-tetramethylpyrridolinyl-1-oxyl.

* * * * *